(12) United States Patent
Small

(10) Patent No.: US 7,456,284 B2
(45) Date of Patent: Nov. 25, 2008

(54) METHODS FOR PRODUCING A HEXADENTATE BIMETALLIC COMPLEX

(75) Inventor: Brooke L. Small, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 492 days.

(21) Appl. No.: 11/009,916

(22) Filed: Dec. 10, 2004

(65) Prior Publication Data

US 2006/0128958 A1 Jun. 15, 2006

(51) Int. Cl.
C07F 15/02 (2006.01)
C07F 15/00 (2006.01)
(52) U.S. Cl. .............................. 546/2; 546/10
(58) Field of Classification Search ............... 546/2, 546/10
See application file for complete search history.

(56) References Cited

U.S. PATENT DOCUMENTS

| 4,971,986 | A | 11/1990 | Stanek et al. |
| 5,696,240 | A | 12/1997 | Vallarino et al. |
| 5,955,555 | A | 9/1999 | Bennett |
| 6,103,946 | A | 8/2000 | Brookhart, III et al. |
| 6,214,761 | B1 | 4/2001 | Bennett |
| 6,489,497 | B1 | 12/2002 | Brookhart, III et al. |
| 6,548,672 | B1 | 4/2003 | Gibson et al. |
| 6,562,973 | B1 | 5/2003 | Liu |
| 7,045,632 | B2 * | 5/2006 | Small ............... 546/264 |
| 2002/0028941 | A1 | 3/2002 | De Boer et al. |
| 2003/0036615 | A1 | 2/2003 | Brookhart, III et al. |
| 2003/0050494 | A1 | 3/2003 | Brookhart, III et al. |

FOREIGN PATENT DOCUMENTS

| CN | 1306014 A | 8/2001 |
| EP | 1 229 020 A1 | 8/2002 |
| EP | 1229020 A1 | 8/2002 |
| WO | WO 01/10875 A1 | 2/2001 |
| WO | WO 01/36379 A1 | 5/2001 |
| WO | WO 01/58874 A1 | 8/2001 |
| WO | WO 02/00339 A2 | 1/2002 |
| WO | WO 02/28805 A2 | 4/2002 |
| WO | WO 03/011876 A | 2/2003 |
| WO | WO 2004/078799 A1 | 9/2004 |

OTHER PUBLICATIONS

Britovsek, George J.P., et al., "Oligomerisation of Ethylene by Bis(imino)pyridyliron and -cobalt Complexes," Chem. Eur. J, vol. 6, No. 12, 2000, pp. 2221-2231.

Kumar, R.N., et al., "Mononuclear and Binuclear Complexes of Fe(II) and Cu(II) with 2,6-Diacetyl Pyridine Monoxime and Phenylene Diamine," Asian Journal of Chemistry, vol. 11, No. 3, 1999, pp. 964-969.

Nelson, S. Martin, et al., "Metal-ion Controlled Reactions of 2,6 Diacetylpyridine with 1,2-Diaminoethane and 2,6-Diformylpyridine with o-Phenylenediamine and the Crystal and Molecular Structure of a Pentagonal Pyramidal Cadmium(II) Complex containing Unidentate o-Phenylenediamine," Journal of the Chemical Society, Dalton Transactions, Inorganic Chemistry, vol. 2, 1982, pp. 407-415.

Small, Brooke L., et al., "Highly Active Iron and Cobalt Catalysts for the Polymerization of Ethylene," Journal of the American Chemical Society, vol. 120, No. 16, 1998, pp. 4049-4050.

Small, Brooke L., et al., "Iron-Based Catalysts with Exceptionally High Activities and Selectivities for Oligomerization of Ethylene to Linear a-Olefins," Journal of the American Chemical Society, vol. 120, No. 28, 1998, pp. 7143-7144.

International Search Report and Written Opinion of the International Searching Authority, PCT/US2004/004472, Jul. 16, 2004, 7 pgs.

U.S. Appl. No. 10/782,554, "Olefin Oligomerization," Small, Brooke L., Filing Date: Feb. 19, 2004, Specification (32 pgs).

International Search Report and Written Opinion, PCT/US2005/042175, Aug. 17, 2006, 9 pgs.

Adams, Harry, et al., "Complexes of Ligands providing Endogenous Bridges. Part 1. The Syntheses and Crystal Structures of Barium and Lead (II) Complexes of Macrocyclic Schiff Bases derived from Heterocyclic Dicarbonyls and 1, n- Diamino-n'-hydroxyalkanes (n,n'=3,2; 4,2; 5,3)," J. Chem Soc. Dalton Trans., Issue 1, 1987, pp. 207-218.

* cited by examiner

*Primary Examiner*—Charanjit S Aulakh
(74) *Attorney, Agent, or Firm*—Conley Rose, P.C.; Rodney B. Carroll; Stephen R. Jenkins

(57) ABSTRACT

The present application discloses methods for producing a hexadentate bimetallic complex. A method may comprise contacting an acyliminepyridine compound, a metal salt, and an amine to form a mixture; and recovering the hexadentate bimetallic complex from the mixture. A method may also comprise forming at least one imine bond in the presence of a metal salt, metal complex, or combinations thereof. The metal salt may be iron, cobalt, nickel, chromium, vanadium or mixtures thereof. The acyliminepyridine compound may be a mono-acyliminepyridine in instances where the amine is a diamine. In such instances, the mono-acyliminepyridine compound to diamine molar ratio may be in the range of about 2:1; and the mono-acyliminepyridine compound to metal salt molar ratio may be in the range of about 1:1. Methods for preparing an acyliminepyridine compound for use in preparation of a hexadentate bimetallic complex are also disclosed. Such methods may comprise contacting a di-acylpyridine with a first amine to form a first mixture, and recovering the acyliminepyridine compound from the first mixture.

25 Claims, No Drawings

METHODS FOR PRODUCING A HEXADENTATE BIMETALLIC COMPLEX

CROSS-REFERENCE TO RELATED APPLICATIONS

The subject matter of the present application is related to co-pending U.S. patent application Ser. No. 10/379,828, filed Mar. 4, 2003, which is incorporated by reference herein in its entirety.

FIELD OF THE INVENTION

The present application relates generally to olefin oligomerization. More particularly, the present application relates to novel methods of producing a hexadentate bimetallic complex employed in the oligomerization of olefins.

BACKGROUND OF THE INVENTION

Olefins, also commonly known as alkenes, are important items of commerce. Their many applications include employment as intermediates in the manufacture of detergents, as more environmentally friendly replacements where refined oils might otherwise be used, as monomers, and as intermediates for many other types of products. An important subset of olefins are olefin oligomers, and one method of making olefin oligomers is via oligomerization of ethylene, which is a catalytic reaction involving various types of catalysts. Examples of catalysts used commercially in polymerization and oligomerization of olefins include alkylaluminum compounds, certain nickel-phosphine complexes, and a titanium halide with a Lewis acid, such as diethyl aluminum chloride.

Another group of olefin polymerization catalysts is derived from pyridine bis-imines. With catalysts of this type, a nitrogen-based ligand engages in a coordination reaction with a transition metal salt. The coordination reaction forms a metal complex, which is a catalyst precursor. The metal complex further reacts with another precursor or activator to generate a metal alkyl or metal hydride species. The catalyst resulting from the generation of the metal alkyl or metal hydride species polymerizes olefins.

Applications and demand for olefin polymers and oligomers continue to multiply, and competition to supply them correspondingly intensifies. Thus, additional novel and improved catalysts and methods for olefin polymerization and oligomerization are desirable.

SUMMARY OF THE INVENTION

In various embodiments, a method is presented for producing a hexadentate bimetallic complex. In some embodiments, the method may comprise contacting an acyliminepyridine compound, a metal salt, and an amine to form a mixture; and recovering the hexadentate bimetallic complex from the mixture. In other embodiments, a method for producing a hexadentate bimetallic complex comprises forming at least one imine bond in the presence of a metal salt, metal complex, or combinations thereof. The metal salt may be iron, cobalt, nickel, chromium, vanadium or mixtures thereof. The acyliminepyridine compound may be a mono-acyliminepyridine in instances where the amine is a diamine. In such instances, the mono-acyliminepyridine compound to diamine molar ratio may be in the range of about 2:1; and the mono-acyliminepyridine compound to metal salt molar ratio may be in the range of about 1:1. Embodiments of a method for preparing an acyliminepyridine compound for use in preparation of a hexadentate bimetallic complex are also presented. Such embodiments may comprise contacting a di-acylpyridine with a first amine to form a first mixture, and recovering the acyliminepyridine compound from the first mixture.

In some embodiments, a method for producing a hexadentate bimetallic complex comprises contacting an acyliminepyridine metal complex and a first amine to form a mixture, and recovering the hexadentate bimetallic complex from the mixture. In embodiments where an acyliminepyridine metal complex is employed in forming a hexadentate bimetallic complex, the acyliminepyridine metal complex may be prepared by contacting a di-acylpyridine with an amine to form a first mixture; recovering an acyliminepyridine compound from the first mixture; contacting the acyliminepyridine compound with a metal salt to form a second mixture; and recovering the acyliminepyridine metal complex from the second mixture. In embodiments, the acyliminepyridine metal complex may be a mono-acyliminepyridine metal complex where the amine is a diamine. The mono-acyliminepyridine metal complex to diamine molar ratio may be in the range of about 2:1.

DETAILED DESCRIPTION OF EMBODIMENTS

The present application discloses hexadentate bimetallic complexes and methods for producing hexadentate bimetallic complexes. Such complexes and methods may involve one or more compounds having the chemical structures shown in Tables 1 through 5:

TABLE 1

Monoamines, Diamines, and Diacylpyridines

H$_2$N—W
Structure 1

H$_2$N—W'
Structure 2

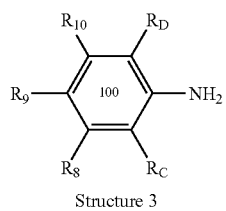

Structure 3

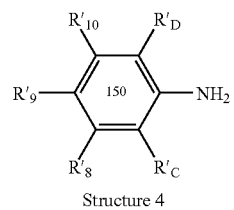

Structure 4

TABLE 1-continued
Monoamines, Diamines, and Diacylpyridines
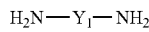
Structure 5
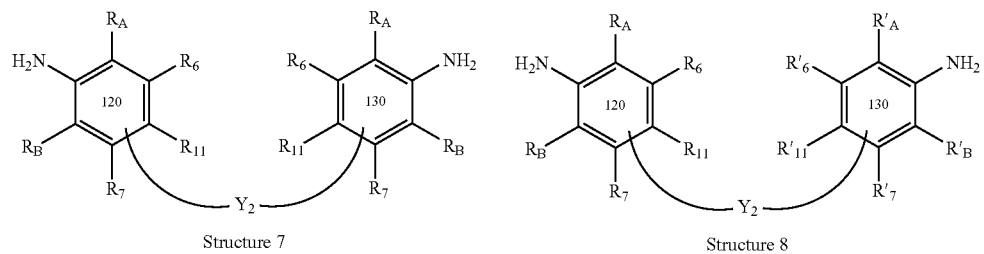
TABLE 2
Acyliminepyridine Compounds
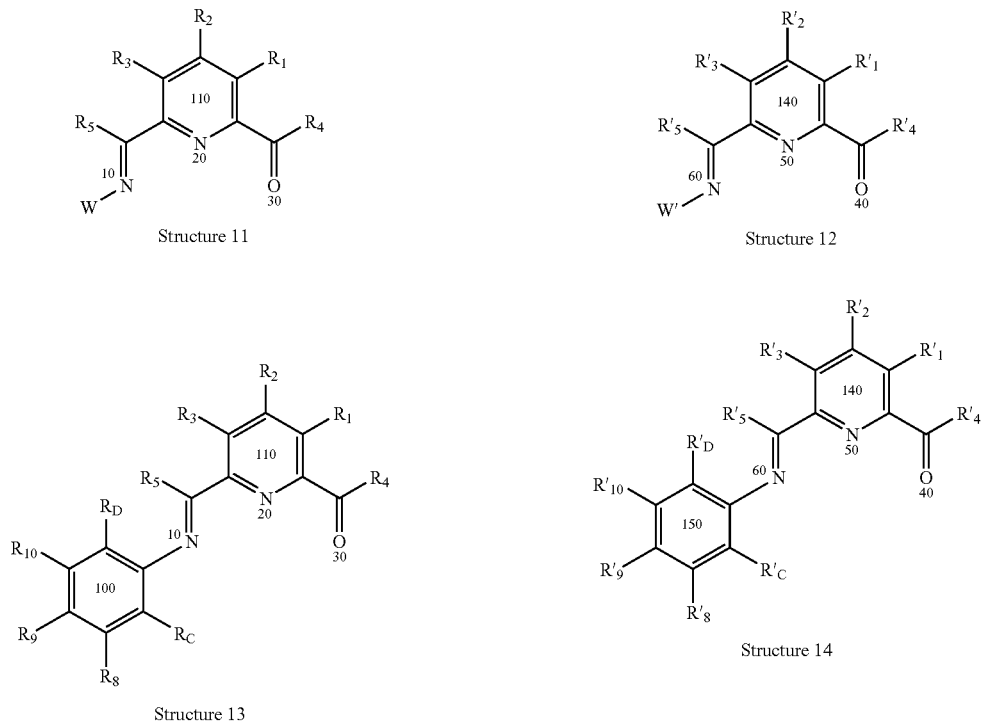

TABLE 2-continued
Acyliminepyridine Compounds
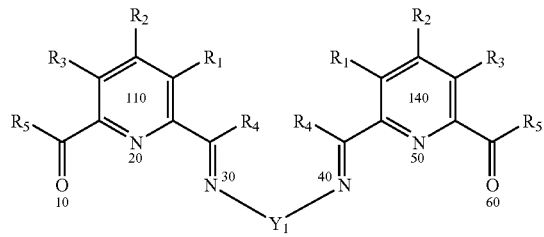
Structure 15
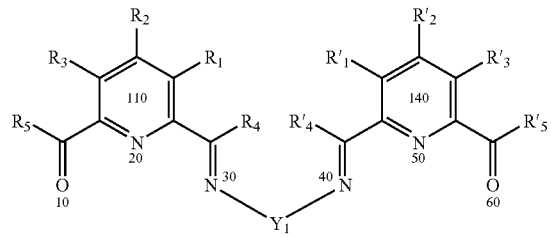
Structure 16
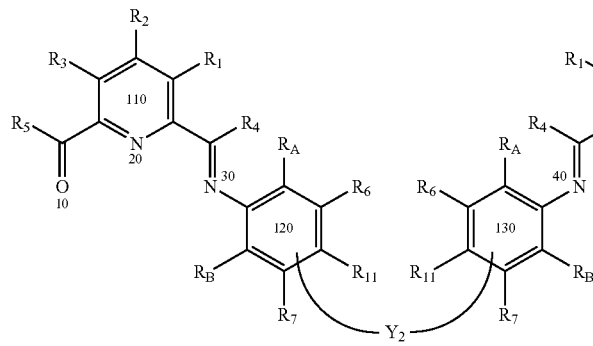
Structure 17
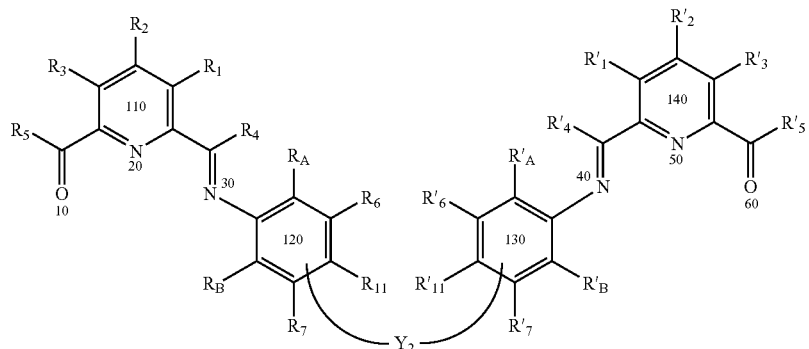
Structure 18
TABLE 3
Acyliminepyridine Metal Complexes
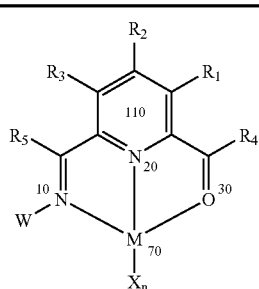
Structure 19
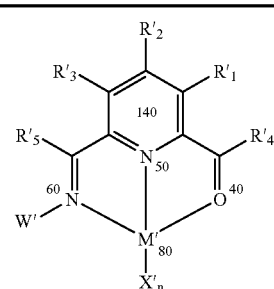
Structure 20

TABLE 3-continued
Acyliminepyridine Metal Complexes
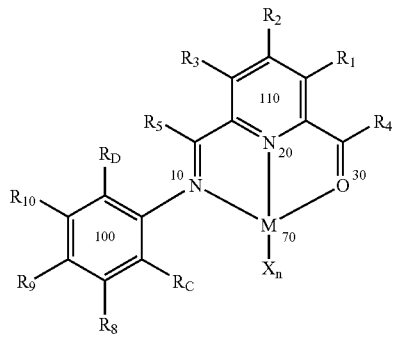
Structure 21
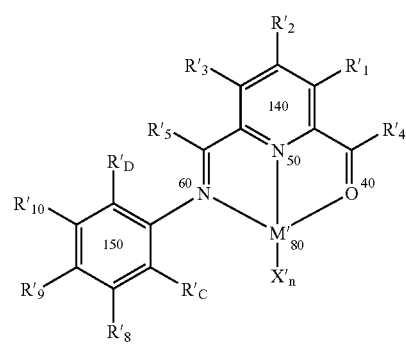
Structure 22
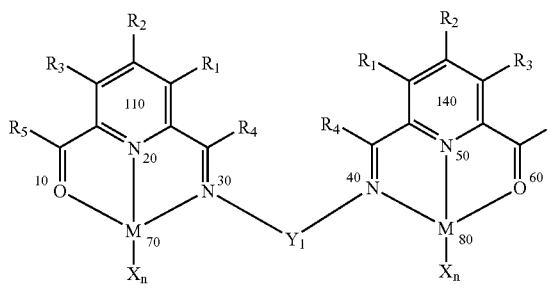
Structure 23
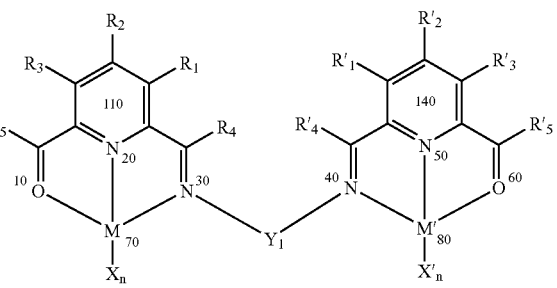
Structure 24
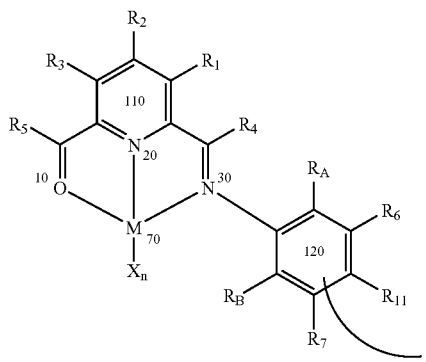
Structure 25
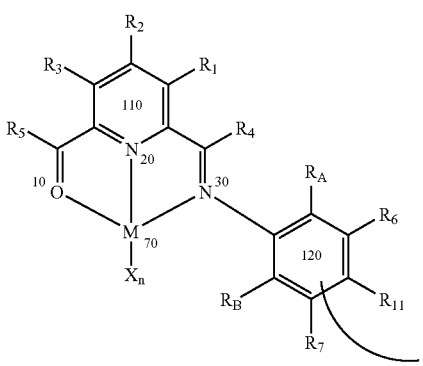
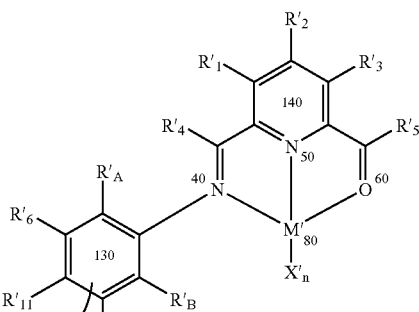
Structure 26

TABLE 4
Hexadentate Bimetallic Complexes
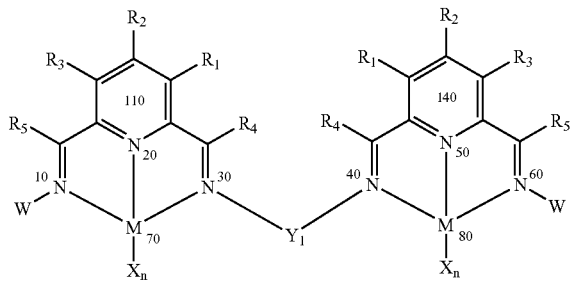
Structure 27
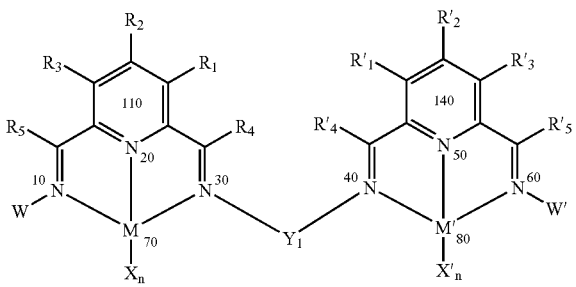
Structure 28
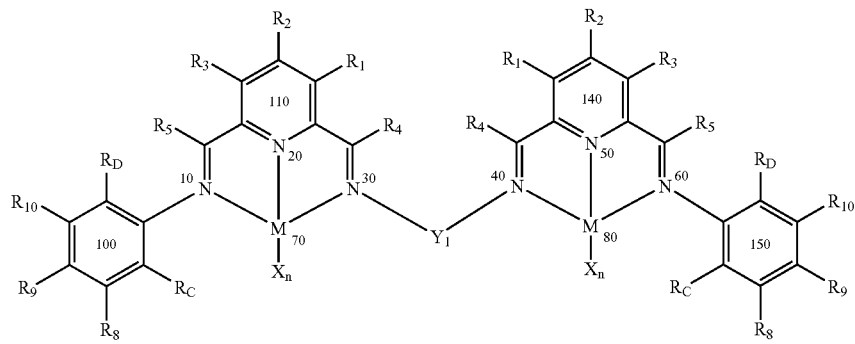
Structure 29
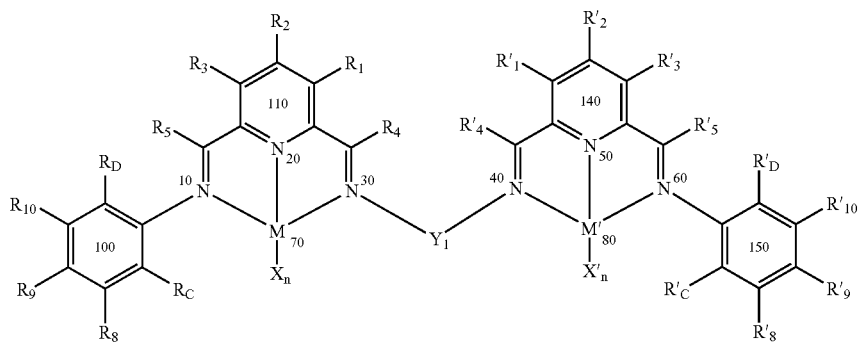
Structure 30

TABLE 4-continued
Hexadentate Bimetallic Complexes
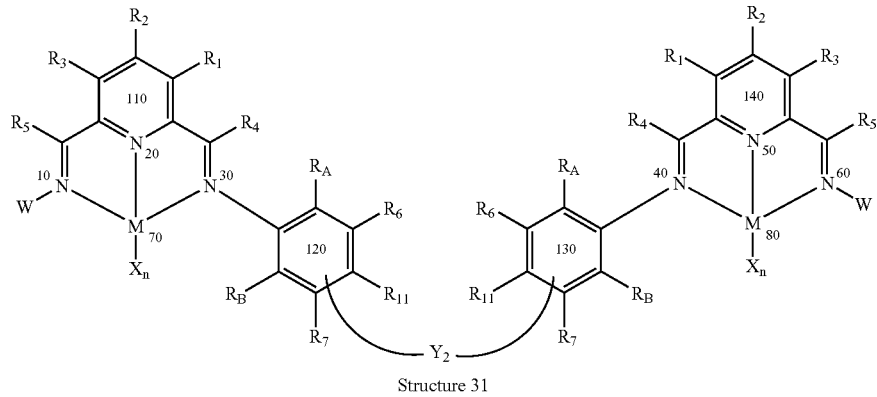
Structure 31
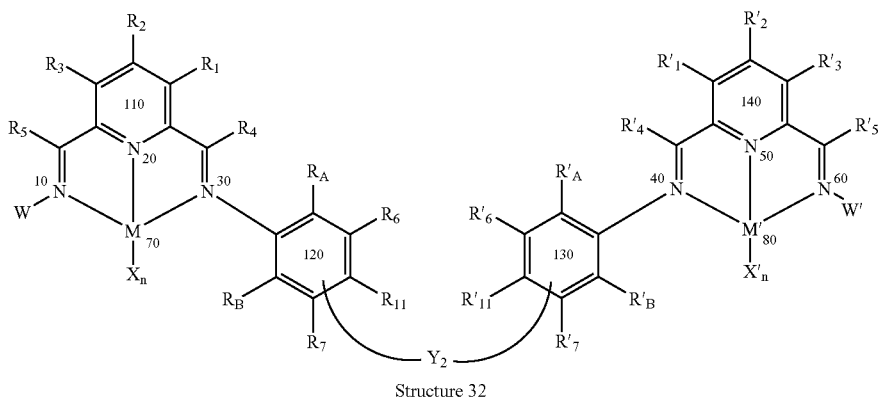
Structure 32
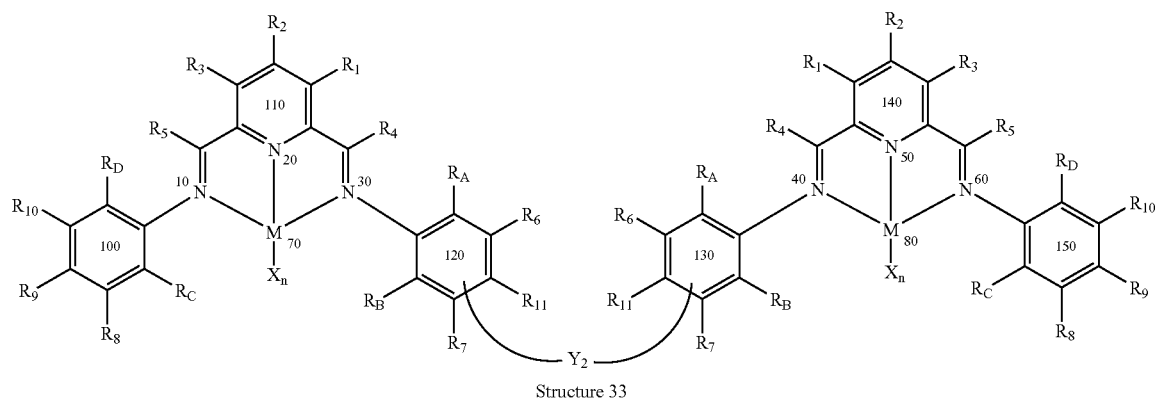
Structure 33

TABLE 4-continued
Hexadentate Bimetallic Complexes
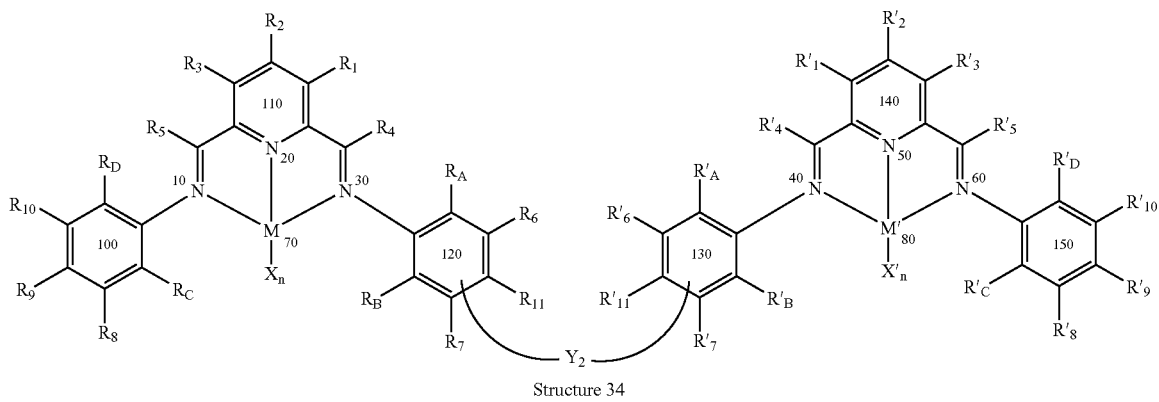
Structure 34
TABLE 5
Hexadentate Ligands
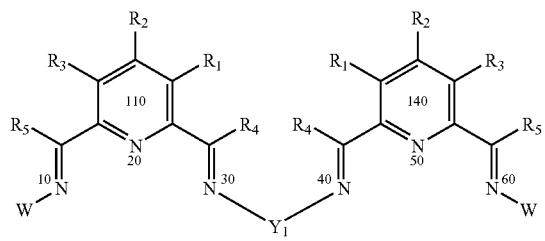
Structure 35
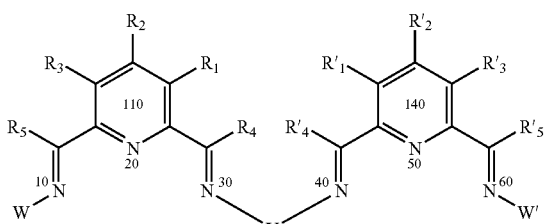
Structure 36
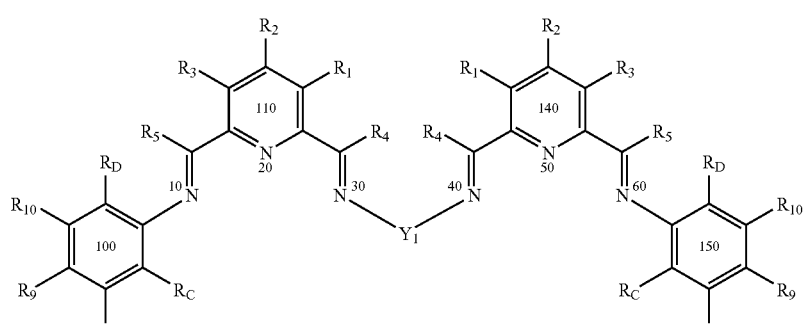
Structure 37

TABLE 5-continued
Hexadentate Ligands
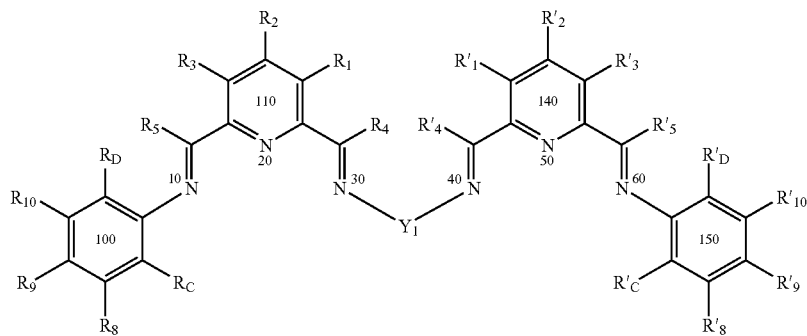
Structure 38
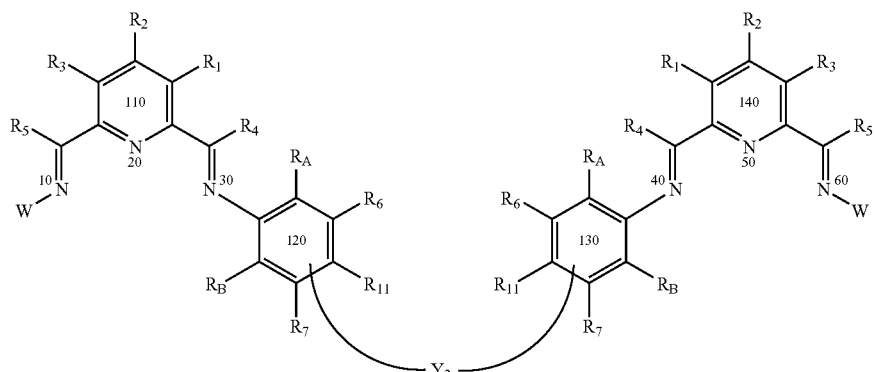
Structure 39
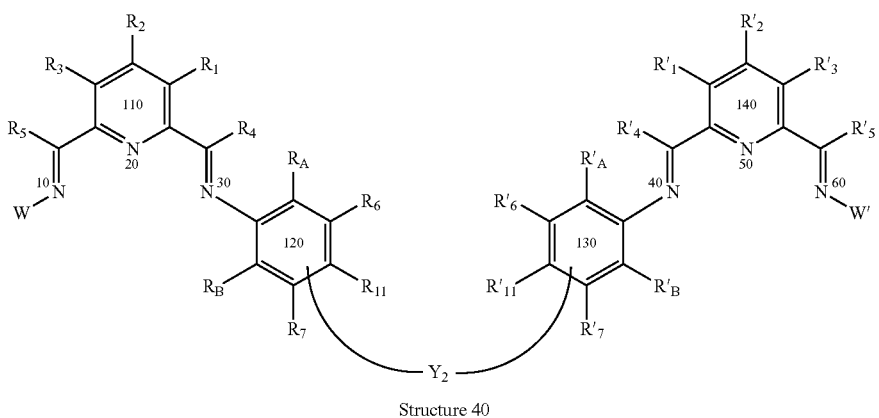
Structure 40

TABLE 5-continued

Hexadentate Ligands

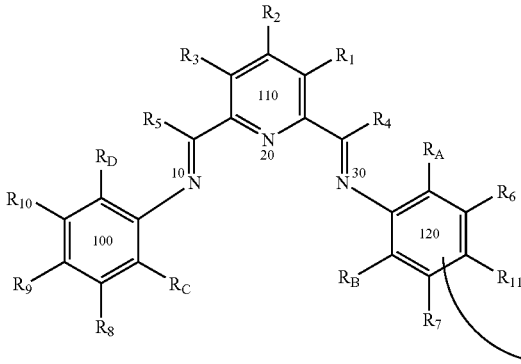

Structure 41

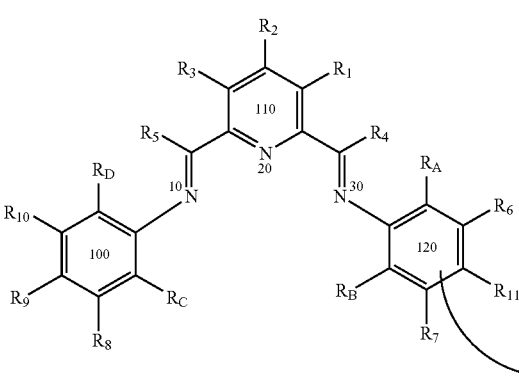

Structure 42

For purposes of explanation only, the chemical compounds shown in Tables 1 through 5 may be divided into three categories: starting materials, intermediates, and complexes. Generally, starting materials react to form intermediates, which may be further reacted to form complexes. In some instances, complexes may also be intermediates. Generally, starting materials may be the monoamines, diamines, and di-acylpyridines of Table 1. The intermediates may include the acyliminepyridine compounds, acyliminepyridine metal complexes, and ligands of Tables 2, 3, and 5. The acyliminepyridine compounds, acyliminepyridine metal complexes, and ligands of Tables 2, 3, and 5 may also be considered starting materials for the production of the hexadentate bimetallic complexes of Table 4.

Also within the tables, relationships, such as generic to specific, are present among structures. For example, the compound of structure 13 is a specific embodiment of the compound of structure 11, and the compound of structure 33 is a specific embodiment of structure 34, etc. Various other specific to generic relationships among structures will be apparent to one skilled in the art. The pendant or "R" groups associated with the compounds, as indicated in Tables 1 through 5, are defined in detail below.

Starting materials include structures 1 through 10 in Table 1. Structures 1 and 2 are monoamine starting materials where W and W' are generic pendent groups as defined herein. Structures 3 and 4 are aromatic monoamines, where an aromatic ring has been substituted for the generic pendent groups W and W' of structure 1 and structure 2, respectively. Structure 5 is a diamine starting material where $Y_1$ is a generic structural bridge linking the two amine groups. Structures 7 and 8 are aromatic diamine starting materials in which two aromatic amine groups connected by a linking group, $Y_2$, have been substituted for the structural bridge, $Y_1$, of structure 5. Structures 9 and 10 are substituted di-acylpyridine starting materials having the substituents $R_1$, $R'_1$, $R_2$, $R'_2$, $R_3$, $R'_3$, $R_4$, $R'_4$, $R_5$, and $R'_5$ as described herein. Such substituted di-acylpyridine starting materials may be contacted with one or more monoamine starting materials, for example the monoamine starting materials of structures 1, 2, 3, and 4, to form acyliminepyridine compound intermediates, such as those of structures 11, 12, 13, and 14. Alternatively, the substituted di-acylpyridine starting material may be contacted with a diamine starting material, for example the diamine starting material of structure 5, 7, or 8, to form acyliminepyridine compound intermediates, such as illustrated by structures 15, 16, 17, and 18.

Intermediates in Table 2 and Table 3 may include acyliminepyridine compounds having structures 11, 12, 13, 14, 15, 16, 17, and 18, and acyliminepyridine metal complexes having structures 19, 20, 21, 22, 23, 24, 25, and 26. The acyliminepyridine compound having structure 13 is a derivative of the acyliminepyridine compound having structure 11 wherein the aromatic group 100 is substituted for W in structure 11. Similarly, the acyliminepyridine compound having structure 18 is a derivative of the acyliminepyridine compound having structure 16 wherein the aromatic diamine group of structure 8 is used as a reagent. Other similar relationships will be apparent to one skilled in the art. In embodiments, the acyliminepyridine metal complexes of structures 19, 20, 21, 22, 23, 24, 25, and 26 may be formed by contacting a metal salt with an acyliminepyridine compound, for example the acyliminepyridine compound of structure 11, 12, 13, 14, 15, 16, 17, or 18. Structures 35, 36, 37, 38, 39, 40, 41, and 42 represent hexadentate ligands formed by various combinations of the di-acylpyridine, monoamine, and diamine starting materials of Table 1. Additional details on the formation of hexadentate ligands having structures 36 and 42, and corresponding bimetallic hexadentate complexes having structures 28 and 34, respectively, are provided in U.S. patent application Ser. No. 10/379,828, referenced previously.

Hexadentate bimetallic complexes may be those having structures 27, 28, 29, 30, 31, 32, 33, and 34 in Table 4. The hexadentate ligand or hexadentate bimetallic complex may be identified by six nitrogen atoms denoted by reference numerals 10, 20, 30, 40, 50, and 60 in hexadentate ligand structures 35, 36, 37, 38, 39, 40, 41, and 42, or in hexadentate bimetallic complex structures 27, 28, 29, 30, 31, 32, 33 and 34. Such hexadentate structures may be viewed as consisting of two halves or sides; one side including nitrogen atoms 10, 20, and 30, and the other side including nitrogen atoms 40, 50, and 60. The two halves may be connected by a structural bridge, such as $Y_1$. Alternatively, the two halves may be connected by two aromatic rings linked by structural bridge, $Y_2$. Additionally, the similarities between the two halves of the ligand or complex may vary. In various instances, the two halves may be mirror images of each other, identical or different, symmetrical or asymmetrical, planar or non-planar. The pendant groups, W, W', $R_n$, and $R'_n$, and linking groups, $Y_1$ and $Y_2$, are further defined below. The metal complexes shown in Table 3 and Table 4 may be identified by the presence of a metal salt (M-$X_n$ or M'-$X'_n$), which is present by coordination reaction with an acyliminepyridine compound or hexadentate ligand. The acyliminepyridine compound may be a mono-acyliminepyridine compound or a bis-iminepyridine compound. The metal salts are designated by reference numerals 70 and 80 on the structures of Table 3 and Table 4. 'Bimetallic' refers to the presence of two M-$X_n$ groups, i.e., one at site 70 and one at site 80. The metal salt at site 70 may be the same as or different than the metal salt at site 80.

As mentioned previously, the metal complexes may be symmetrical or asymmetrical. The asymmetry may be a result of a difference between the terminal W and W' imine groups, differences among one or more of the substituents or the substituent pattern of the terminal imine aromatic rings 100 and 150, differences between the $R_4$ and $R'_4$ groups, differences between the $R_5$ and $R'_5$ groups, differences among one or more of the substituents or the substituent pattern of the pyridine rings 110 and 140, asymmetry in the linking group, $Y_1$, differences among one or more of the substituents or the substituent pattern of the linking aromatic rings 120 and 130, asymmetry in the linking group, $Y_2$, or any combination of differences in these elements. Variations in chemical structure orientation and planarity, such as may occur by rotation of a portion of a structure at a chemical bond, may also affect symmetry. Though technically a point of asymmetry, for the purpose of this discussion a difference in the metal salt at sites 70 and 80 (either at the metal atom or the X groups) may not be considered a difference that affects the symmetry of acyliminepyridine compounds, acyliminepyridine metal complexes, and hexadentate bimetallic complexes. As an example, the link between symmetrical and asymmetrical embodiments may be illustrated where structure 27 represents a symmetrical embodiment of the hexadentate bimetallic complex of structure 28, if $Y_1$ is symmetrical, the terminal imine groups are identical, W and W' are identical, $R_4$ and $R'_4$ groups are identical, $R_5$ and $R'_5$ groups are identical, and the substituents and substituent pattern of the pyridine rings 110 and 140 are identical. Any difference between these combinations of elements would make structure 28 asymmetric. As a further example, structure 33 would represent a symmetrical embodiment of structure 34 where the R' groups of structure 34 are selected to be identical to the R groups, and $Y_2$ is selected to be symmetrical. Structure 29 represents a specific symmetrical embodiment of structure 27 wherein the aromatic rings 100 and 150 are substituted for the W and W' of structure 28. Structure 33 represents a specific symmetrical embodiment of structure 29 wherein the aromatic rings, 120 and 130, and structural bridge, $Y_2$, of structure 34 are substituted for the structural bridge, $Y_1$, of structure 29. Other symmetrical versus asymmetrical relationships among structures in Tables 1 though 5 will be apparent to one skilled in the art.

The components of the chemical structures illustrated in Tables 1 through 5 labeled as $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, $R'_{10}$, $R_{11}$, $R'_{11}$, $R_A$, $R'_A$, $R_B$, $R'_B$, $R_C$, $R'_C$, $R_D$, $R'_D$, W, W', $Y_1$, $Y_2$, M, M', $X_n$, and $X'_n$ (or "'R' groups" or "pendant groups"), are defined throughout the present application. The components may be subdivided into the following groups: Group 1—W and W'; Group 2—$R_1$, $R'_1$; $R_2$, $R'_2$, $R_3$, and $R'_3$; Group 3—$R_4$, $R'_4$, $R_5$, and $R'_5$; Group 4—$R_6$, $R'_6$, $R_7$, $R'_7$, $R_8$, $R'_8$, $R_9$, $R'_9$, $R_{10}$, $R'_{10}$, $R_{11}$ and $R'_{11}$; Group 5—$R_A$, $R'_A$, $R_B$, $R'_B$, $R_C$, $R'_C$, $R_D$, and $R'_D$; Group 6—$Y_1$ and $Y_2$; Group 7—M and M'; and Group 8—$X_n$ and $X'_n$. These groups are independent elements and thus the structures in Tables 1-5 may be defined using any combination of embodiments within each respective group.

In some embodiments, W and W' are each independently hydrogen, hydrocarbyl, substituted hydrocarbyl, or an inert functional group. The applicable inert functional groups are further described herein.

In some embodiments, $R_1$, $R'_1$, $R_2$, $R'_2$, $R_3$, and $R'_3$ are each independently hydrogen, hydrocarbyl, substituted hydrocarbyl, or an inert functional group. In other embodiments, any two of $R_1$, $R'_1$, $R_2$, $R'_2$, $R_3$, and $R'_3$, vicinal to one another, taken together may form a ring. The applicable inert functional groups are further described herein.

In some embodiments, $R_4$, $R'_4$, $R_5$, and $R'_5$ are each independently hydrogen, hydrocarbyl, substituted hydrocarbyl, or an inert functional group. The applicable inert functional groups a further described herein. In some embodiments $R_4$, and $R_1$, or alternatively $R'_4$, and $R'_1$, taken together may form a ring. In other embodiments $R_5$ and $R_3$, or alternatively $R_{15}$ and $R'_3$, taken together may form a ring. In yet other embodiments, $R_4$ and $R_A$ or $R_B$, or alternatively, $R_{14}$ and $R'_A$ or $R'_B$, taken together may form a ring. In yet other embodiments, $R_5$ and $R_C$ or $R_D$, or alternatively, $R'_5$ and $R'_C$ or $R'_D$, taken together may form a ring.

In some embodiments, $R_6$, $R'_6$, $R_7$, $R'_7$, $R_8$, $R'_8$, $R_9$, $R'_9$, $R_{10}$, $R'_{10}$, $R_{11}$ and $R'_{11}$ are each independently hydrogen, hydrocarbyl, substituted hydrocarbyl, or an inert functional group. The applicable inert functional groups are further described herein.

In some embodiments, $R_A$, $R'_A$, $R_B$, $R'_B$, $R_C$, $R'_C$, $R_D$, and $R'_D$, generally ortho to the nitrogen atom group, either amine or imine, are each independently hydrogen, hydrocarbyl, substituted hydrocarbyl, or an inert functional group. The applicable inert functional groups are further described herein. In other embodiments, $R_A$, $R'_A$, $R_B$, $R'_B$, $R_C$, $R'_C$, $R_D$, and $R'_D$, are independently selected from hydrogen, fluorine, an inert functional group, a primary carbon group, a secondary carbon group, or a tertiary carbon group.

$Y_1$ and $Y_2$ typically represent a structural bridge between two halves of a ligand or complex. $Y_1$ may be a bond between nitrogen group 30 and nitrogen group 40, a hydrocarbyl having from about 0 to about 30 carbon atoms, a substituted hydrocarbyl having from about 0 to about 30 carbon atoms, or an inert functional group. $Y_2$ may be a bond between aromatic rings 120 and 130, a hydrocarbyl having from about 0 to about 30 carbon atoms, substituted hydrocarbyl having from about 0 to about 30 carbon atoms, or an inert functional group. In further embodiments, $Y_2$ may be a bond connecting any but the ortho positions of the two aromatic rings, a hydrocarbyl group including from about 0 to about 20 carbon atoms, methylene ($CH_2$), ethylene ($C_2H_4$), or an inert functional group. In some embodiments, the two $R_{11}$ groups, or alternatively the $R_{11}$ and $R'_{11}$ groups, taken together represent the structural bridge $Y_2$. In other embodiments, the two $R_{11}$ groups, or alternatively the $R_{11}$ and $R'_{11}$ groups, taken together form a methylene ($CH_2$), or ethylene ($C_2H_4$) group and represent the structural bridge $Y_2$. In yet other embodiments, $Y_2$ is a bond between the two carbon atoms having the $R_{11}$ or $R'_{11}$ substituents. In some embodiments, any two of $R_4$, $R'_4$, $R_6$, $R'_6$, $R_7$, $R'_7$, $R_B$, $R'_B$, $R_{11}$, $R'_{11}$, $R_C$, $R'_C$, $R_8$, $R'_8$, $R_9$, $R'_9$, $R_{10}$, $R'_{10}$, $R_D$, and $R'_D$, vicinal to one another, taken together may form a ring. In some embodiments, any of $R_4$, $R'_4$, $R_6$, $R'_6$, $R_7$, $R'_7$, $R_B$, $R'_B$, $R_{11}$, $R'_{11}$, $R_C$, $R'_C$, $R_8$, $R'_8$, $R_9$, $R'_9$, $R_{10}$, $R'_{10}$, $R_D$, and $R'_D$ vicinal to $Y_2$, taken together, may form a ring.

In other embodiments, when $R_A/R'_A$ is a primary carbon group, then none, one, or two of $R_B/R'_B$, $R_C/R'_C$, and $R_D/R'_D$ are primary carbon groups, secondary carbon groups, phenyl, substituted phenyl, or inert functional groups, and the remainder of $R_B/R'_B$, $R_C/R'_C$, and $R_D/R'_D$ are hydrogen or fluorine. In another embodiment, when $R_A/R'_A$ is a secondary carbon group, then none, one, or two of $R_B/R'_B$, $R_C/R'_C$, and $R_D/R'_D$ are primary carbon groups, secondary carbon groups, phenyl, substituted phenyl, or inert functional groups, and the remainder of $R_B/R'_B$, $R_C/R'_C$, and $R_D/R'_D$ are hydrogen or fluorine. In other embodiments, when $R_A/R'_A$ is a tertiary carbon group, then none or one of $R_B/R'_B$, $R_C/R'_C$, and $R_D/R'_D$ are tertiary, phenyl, or substituted phenyl, and the remainder are hydrogen or fluorine. In other embodiments, when $R_C/R'_C$ is a primary carbon group, then none, one, or two of $R_A/R'_A$, $R_B/R'_B$, and $R_D/R'_D$ are primary carbon groups, secondary carbon groups, phenyl, substituted phenyl, or inert functional groups, and the remainder of $R_A/R'_A$, $R_B/R'_B$, and $R_D/R'_D$ are hydrogen or fluorine. In other embodiments, when $R_C/R'_C$ is a secondary carbon group, then none, one, or two of $R_A/R'_A$, $R_B/R'_B$ and $R_D/R'_D$ are primary carbon groups, secondary carbon groups, phenyl, substituted phenyl, or inert functional groups, and the remainder of $R_A/R'_A$, $R_B/R'_B$, and $R_D/R'_D$ are hydrogen or fluorine. In other embodiments, when $R_C/R'_C$ is a tertiary carbon group, then none or one of $R_A/R'_A$, $R_B/R'_B$, and $R_D/R'_D$ are tertiary, phenyl, or substituted phenyl, and the remainder of $R_A/R'_A$, $R_B/R'_B$, and $R_D/R'_D$ are hydrogen or fluorine. Independent of the above limitations, $Y_1$ and $Y_2$ may be symmetric or asymmetric.

M and M' may be any metal atom. In some embodiments, M and M' are metal atoms selected from Group VB, VIB, or VIII of the CAS version of the Periodic Table. In other embodiments, M and M' may be metal atoms having a +3 oxidation state. In other embodiments, M and M' may be cobalt, iron, nickel, chromium, vanadium, or mixtures thereof. In further embodiments, M and M' may be cobalt, iron, chromium, vanadium, or mixtures thereof. In further embodiments, M and M' may be cobalt, iron, or mixtures thereof. In further embodiments, M and M' may be iron. In further embodiments, M and M' may be cobalt. In further embodiments, M and M' may be chromium. In further embodiments, M and M' may be nickel.

X and X' may independently be any anion. In some embodiments, X and X' are independently a halide or acetyl acetonate. In some embodiments X and X' are halides. In further embodiments the halide is selected from chlorine, bromine, and iodine. In some embodiments the halide is chloride. In yet other embodiments the halide is bromide. The number, n, of X groups is such that the total number of negative charges on the total number X or X' anion equals the oxidation state of M or M' respectively. In some embodiments, n is 1, 2, or 3 and the total number of negative charges on X or X' is equal to the oxidation state of M or M', respectively. In some embodiments X may be an anion, such as a halide or acetyl acetonate, so that the total number of negative charges on X is equal to the oxidation state of M or M'.

In an embodiment of the hexadentate bimetallic complex 33, $R_A$ and $R_B$ are hydrogen; and $R_C$ and $R_D$ are each independently methyl, ethyl, propyl, or isopropyl. In an embodiment, $R_A$ and $R_B$ are methyl; and $R_C$ and $R_D$ are each independently methyl, ethyl, propyl, or isopropyl. In an embodiment, $R_C$ and $R_D$ are hydrogen; and $R_A$ and $R_B$ are each independently methyl, ethyl, propyl, or isopropyl. In an embodiment, $R_C$ and $R_D$ are methyl; and $R_A$ and $R_B$ are each independently methyl, ethyl, propyl, or isopropyl. In an embodiment, $R_A$ and $R_D$ are hydrogen; and $R_B$ and $R_C$ are each independently methyl, ethyl, propyl, or isopropyl. In an embodiment, $R_A$ and $R_D$ are methyl; and $R_B$ and $R_C$ are each independently methyl, ethyl, propyl, or isopropyl. The embodiments of this paragraph also apply to the amine, acyliminepyridine compounds, and acyliminepyridine metal complexes used to prepare hexadentate bimetallic complex 33.

In some embodiments, Ra, Rb, R'a, and R'b are selected such that each M has an asymmetric environment with respect to the ortho positions on rings 100 and 120. In further embodiments, Ra, Rb, R'a, and R'b are selected such that each M has an asymmetric environment with respect to the ortho positions on rings 100 and 120 in the hexadentate bimetallic complex having structure 34. The embodiments of this paragraph also apply to the amine, acyliminepyridine compounds, and acyliminepyridine metal complexes used to prepare hexadentate bimetallic complex 34.

In an embodiment of a hexadentate bimetallic complex 27, 28, 29, 30, 31, 32, 33, or 34, the pendant groups may be as defined above, except that both M and M' are cobalt. In another embodiment, both M and M' are iron. In another embodiment, one of the metal atoms, M or M', is iron, and the other is cobalt. In another embodiment, selection of M and M' affects selection of $R_A$, $R_B$, $R_C$, $R_D$, W, and $Y_1$.

In an embodiment of a hexadentate bimetallic complex 33, pendant groups may be as defined above, with the following exceptions:

$R_1$, $R_2$, and $R_3$ are hydrogen;

$R_4$ and $R_5$ are methyl or hydrogen;

$R_6$, $R_7$, $R_8$, $R_9$, and $R_{10}$ are hydrogen;

$R_A$, $R_B$, $R_C$, and $R_D$ are each independently methyl, ethyl, propyl, or isopropyl; and the two $R_{11}$ groups taken together represent the structural bridge $Y_2$.

The embodiments of this paragraph also apply to the amines, di-acylpyridines, acyliminepyridine compounds, and acyliminepyridine metal complexes used to prepare hexadentate bimetallic complex 34.

For purposes of this application, an acyl group is represented by the structure RC(=O)—, wherein R may be hydrogen, a hydrocarbyl group, or a substituted hydrocarbyl group.

For purposes of this application, a hydrocarbyl group is a group containing only carbon and hydrogen. If not otherwise stated, it is preferred that hydrocarbyl groups herein contain 1 to about 30 carbon atoms. The terms "hydrocarbyl" and "alkyl" are equivalent, and may be used interchangeably.

For purposes of this application, a substituted hydrocarbyl is a hydrocarbyl group which contains one or more substituent groups which are inert under the process conditions to which the compound containing these groups is subjected. The substituent groups also do not substantially interfere with the hexadentate bimetallic complex preparation process. If not otherwise stated, it is preferred that substituted hydrocarbyl groups herein contain from about 1 to about 30 carbon atoms. Included in the meaning of "substituted" are aromatic and/or heteroaromatic rings.

For purposes of this application, an inert functional group is a group, other than hydrocarbyl or substituted hydrocarbyl, which does not substantially interfere with any process described herein where the compound in which it is present takes part. Examples of inert functional groups include halo (fluoro, chloro, bromo and iodo), or ethers such as —$OR_{18}$ wherein $R_{18}$ is hydrocarbyl or substituted hydrocarbyl. In cases in which the functional group may be near a metal atom, such as $R_4$, $R_5$, $R_8$, $R_B$, $R_C$, $R_D$, $R'_4$, $R'_5$, $R'_8$, $R'_B$, $R'_C$, and $R'_D$ the functional group should not coordinate to the metal atom more strongly than the groups in compounds containing $R_4$, $R_5$, $R_8$, $R_B$, $R_C$, $R_D$, $R'_4$, $R'_5$, $R'_8$, $R'_B$, $R'_C$, and $R'_D$ which are shown as coordinating to the metal atom, that is they should not displace the desired coordinating group.

For purposes of this application, a primary carbon group includes a group of the formula —$CH_2$—, wherein the free valence is to any other atom (the bond represented by the hyphen is to the benzene ring to which the primary carbon group is attached). Thus, the free valence may be bonded to a hydrogen atom, halogen atom, carbon atom, oxygen atom, sulfur atom, etc. In other words, the free valence may be to hydrogen, hydrocarbyl, substituted hydrocarbyl or a functional group. Examples of primary carbon groups include—$CH_3$, —$CH_2CH(CH_3)_2$, —$CH_2Cl$, —$CH_2C_6H_5$, and —$CH_2OCH_3$.

For purposes of this application, a secondary carbon group includes a group of the formula —CH=, wherein the free valences are to any other atoms (the bond represented by the hyphen is to the benzene ring to which the secondary carbon group is attached). Thus, the free valences may be bonded to a halogen atom, carbon atom, oxygen atom, sulfur atom, etc. In other words, the free valences may be to a hydrocarbyl, a substituted hydrocarbyl or a functional group. Specific examples of secondary carbon groups include —$CH(CH_3)_2$, —$CHCl_2$, —$CH(C_6H_5)_2$, cyclohexyl, —$CH(CH_3)OCH_3$, and —CH=$CHCH_3$.

For purposes of this application, a tertiary carbon group includes a group of the formula —C≡, wherein the free valences are to any other atoms. Thus, the free valences may be bonded to a halogen atom, carbon atom, oxygen atom, sulfur atom, etc. In other words, the free valences may be to a hydrocarbyl, a substituted hydrocarbyl or a functional group. Examples of tertiary carbon groups include: —$C(CH_3)_3$, —$C(C_6H_5)_3$, —$CCl_3$, —$C(CH_3)_2OCH_3$, —C≡CH, —$C(CH_3)CH=CH_2$, $C_6H_5$, $CF_3$, and 1-adamantyl.

For purposes of illustration, some of the complexes and intermediates exemplified in Tables 2 through 5 may be viewed as consisting of two halves or sides. One side, such as in structures 7, 8, 15, 16, 17, 18, 23, 24, 25, 26, 27, 28, 29, 30, 31, 32, 33, 34, 35, 36, 37, 38, 39, 40, 41, and 42, may include oxygen or nitrogen groups at locations 10, 20, and 30, and the other side may include oxygen or nitrogen groups at locations 40, 50, and 60. The two sides in structures 7, 8, 15, 16, 17, 18, 23, 24, 25, 26, 27, 28, 29, 30, 31, 32, 33, 34, 35, 36, 37, 38, 39, 40, 41, and 42 may be connected by a structural bridge, $Y_1$ or $Y_2$.

Some of the complexes and intermediates shown in Tables 2 through 5 may be further illustrated by referring to rings labeled 100, 110, 120, 130, 140, and 150, such as in structures 3, 4, 7, 8, 9, 10, 13, 14, 15, 16, 17, 18, 23, 24, 25, 26, 27, 28, 29, 30, 31, 32, 33, 34, 35, 36, 37, 38, 39, 40, 41, and 42. Some of these compounds and complexes may be viewed as having two halves or sides. One half of such structures may include some or all of rings 100, 110, and 120, and the other side may include some or all of rings 130, 140, and 150. The two halves may be connected by a structural bridge, such as $Y_1$ or $Y_2$.

In some embodiments, one side of a structure identified by groups attached at some or all of the locations 10, 20, and 30, and/or by some or all of rings 100, 110, and 120, is a mirror image of the other half of the structure identified by groups attached at some or all of the locations 40, 50, and 60, and/or some or all of rings 130, 140, and 150. In such a mirror image scenario, the two halves or sides of the structure may be divided by a mirror plane, which passes through a symmetrical structural bridge, such as $Y_1$ or $Y_2$. In some embodiments involving $Y_2$ as a structural bridge, $Y_2$ may connect rings 120 and 130 at their respective meta or para positions. In other embodiments, $R_7$, $R'_7$, $R_6$, $R'_6$, $R_{11}$, and/or $R'_{11}$ may form part of the structural bridge, $Y_2$. In other embodiments, a structure may have symmetry such that the 'R', and/or the 'W' groups are symmetrical on each half of the structure, but the sides of the structure may not be mirror images of one another, such as when divided by a mirror plane. In yet other embodiments, the 'R', and/or the 'W' groups on each side of a structure are independent of each other such that the structure may be asymmetrical. Considering structure 36, for example, $R_1$, $R'_1$, $R_2$, $R'_2$, $R_3$, $R'_3$, $R_4$, $R'_4$, W, and W' may all be selected independently of each other. Further, in various embodiments, the degree of symmetry present in such asymmetrical structures may vary.

Symmetry, for purposes of the present disclosure, is defined as when each $R_n$ substituent is identical to each $R'_n$ substituent, for example according to structure 34, where $R'_7$ may have the same structure as $R_7$. In the more general structure 28, W may have the same structure as W'.

Even though compounds 34 and 28 may possess symmetry according to the cited definition, compounds of this type may possess local asymmetry. Local asymmetry is defined by considering the ortho groups $R_A$, $R_B$, $R_C$, and $R_D$, along with their potentially identical ortho groups $R'_A$, $R'_B$, $R'_C$, and $R'_D$, for example in complex 34. Local asymmetry refers to asymmetry of the ortho groups around the metal on each half of compound 34, and it occurs when the type and number of substituents in $R_A$ and $R_B$ is not identical to the type and number of substituents in $R_C$ and $R_D$. For example if $R_A$ and $R_B$ are both methyl, and $R_C$ and $R_D$ are both H, then local asymmetry is present.

Thus, those of skill in the art will comprehend that a plurality of structural embodiments are possible because of various symmetrical and asymmetrical combinations of '$R_n$' groups, 'W' groups, M-$X_n$ groups, structural bridges, orientations, and rotations.

Those of skill in the art will recognize the relationships among starting materials, intermediates, and complexes that motivate the selection of synthesis paths necessary to achieve various possible embodiments of hexadentate bimetallic complexes suitable for employment in a polymerization catalyst system. For example, structures 27 and 30 are specific embodiments formed by substitutions of structure 28. Structure 28 includes $R_n$ groups on one side and $R'_n$ groups on the other, which may indicate either identical or different substituents on each half of the structure. Starting materials necessary to form an asymmetrical embodiment having structure 28 may yield both symmetrical and asymmetrical complexes. The two sides of structure 27, on the other hand, are symmetrical, having $R_1$ through $R_5$ on both sides of the complex. Such a symmetrical complex may be a part of a mixture of symmetrical and asymmetrical complexes, or starting materials may be selected such that the synthesis only yields symmetrical complexes.

Another example that illustrates the relationships among starting materials, intermediates, and complexes is structure 19. Of the intermediate complexes in Table 3, structures 19 and 20 are the most generic intermediate complexes that may be employed to achieve the higher complexes including those in Table 4.

Amid other considerations, recognizing the relationships among starting materials, intermediates, and complexes assists in selecting starting materials to produce a desired symmetry in a resulting mixture of complexes. For example, two different di-acylpyridines having structure 9 may be selected in order to produce a mixture of hexadentate bimetallic complexes that includes some complexes that are asymmetrical with regard to pendant groups $R_1$ through $R_5$. Employing only one type of di-acylpyridine having structure 9 may produce a batch of hexadentate bimetallic complexes that are all symmetrical with respect to pendant groups $R_1$ through $R_5$. Similarly, two different aromatic monoamines having structure 3 may be selected in order to produce a mixture of hexadentate bimetallic complexes that includes some complexes that are asymmetrical with regard to pendant groups $R_C$, $R_D$, $R_8$, $R_9$, and $R_{10}$. Thus, a plethora of synthesis paths employing various combinations of starting materials and intermediates may achieve a corresponding multiplicity of hexadentate structures suitable for employment in a polymerization catalyst system.

One starting material for producing a hexadentate bimetallic complex is an amine. The amine may have structures 1, 2, 3, 4, 5, 7, or 8 as indicated in Table 1. Generally the amine may be a monoamine, an aromatic monoamine, a diamine, an aromatic diamine, or combinations thereof. In some embodiments the amine is a monoamine. In further monoamine embodiments, the monamine has structure 1, 2, 3, 4, or mixtures thereof; alternatively, structures 1, 2, or mixtures thereof; alternatively, structures 3, 4, or mixtures thereof; alternatively, structure 1; or alternatively, structure 3. In some embodiments, the amine is a diamine. In further diamine embodiments, the diamine has structure 5, 7, 8, or mixtures thereof; alternatively, structure 7, 8, or mixtures thereof; alternatively, structure 5; or alternatively structure 7.

A second common base material for producing the hexadentate bimetallic complex is a di-acylpyridine. The di-acylpyridine may have structure 9 or structure 10 as indicated in Table 1. In some embodiments the di-acylpyridine may have structure 9, 10, or mixtures thereof. Alternatively, the di-acylpyridine may have structure 9.

Common intermediates in the disclosed methods of producing a hexadentate bimetallic complex are acyliminepyridine compounds. Acyliminepyridine compounds may have the structures indicated in Table 2. In embodiments, an acyliminepyridine compound may be prepared by contacting a di-acylpyridine with an amine to form a first mixture, and recovering the acyliminepyridine compound from the first mixture. Generally, the amine may be any amine or combination of amines described herein, such as mono-amines, diamines, or combinations thereof. The acyliminepyridine compound may be either a mono-acyliminepyridine compound or a bis-acyliminepyridine compound. Mono-acyliminepyridine compounds generally have one acyl group, one imine group, and one pyridine group while bis-acyliminepyridine compounds have two acyl groups, two imine groups and two pyridine groups. The bis-acyliminepyridine compound may have two halves with one acyl group, one imine group, and one pyridine group in each half connected by a structural bridge $Y_1$ or $Y_2$.

Mono-acyliminepyridine compounds may have structures 11, 12, 13, and 14. In further mono-acyliminepyridine compound embodiments, the mono-acyliminepyridine compound may have structures 11, 12, 13, 14, or mixtures thereof; alternatively, structures 11, 12, or mixtures thereof; alternatively, structures 13, 14, or mixtures thereof; alternatively, structure 11; alternatively, structure 12; alternatively, structure 13; or alternatively, structure 14. In embodiments, a mono-acyliminepyridine compound may be prepared by contacting a monoamine with a di-acylpyridine to form a first mixture, and recovering the mono-acyliminepyridine compound from the first mixture. Monoamines may have structures as described herein. The di-acylpyridines may have structures as described herein. As a non-limiting example, the mono-acyliminepyridine compound having structure 13 may be formed via a reaction between a di-acylpyridine having structure 9 and a monoamine having structure 3. In some embodiments, a mono-acyliminepyridine compound is produced by employing a di-acylpyridine to monoamine molar ratio ranging from about 1:1.1 to about 1:0.75; alternatively, from about 1:1.05 to about 1:0.85; or alternatively, from about 1:1.02 to about 1:0.9. In other embodiments, the di-acylpyridine to monoamine molar ratio may be about 1:1, or alternatively greater than 1:1.

Bis-acyliminepyridine compounds may have structures 15, 16, 17, and 18. In further bis-acyliminepyridine embodiments, the bis-acyliminepyridine may have structures 15, 16, 17, 18, or mixtures thereof; alternatively, structures 15, 16, or mixtures thereof; alternatively, structures 17, 18, or mixtures thereof; alternatively, structure 15; alternatively, structure 16; alternatively, structure 17; or alternatively, structure 18. In embodiments, a bis-acyliminepyridine compound may be prepared by contacting a diamine with a di-acylpyridine to form a first mixture, and recovering the bis-acyliminepyridine compound from the first mixture. The diamines may have structures as described herein. The di-acylpyridines may have structures as described herein. As a non-limiting example, the bis-acyliminepyridine compound having structure 17 may be formed via a reaction between a di-acylpyridine having structure 9 and a diamine having structure 7. In some embodiments, the di-acyliminepyridine is produced at a di-acylpyridine to diamine molar ratio ranging from about 2:1.2 to about 2:0.75; alternatively, from about 2:1.1 to about 2:0.85; or alternatively, from about 2:1.05 to about 2:0.9. In other embodiments, the di-acylpyridine to diamine molar ratio may be about 2:1; or alternatively, more than about 2:1.

Common intermediates and starting materials for some of the disclosed methods of producing a hexadentate bimetallic complex are acyliminepyridine metal complexes. Acyliminepyridine metal complexes may have the structures indicated in Table 3. A variety of methods of preparing acyliminepyridine metal complexes may be employed. In embodiments, an acyliminepyridine metal complex may be formed by contacting an acyliminepyridine compound and a metal salt. Generally the acyliminepyridine compound may be any acyliminepyridine compound or combination of acyliminepyridine compounds as described herein. In certain embodiments, an acyliminepyridine metal complex may be prepared by contacting a di-acyliminepyridine with an amine to form a first mixture; recovering an acyliminepyridine compound from the first mixture; contacting the acyliminepyridine compound with a metal salt to form a second mixture; and recovering the acyliminepyridine metal complex from the second mixture. The acyliminepyridine metal complex may be either a mono-acyliminepyridine metal complex or a bis-acyliminepyridine metal complex. Mono-acyliminepyridine metal complexes generally have one acyl group, one imine group, and one pyridine group. Bis-acyliminepyridine metal complexes have two acyl groups, two imine groups and two pyridine groups wherein the bis-acyliminepyridine metal complex has two halves with one acyl group, one imine group, and one pyridine group in each half, connected by a structural bridge, $Y_1$ or $Y_2$.

Mono-acyliminepyridine metal complexes may have structures 19, 20, 21, or 22. In further mono-acyliminepyridine metal complex embodiments, the mono-acyliminepyridine may have structures 19, 20, 21, 22, or mixtures thereof; alternatively, structures 19 or 20, or mixtures thereof; alternatively, structures 21 or 22, or mixtures thereof; alternatively, structure 19; alternatively, structure 20; alternatively, structure 21; or alternatively, structure 22.

In some embodiments, forming a mono-acyliminepyridine metal complex comprises contacting a mono-acyliminepyridine compound with a metal salt. In a further embodiment the mono-acyliminepyridine metal complex is recovered from the mixture. In yet a further embodiment, the mono-acyliminepyridine complex may be purified using methods known to those skilled in the art, such as recrystallization. As a non-limiting example, the mono-acyliminepyridine metal complex having structure 21 is formed by contacting a mono-acyliminepyridine compound having structure 13 and a metal salt. Additional mono-acyliminepyridine metal complexes, mono-acyliminepyridine compounds and metal salts are described herein. In some embodiments, a mono-acyliminepyridine metal complex is produced employing a mono-acyliminepyridine compound to metal salt molar ratio ranging from about 1:1.25 to about 1:0.75; alternatively, from about 1:1.15 to about 1:0.85; or alternatively, from about 1:1.1 to about 1:0.9. In other embodiments, the mono-acyliminepyridine compound to metal salt molar ratio may be about 1:1.

In other embodiments, a mono-acyliminepyridine metal complex is prepared by contacting a di-acylpyridine with a monoamine to form a mono-acyliminepyridine compound in a mixture, and then contacting a metal salt with the mixture. In further embodiments the mono-acyliminepyridine metal complex is recovered from the mixture. In yet a further embodiment, the mono-acyliminepyridine complex may be purified using methods known to those skilled in the art, such as recrystallization. As a non-limiting example, the mono-acyliminepyridine metal complex having structure 21 is formed by contacting a di-acylpyridine having structure 9 with a monoamine having structure 3 to form a mono-acyliminepyridine compound having structure 13 and then contacting a metal salt with the mixture. The di-acylpyridine to monoamine molar ratios that may be used to form the mixture are provided herein. In some embodiments, a mono-acyliminepyridine metal complex is produced employing a di-acylpyridine to metal salt molar ratio ranging from about 1:1.1 to about 1:0.75; alternatively, from about 1:1.05 to about 1:0.85; or alternatively, from about 1:1.02 to about 1:0.9. In other embodiments, the di-acylpyridine to metal salt molar ratio may be about 1:1. In some embodiments, a mono-acyliminepyridine metal complex is produced employing a monoamine to metal salt molar ratio ranging from about 1:1.25 to about 1:0.75; alternatively, from about 1:1.15 to about 1:0.85; or alternatively, from about 1:1.1 to about 1:0.9. In other embodiments, the monoamine to metal salt molar ratio may be about 1:1. The mono-acyliminepyridine compound to metal salt molar ratio may be about 1:1.

Bis-acyliminepyridine metal complexes may have structures 23, 24, 25, and 26. In further bis-acyliminepyridine metal complex embodiments, a bis-acyliminepyridine compound may have structures 23, 24, 25, 26, or mixtures thereof; alternatively, structures 23 or 24 or mixtures thereof; alternatively, structures 25 or 26, or mixtures thereof; alternatively, structure 23; alternatively, structure 24; alternatively, structure 25; or alternatively, structure 26.

In an embodiment, a bis-acyliminepyridine metal complex is formed by contacting a bis-acyliminepyridine compound with a metal salt. In a further embodiment, the bis-acyliminepyridine metal complex is recovered from the mixture. In yet a further embodiment, the bis-acyliminepyridine complex may be purified using methods known to those skilled in the art, such as recrystallization. As a non-limiting example, the bis-acyliminepyridine metal complex having structure 23 is formed by contacting a bis-acyliminepyridine compound having structure 15 and a metal salt. Additional bis-acyliminepyridine metal complexes, bis-acyliminepyridine compounds, and metal salts are described herein. In some embodiments, the bis-acyliminepyridine metal salt is produced at a bis-acyliminepyridine compound to metal salt molar ratio ranging from about 1:2.5 to about 1:1.6; alternatively, ranging from about 1:2.25 to about 1:1.8; or alternatively, from about 1:2.1 to about 1:1.9. In other embodiments, the bis-acyliminepyridine compound to metal salt molar ratio may be about 1:2.

In a second method for producing a bis-acyliminepyridine metal complex, the method comprises contacting a di-acylpyridine with a diamine to form a bis-acyliminepyridine compound in a mixture and then contacting a metal salt with the mixture. In a further embodiment the bis-acyliminepyridine metal complex is recovered from the mixture. In yet a further embodiment, the bis-acyliminepyridine complex may be purified using methods known to those skilled in the art, such as recrystallization. As a non-limiting example, the bis-acyliminepyridine metal complex having structure 23 is formed by contacting a di-acylpyridine having structure 9 with a diamine having structure 5 to form a bis-acyliminepyridine compound having structure 15 and then contacting a metal salt with the mixture. The di-acylpyridine to diamine molar ratios that may be used to form the mixture are provided herein. In some embodiments, a bis-acyliminepyridine metal complex is produced employing a di-acylpyridine to metal salt molar ratio ranging from about 1:1.25 to about 1:0.75; alternatively, from about 1:1.15 to about 1:0.85; or alternatively, from about 1:1.1 to about 1:0.9. In other embodiments, the di-acylpyridine to metal salt molar ratio may be about 1:1. In some embodiments, a bis-acyliminepyridine metal complex is produced employing a diamine to metal salt molar ratio ranging from about 1.2:2 to about 0.75:2; alternatively, from about 1.1:2 to about 0.85:2; or alternatively, ranging from about 1.05:2 to about 0.9:2. In other embodiments, the diamine to metal salt molar ratio may be about 1:2.

In some embodiments, a hexadentate bimetallic complex is produced by forming at least one imine bond in the presence of a metal salt, metal complex, or combinations thereof. In other embodiments the hexadentate bimetallic complex is produced by forming at least one imine bond in the presence of a metal salt. In further embodiments the hexadentate bimetallic complex is produced by forming at least one imine bond in the presence of a metal complex. In some embodiments, the metal complex is an acyliminepyridine metal complex as described herein. The hexadentate bimetallic complex formed and the specific imine bond or imine bonds formed are independent elements and thus the embodiments of each element described herein may be used to further describe the multiple synthesis methods disclosed herein that a skilled artisan can utilize to produce the hexadentate bimetallic complexes.

In embodiments, the hexadentate bimetallic complex has structure 27, 28, 29, 30, 31, 32, 33, 34, or combinations thereof. In other embodiments, the hexadentate bimetallic complex has structure 28, 30, 32, or 34. In an embodiment, the hexadentate bimetallic complex has structure 28; alternatively, structure 30; alternatively, structure 32; or alternatively, structure 34. In other embodiments, the hexadentate bimetallic complex has structures 27, 29, 31, or 33. In an embodiment, the hexadentate bimetallic complex has structure 27; alternatively, structure 29; alternatively, structure 31; or alternatively, structure 33. In other embodiments, the hexadentate bimetallic complex has structure 27 or 28, or mixtures thereof; alternatively, structure 29 or 30, or mixtures thereof; alternatively, structure 31 or 32, or mixtures thereof; or alternatively structure 33 or 34, or mixtures thereof.

An imine bond may be identified by a nitrogen atom located at position 10, 30, 40, and/or 60 that is attached to a carbon atom by a double bond. In some embodiments, at least one imine bond is identified by one or more imine nitrogen at location(s) 10, 30, 40, or 60. Such bonds may be formed in the presence of a metal salt or metal complex. In other embodiments, at least one imine bond is identified by an imine nitrogen at location 40 and 60 and is formed in the presence of a metal salt or metal complex. In yet other embodiments, at least one imine bond is identified by an imine nitrogen at location 10 and 30 and is formed in the presence of a metal salt or metal complex. In further embodiments, an imine bond is identified by an imine nitrogen at location 10 and 60 and is formed in the presence of a metal salt or metal complex. In still further embodiments, an imine bond is identified by an imine nitrogen at location 30 and 40 and is formed in the presence of a metal salt or metal complex. Additionally, the skilled artisan will recognize which imine bonds may be formed within each described method of producing a hexadentate bimetallic complex described herein.

Various synthesis paths may be employed to produce a hexadentate bimetallic complex by forming at least one imine bond in the presence of a metal salt. In some embodiments, a hexadentate bimetallic complex is produced by contacting an acyliminepyridine compound, a metal salt, and an amine to form a mixture, and recovering the hexadentate bimetallic complex from the mixture. In further embodiments the hexadentate bimetallic complex may be purified using method known to those skilled in the art, such as recrystallization. In some embodiments, a mono-acyliminepyridine compound is contacted with a diamine in the presence of a metal salt. The mono-acyliminepyridine compound, diamine, and metal salt may have structures as described herein. Additionally, suitable molar ratios of the reagents are described herein. In other embodiments, a bis-acyliminepyridine compound is contacted with a monoamine in the presence of a metal salt. The bis-acyliminepyridine compound, the monoamine, and the metal salt may have structures as described herein. Additionally, the molar ratios of the reagents that may be utilized are described herein. The skilled artisan will recognize that embodiments relating to contacting an acyliminepyridine compound with an amine in the presence of a metal salt can be applied to the production of any hexadentate bimetallic complex as described herein.

In embodiments, a hexadentate bimetallic complex is produced by contacting an acyliminepyridine metal complex and a first amine to form a mixture, and recovering the hexadentate bimetallic complex from the mixture. In further embodiments the hexadentate bimetallic complex may be purified using methods known to those skilled in the art, such as recrystallization. In some embodiments, a mono-acyliminepyridine metal complex is contacted with a diamine. The mono-acyliminepyridine metal complex and diamine may have structures as described herein. Additionally, the molar ratios of the mono-acyliminepyridine metal complex to diamine that may be utilized are described herein. In other embodiments, a bis-acyliminepyridine metal complex is contacted with a monoamine. The bis-acyliminepyridine metal complex and monoamine may have structures as described herein. Additionally, the molar ratios of the bis-acyliminepyridine to monoamine that may be utilized are described herein. The skilled artisan will recognize that the embodiments relating to contacting an acyliminepyridine metal complex with an amine can be applied to the production of any hexadentate bimetallic complex embodiments as described herein.

In embodiments, a hexadentate bimetallic complex is produced by contacting an acyliminepyridine compound with a metal salt to form an acyliminepyridine metal complex in a mixture, followed by contacting an amine with the mixture. In a further embodiment, the hexadentate bimetallic complex is recovered from the mixture. In further embodiments, the hexadentate bimetallic complex may be purified using methods known to those skilled in the art, such as recrystallization. In some embodiments, a mono-acyliminepyridine compound is contacted with a metal salt to form a mixture comprising a mono-acyliminepyridine metal complex, and the mixture is contacted with a diamine. The mono-acyliminepyridine compound, mono-acyliminepyridine metal complex, and diamine may have structures as described herein. Additionally, the molar ratios of the reagents that may be utilized are described herein. In other embodiments, a bis-acyliminepyridine compound is contacted with a metal salt to form a mixture comprising a bis-acyliminepyridine metal complex, and the mixture is contacted with a monoamine. The bis-acyliminepyridine compound, bis-acyliminepyridine metal complex, and monoamine may have structures as described herein. Additionally, the molar ratios of the reagents that may be utilized are described herein. The skilled artisan will recognize that the embodiments relating to contacting an acyliminepyridine compound with a metal salt to form an acyliminepyridine metal complex in a mixture and then contacting an amine with the mixture can be applied to the production of any hexadentate bimetallic complex embodiments as described herein.

As described, a hexadentate bimetallic complex may be produced via various synthesis paths. Molar ratios of reagents employed in such synthesis paths may be dependent upon the particular paths selected. Embodiments relating the molar ratios of reagents within these hexadentate bimetallic production methods are described below.

In an embodiment, a hexadentate bimetallic complex is produced by contacting a mono-acyliminepyridine, a diamine, and a metal salt. The mono-acyliminepyridines, diamines, and metal salts are described herein. Additional details of this production method are described herein. In some embodiments, the molar ratio of mono-acyliminepyridine compound to diamine ranges from about 3:1 to about 1.8:1; alternatively, from about 2.5:1 to about 1.9:1; or alternatively, from about 2.1:1 to about 1.95:1. In other embodiments, the molar ratio of mono-acyliminepyridine compound to diamine is about 3:1; alternatively, about 2.5:1; alternatively, about 2.1:1; or alternatively, about 2:1. In some embodiments, the molar ratio of mono-acyliminepyridine compound to metal salt ranges from about 1:0.8 to about 1:1.2; alternatively, from about 1:1.09 to about 1:1.1. In other embodiments, the molar ratio of mono-acyliminepyridine compound to metal salt is about 1:0.8; alternatively, about 1:0.9; alternatively, about 1:1; alternatively, about 1:1.1; or alternatively, about 1:2. In some embodiments, the molar ratio of mono-acyliminepyridine compound to diamine to metal salt ranges from about 3:1:3 to about 1.75:1:1.75; alternatively, from about 2.5:1:2.5 to about 1.85:1:1.85; or alternatively, from about 2.25:1:2.25 to about 1.95:1:1.95. In other embodiments, the molar ratio of mono-acyliminepyridine compound to diamine to metal salt is about 2:1:2. In some embodiments, the mono-acyliminepyridine may be a mixture of mono-acyliminepyridines. In some embodiments, the diamine may be a mixture of diamines.

In an embodiment, a hexadentate bimetallic complex is produced by contacting a bis-acyliminepyridine compound, a monoamine, and a metal salt. The bis-acyliminepyridine compounds, monoamines, and metal salts are described herein. Additional details of this production method are described herein. In some embodiments, the molar ratio of bis-acyliminepyridine compound to monoamine ranges from about 1:3 to about 1:1.9; alternatively, from about 1:2.5 to about 1:1.95; or alternatively from about 1:2.25 to about 1:1.975. In other embodiments, the molar ratio of bis-acyliminepyridine compound to monoamine is about 1:3; alternatively, about 1:2.5; alternatively, about 1:2.25; or alternatively, about 1:2. In some embodiments, the molar ratio of bis-acyliminepyridine compound to metal salt ranges from about 1:2.2 to about 1:1.8; alternatively, from about 1:2.1 to about 1:1.9; or alternatively, from about 1:2.05 to about 1:1.95. In other embodiments, the molar ratio of bis-acyliminepyridine compound to metal salt is about 1:2.2; alternatively, about 1:2.1; alternatively, about 1:2.05; alternatively, about 1:2; alternatively, about 1:1.95; alternatively, about 1:1.9; or alternatively, about 1:1.8. In some embodiments, the molar ratio of bis-acyliminepyridine compound to monoamine to metal salt ranges from about 1:3:3 to about 1:1.75:1.75; alternatively, from about 1:2.5:2.5 to about 1:1.85:1.85; or alternatively, from about 1:2.25:2.25 to about 1:1.95:1.95. In other embodiments, the molar ratio of bis-acyliminepyridine compound to monoamine to metal salt is about 1:2.2. In some embodiments, the bis-acyliminepyridine may be a mixture of bis-acyliminepyridines. In some embodiments, the monoamine may be a mixture of monoamines.

In an embodiment, a hexadentate bimetallic complex is produced by contacting a mono-acyliminepyridine metal complex and a diamine. Mono-acyliminepyridine metal complexes and diamines are described herein. Additional details of this production method are described herein. The mono-acyliminepyridine metal complex may be produced by contacting a mono-acyliminepyridine compound and a metal salt at any ratio capable of producing the mono-acyliminepyridine metal complex. In some embodiments, the mono-acyliminepyridine metal complex is produced by contacting a mono-acyliminepyridine compound and a metal salt where the mono-acyliminepyridine compound to metal salt molar ratio may range from about 1:0.8 to about 1:1.2; or alternatively, the from about 1:1.09 to about 1:1.1. In other embodiments, the mono-acyliminepyridine compound to metal salt molar ratio is about 1:0.8; alternatively, about 1:0.9; alternatively, about 1:1; alternatively, about 1:1.1; or alternatively, about 1:2. In some embodiments, the molar ratio of mono-acyliminepyridine metal complex to diamine ranges from about 3:1 to about 1.8:1; alternatively, from about 2.5:1 to about 1.9:1; or alternatively, from about 2:1 to about 1.95:1. In other embodiments, the molar ratio of mono-acyliminepyridine metal complex to diamine is about 3:1; alternatively, about 2.5:1; alternatively, about 2.1:1; or alternatively, about 2:1. In some embodiments, the molar ratio of mono-acyliminepyridine compound to diamine to metal salt ranges from about 3:1:3 to about 1.75:1:1.75; alternatively, from about 2.5:1:2.5 to about 1.85:1:1.85; or alternatively, from about 2.25:1:2.25 to about 1.95:1:1.95. In other embodiments, the molar ratio of mono-acylpyridine to diamine to metal salt may be about 2:1:2. In some embodiments, the mono-acyliminepyridine compound may be a mixture of mono-acyliminepyridine compounds. In some embodiments, the mono-acyliminepyridine metal complex may be a mixture of mono-acylpyridine metal complexes. In some embodiments, the diamine may be a mixture of diamines.

In an embodiment, a hexadentate bimetallic complex is produced by contacting a bis-acyliminepyridine metal complex and a monoamine. The bis-acyliminepyridine metal complexes and monoamines are described herein. Additional details of this production method are described herein. The bis-acyliminepyridine metal complex may be produced by contacting a bis-acyliminepyridine compound and a metal salt at any ratio capable of producing the mono-acyliminepyridine metal complex. In some embodiments, the bis-acyliminepyridine metal complex is produced at a bis-acyliminepyridine compound to metal salt molar ratio ranging from about 1:2.2 to about 1:1.8; alternatively, from about 1:2.1 to about 1:1.9; or alternatively, from about 1:2.05 to about 1:1.95. In some embodiments, the bis-acyliminepyridine metal complex is produced at a bis-acyliminepyridine compound to metal salt molar ratio of about 1:2.2; alternatively, about 1:2.1; alternatively, about 1:2.05; alternatively, about 1:1.95; alternatively, about 1:1.9; or alternatively, about 1:1.8. In some embodiments, the hexadentate bimetallic complex is produced using a bis-acyliminepyridine metal complex to monoamine molar ratio ranging from about 1:3 to about 1:1.9; alternatively, from about 1:2.5 to about 1:1.95; or alternatively, from about 1:2.25 to about 1:1.975. In other embodiments, the hexadentate bimetallic complex is produced using a bis-acyliminepyridine metal complex to monoamine molar ratio of about 1:3; alternatively, about 1:2.5; alternatively, about 1:2.25; or alternatively, about 1:2. In some embodiments, the molar ratio of bis-acyliminepyridine compound to monoamine to metal salt ranges from about 1:3:3 to about 1:1.75:1.75; alternatively, from about 1:2.5:2.5 to about 1:1.85:1.85; or alternatively, from about 1:2.25:2.25 to about 1:1.95:1.95. In other embodiments, the molar ratio of bis-acyliminepyridine compound to monoamine to metal salt is about 1:2:2. In some embodiments, the bis-acyliminepyridine compound may be a mixture of bis-acyliminepyridine compounds. In some embodiments, the bis-acyliminepyridine metal complex may be a mixture of bis-acylpyridine metal complexes. In some embodiments, the monoamine may be a mixture of monoamines.

In an embodiment, a hexadentate bimetallic complex is produced by contacting a mono-acyliminepyridine compound with a metal salt to form a mixture comprising a mono-acyliminepyridine metal complex, then contacting a diamine with the mixture. The mono-acyliminepyridine compounds, diamines, and metal salts are described herein. Additional details of this production method are described herein.

In some embodiments, the molar ratio of mono-acyliminepyridine compound to metal salt ranges from about 1:0.8 to about 1:1.2; alternatively, from about 1:0.9 to about 1:1.1. In other embodiments, the molar ratio of mono-acyliminepyridine compound to metal salt is about 1:0.8; alternatively, about 1:0.9; alternatively, about 1:1; alternatively, about 1:1.1; or alternatively, about 1:1.2. In some embodiments, the molar ratio of mono-acyliminepyridine compound to diamine ranges from about 3:1 to about 1.8:1; alternatively, from about 2.5:1 to about 1.9:1; or alternatively, from about 2.1:1 to about 1.95:1. In other embodiments, the molar ratio of mono-acyliminepyridine compound to diamine is about 3:1; alternatively, about 2.5:1; alternatively, about 2.1:1; or alternatively, about 2:1. In some embodiments, the molar ratio of mono-acyliminepyridine compound to diamine to metal salt ranges from about 3:1:3 to about 1.75:1:1.75; alternatively, from about 2.5:1:2.5 to about 1.85:1:1.85; or alternatively, from about 2.25:1:2.25 to about 1.95:1:1.95. In other embodiments, the molar ratio of mono-acyliminepyridine compound to diamine to metal salt is about 2:1:2. In some embodiments, the mono-acyliminepyridine compound may be a mixture of mono-acyliminepyridine compounds. In some embodiments, the diamine may be a mixture of diamines.

In an embodiment, a hexadentate bimetallic complex is produced by contacting a bis-acyliminepyridine compound with a metal salt to form a mixture comprising a bis-acyliminepyridine metal complex, then contacting a monoamine with the mixture. The bis-acyliminepyridine compounds, monoamines, and metal salts are described herein. Additional details of this production method are described herein. In some embodiments, the molar ratio of bis-acyliminepyridine compound to metal salt ranges from about 1:2.2 to about 1:1.8; alternatively, from about 1:2.1 to about 1:1.9; or alternatively, from about 1:2.05 to about 1:1.95. In other embodiments, the molar ratio of bis-acyliminepyridine compound to metal salt is about 1:2.2; alternatively, about 1:2.1; alternatively, about 1:2.05; alternatively, about 1:1.95; alternatively, about 1:1.9; or alternatively, about 1:1.8. In some embodiments, the molar ratio of bis-acyliminepyridine compound to monoamine ranges from about 1:3 to about 1:1.9; alternatively, from about 1:2.5 to about 1:1.95; or alternatively from about 1:2.25 to about 1:1.975. In other embodiments, the molar ratio of bis-acyliminepyridine compound to monoamine is about 1:3; alternatively, about 1:2.5; alternatively, about 1:2.25; or alternatively, about 1:2. In some embodiments, the molar ratio of bis-acyliminepyridine compound to monoamine to metal salt ranges from about 1:3:3 to about 1:1.75:1.75; alternatively, from about 1:2.5:2.5 to about 1:1.85:1.85; or alternatively, from about 1:2.25:2.25 to about 1:1.95:1.95. In other embodiments, the molar ratio of bis-acyliminepyridine compound to monoamine to metal salt is about 1:2:2. In some embodiments, the bis-acyliminepyridine compound may be a mixture of bis-acyliminepyridine compounds. In some embodiments, the monoamine may be a mixture of monoamines.

The metal salt is typically the salt of a transition metal that produces a hexadentate bimetallic complex via a coordination reaction. In an embodiment, the metal salt is indicated by $M$-$X_n$ and $M'$-$X'_n$, wherein M and M' are metals and X and X' are anions. In some embodiments, M and M' may be metals selected from Group VB, VIB, VIII of the CAS version of the Periodic Table. In other embodiments, M and M' may be metals having a +3 oxidation state. In other embodiments, M and M' may be independently selected from the group consisting of cobalt, iron, nickel, chromium, vanadium, or mixtures thereof. In further embodiments, M and M' may be cobalt, iron, chromium, and vanadium, or mixtures thereof. In further embodiments, M and M' may be cobalt, iron, or mixtures thereof. In further embodiments, M and M' may be iron. In further embodiments, M and M' may be cobalt. In further embodiments, M and M' may be chromium. In further embodiments, M and M' may be nickel. In some embodiments, the anion is a halide or acetyl acetonate. In other embodiments, an anionic halide is fluoride, chloride, bromide, or iodide. In yet other embodiments, the anionic halide is chloride. In an embodiment, the metal salt is a cobalt salt. In an embodiment, the metal salt is an iron salt. In other embodiments the metal salt comprises iron. In yet other embodiments, the metal salt comprises cobalt. In some embodiments, the metal salt is cobalt(III) chloride, iron(III) chloride, or combinations thereof. In a non-limiting example, referring to structure 27, sites 70 and 80 are where the metal salt may coordinate to form the complex.

Each reaction in the production of a hexadentate complex may be carried out in a suitable solvent. Solvents suitable in the formation of hexadentate bimetallic complexes may include solvents typically employed by those skilled in the art. In some embodiments, the solvent may be alcohols, ethers, or mixtures thereof. In other embodiments, the solvent may be an alcohol. In other embodiments, the solvent may be an ether. In embodiments including alcohol, suitable alcohols may be n-butanol or ethanol. In embodiments including ether, a suitable ether may be tetrahydrofuran.

Various synthesis paths and sequences may be employed when producing the hexadentate bimetallic complexes from the amines, di-acylpyridines, and metal salts described herein. The following four synthesis paths (referred to as the first, second, third, and fourth synthesis methods) are non-limiting examples of methods for producing a hexadentate bimetallic complex as described herein.

In various embodiments, a first synthesis method for producing a hexadentate bimetallic complex comprises: (a) contacting a di-acylpyridine and a first amine to form a first mixture; (b) recovering an acyliminepyridine compound from the first mixture; (c) contacting the acyliminepyridine compound with a second amine and a metal salt to form a second mixture; and, (d) recovering the hexadentate bimetallic complex from the second mixture.

In some embodiments, the recovered acyliminepyridine compound may be purified using methods known to those skilled in the art, for example recrystallization. In some embodiments, the recovered hexadentate bimetallic complex may be purified using methods known to those skilled in the art, for example recrystallization. The first hexadentate bimetallic complex synthesis method may be practiced by recovering a mono-acyliminepyridine compound from the first mixture. Alternatively, the first hexadentate bimetallic complex synthesis method may be practiced by recovering a bis-acyliminepyridine compound from the first mixture.

In embodiments of the first hexadentate bimetallic complex synthesis wherein a mono-acyliminepyridine compound is recovered from the first mixture, the method for producing a hexadentate bimetallic complex comprises: (a) contacting a di-acylpyridine and a monoamine to form a first mixture; (b) recovering a mono-acyliminepyridine compound from the first mixture; (c) contacting the mono-acyliminepyridine compound with a diamine and a metal salt to form a second mixture; and, (d) recovering the hexadentate bimetallic complex from the second mixture. In some embodiments, the recovered mono-acyliminepyridine may be purified using methods known to those skilled in the art, for example recrystallization. In other embodiments, the recovered mono-acyliminepyridine may be used without further purification. In some embodiments, the recovered hexadentate bimetallic complex may be purified using methods known to those skilled in the art, for example recrystallization. In other embodiments, the recovered hexadentate bimetallic complex may be used without further purification.

The di-acylpyridine, monoamine, mono-acyliminepyridine, diamine, metal salt, and hexadentate bimetallic complex may have structures as described herein. The applicable di-acylpyridine to monoamine, mono-acyliminepyridine compound to diamine, mono-acyliminepyridine compound to metal salt, and mono-acyliminepyridine compound to diamine to metal salt molar ratios that may be used to form the first and second mixtures are described herein. The reaction conditions, for example temperature and time, utilized to form the mono-acyliminepyridine compound and the hexadentate bimetallic complex are described herein.

The first synthesis method may be applied to produce either specific hexadentate bimetallic complexes, or may be applied to produce a mixture of hexadentate bimetallic complexes by using mixtures of di-acyliminepyridines, monoamines, diamines, and metal salts.

The embodiments of the first hexadentate bimetallic complex synthesis method wherein a mono-acyliminepyridine compound is recovered from the first mixture may be applied to the synthesis of hexadentate bimetallic complexes as described herein using suitable di-acylpyridine(s), monoamine(s), diamine(s), and metal salt(s) within the synthesis method.

As a specific, non-limiting example of the first hexadentate bimetallic complex synthesis method wherein a mono-acyliminepyridine compound is recovered from the first mixture, the method for producing a hexadentate bimetallic complex comprises: (a) contacting a di-acylpyridine having structure 9 and a monoamine having structure 3 to form a first mixture; (b) recovering a mono-acyliminepyridine compound having structure 13 from the first mixture; (c) contacting the mono-acyliminepyridine compound with a diamine having structure 7 and a metal salt to form a second mixture; and (d) recovering the hexadentate bimetallic complex having structure 33 from the second mixture. In some embodiments, the recovered mono-acyliminepyridine compound having structure 13 may be purified using methods known to those skilled in the art, for example recrystallization. In other embodiments, the recovered mono-acyliminepyridine compound having structure 13 may be used without further purification. In some embodiments, the recovered hexadentate bimetallic complex having structure 33 may be purified using methods known to those skilled in the art, for example recrystallization. In other embodiments, the recovered hexadentate bimetallic complex having structure 33 may be used without further purification. In some embodiments, the metal salt may comprise iron, cobalt, or combinations thereof. In another embodiment, the metal salt comprises iron. In another embodiment, the metal salt comprises cobalt. Other applicable metal salts are described herein. Non-limiting examples of the molar ratios that may be used to form the first and second mixtures include a di-acylpyridine to monoamine molar ratio of about 1:1, a mono-acyliminepyridine compound to diamine molar ratio of about 2:1, a mono-acyliminepyridine compound to metal salt molar ratio of about 1:1, a mono-acyliminepyridine compound to diamine to metal salt molar ratio of about 2:1:2, either individually or in any combination thereof. Other applicable di-acylpyridine to monoamine, mono-acyliminepyridine compound to diamine, mono-acyliminepyridine compound to metal salt, and mono-acyliminepyridine compound to diamine to metal salt molar ratios that may be used to form the first and second mixtures are described herein.

In alternate embodiments of the first hexadentate bimetallic complex synthesis method wherein a bis-acyliminepyridine compound is recovered from the first mixture, the method for producing a hexadentate bimetallic complex comprises: (a) contacting a di-acylpyridine with a diamine to form a first mixture; (b) recovering a bis-acyliminepyridine compound from the first mixture; (c) contacting the bis-acyliminepyridine compound with a monoamine and a metal salt to form a second mixture; and, (d) recovering the hexadentate bimetallic complex. In some embodiments, the bis-acyliminepyridine compound may be purified using methods known to those skilled in the art, for example recrystallization. In other embodiments, the recovered bis-acyliminepyridine compound may be used without further purification. In some embodiments, the recovered hexadentate bimetallic complex may be purified using methods known to those skilled in the art, for example recrystallization. In other embodiments, the recovered hexadentate bimetallic complex may be used without further purification. The di-acylpyridine, diamine, bis-acyliminepyridine compound, monoamine, metal salt, and hexadentate bimetallic complex may have structures as described herein. The applicable di-acylpyridine to diamine, bis-acyliminepyridine compound to monoamine, bis-acyliminepyridine compound to metal salt, and bis-acyliminepyridine compound to monoamine to metal salt molar ratios that may be used to form the first and second mixtures are described herein. The reaction conditions, for example temperature and time, utilized to form the bis-acyliminepyridine compound and the hexadentate bimetallic complex are described herein. The alternate first synthesis method may be applied to produce either specific hexadentate bimetallic complexes or may be applied to the production of a mixture of hexadentate bimetallic complexes by using mixtures of di-acyliminepyridines, monoamines, diamines, and metal salts within the synthesis method.

The alternate embodiments of the first hexadentate bimetallic complex synthesis method wherein a bis-acyliminepyridine compound is recovered from the first mixture may be applied to the synthesis of hexadentate bimetallic complexes as described herein using the appropriate di-acylpyridine(s), monoamine(s), diamine(s), and metal salt(s) as described herein within the synthesis method. As a specific non-limiting example of the alternate first hexadentate bimetallic complex synthesis method wherein a bis-acyliminepyridine compound is recovered from the first mixture, the method for producing a hexadentate bimetallic complex comprises: (a) contacting a di-acylpyridine having structure 9 and a diamine having structure 7 to form a first mixture; (b) recovering a bis-acyliminepyridine compound having structure 17 from the first mixture; (c) contacting the bis-acyliminepyridine compound with a monoamine having structure 3 and a metal salt to form a second mixture; and, (d) recovering the hexadentate bimetallic complex having structure 33 from the second mixture. In some embodiments, the recovered bis-acyliminepyridine compound having structure 17 may be purified using methods known to those skilled in the art, for example recrystallization. In other embodiments, the recovered bis-acyliminepyridine compound having structure 17 may be used without further purification. In some embodiments, the recovered hexadentate bimetallic complex having structure 33 may be purified using methods known to those skilled in the art, for example recrystallization. In other embodiments, the recovered hexadentate bimetallic complex having structure 33 may be used without further purification. In some embodiments, the metal salt may comprise iron, cobalt, or combinations thereof. In another embodiment, the metal salt comprises iron. In another embodiment, the metal salt comprises cobalt. Other applicable metal salts are described herein. Non-limiting examples of the molar ratios that may be used to form the first and second mixtures include a di-acylpyridine to diamine molar ratio of about 2:1 (or alternatively, greater than about 2:1), a bis-acyliminepyridine compound to monoamine molar ratio of about 1:2, a bis-acyliminepyridine compound to metal salt molar ratio of about 1:2, a bis-acyliminepyridine compound to monoamine to metal salt molar ratio of about 1:2:2, either individually or in any combination thereof. Other applicable di-acylpyridine to diamine, bis-acyliminepyridine compound to monoamine, bis-acyliminepyridine compound to metal salt, and bis-acyliminepyridine to monoamine to metal salt molar ratios that may be used to form the first and second mixtures are described herein.

In general, the second synthesis method for producing a hexadentate bimetallic complex comprises: (a) contacting a di-acylpyridine and a first amine to form a first mixture; (b) recovering an acyliminepyridine compound from the first mixture; (c) contacting the acyliminepyridine compound with a metal salt to form a second mixture; (d) recovering a acyliminepyridine metal complex from the second mixture; (e) contacting the acyliminepyridine metal complex with a second amine to form a third mixture; and, (f) recovering the hexadentate bimetallic complex from the third mixture.

In some embodiments, the recovered acyliminepyridine compound may be purified using methods known to those skilled in the art, for example recrystallization. In other embodiments, the recovered acyliminepyridine metal complex may be purified using methods known to those skilled in the art, for example recrystallization. In yet other embodiments, the recovered hexadentate bimetallic complex may be purified using methods known to those skilled in the art, for example recrystallization.

The second hexadentate bimetallic complex synthesis method may be practiced by recovering a mono-acyliminepyridine compound from the first mixture and a mono-acyliminepyridine metal complex from the second mixture. Alternatively, the second hexadentate bimetallic complex synthesis method may be practiced by recovering a bis-acyliminepyridine compound from the first mixture and a bis-acyliminepyridine metal complex from the second mixture.

In embodiments of the second hexadentate bimetallic complex synthesis method wherein a mono-acyliminepyridine compound is recovered from the first mixture and a mono-acyliminepyridine metal complex is recovered from the second mixture, the method for producing a hexadentate bimetallic complex comprises: (a) contacting a di-acylpyridine and a monoamine to form a first mixture; (b) recovering a mono-acyliminepyridine compound from the first mixture; (c) contacting the mono-acyliminepyridine compound with a metal salt to form a second mixture; (d) recovering a mono-acyliminepyridine metal complex from the second mixture; (e) contacting the mono-acyliminepyridine metal complex with a diamine to form a third mixture; and (f) recovering a hexadentate bimetallic complex from the third mixture. In some embodiments, the recovered mono-acyliminepyridine compound may be purified using methods known to those skilled in the art, for example recrystallization. In other embodiments, the recovered mono-acyliminepyridine compound may be used without further purification. In some embodiments, the recovered mono-acyliminepyridine metal complex may be purified using methods known to those skilled in the art, for example recrystallization. In other embodiments, the recovered mono-acyliminepyridine metal complex may be used without further purification. In some embodiments, the recovered hexadentate bimetallic complex may be purified using methods known to those skilled in the art, for example recrystallization. In other embodiments, the recovered hexadentate bimetallic complex may be used without further purification. The di-acylpyridine, monoamine, mono-acyliminepyridine compound, metal salt, mono-acyliminepyridine metal complex, diamine, and hexadentate bimetallic complex may have structures as described herein.

The applicable di-acylpyridine to monoamine, mono-acyliminepyridine compound to metal salt, mono-acyliminepyridine metal complex to diamine, and mono-acyliminepyridine to diamine to metal salt molar ratios that may be used to form the first, second, and third mixtures are described herein. The reaction conditions, for example temperature and time, utilized to form the mono-acyliminepyridine compound, the mono-acyliminepyridine metal complex, and/or the hexadentate bimetallic complex are described herein. The second hexadentate bimetallic synthesis method may be applied to produce either specific hexadentate bimetallic complexes or may be applied to produce a mixture of hexadentate bimetallic complexes by using mixtures of di-acylpyridines, monoamines, diamines, or metal salts within the synthesis method.

The embodiments of the second hexadentate bimetallic complex synthesis method wherein a mono-acyliminepyridine compound is recovered from the first mixture and a mono-acyliminepyridine metal complex is recovered from the second mixture may be applied to the synthesis of hexadentate bimetallic complexes having structures as described herein using the appropriate di-acylpyridine(s), monoamine(s), diamine(s), and metal salt(s) as described herein within the synthesis method.

As a specific, non-limiting example of the second hexadentate bimetallic complex synthesis method wherein a mono-acyliminepyridine compound is recovered from the first mixture and a mono-acyliminepyridine metal complex is recovered from the second mixture, the method for producing a hexadentate bimetallic complex comprises: (a) contacting a di-acylpyridine having structure 9 and a monoamine having structure 3 to form a first mixture; (b) recovering a mono-acyliminepyridine compound having structure 13 from the first mixture; (c) contacting the mono-acyliminepyridine compound with a metal salt to form a second mixture; (d) recovering a mono-acyliminepyridine metal complex having structure 21 from the second mixture; (e) contacting the mono-acyliminepyridine metal complex with a diamine having structure 7 to form a third mixture; and, (f) recovering the hexadentate bimetallic complex of structure 33 from the third mixture. In some embodiments, the recovered mono-acyliminepyridine compound having structure 13 may be purified using methods known to those skilled in the art, for example recrystallization. In other embodiments, the recovered mono-acyliminepyridine compound having structure 13 may be used without further purification. In some embodiments, the recovered mono-acyliminepyridine metal complex having structure 21 may be purified using methods known to those skilled in the art, for example recrystallization. In other embodiments, the recovered mono-acyliminepyridine metal complex having structure 21 may be used without further purification. In some embodiments, the recovered hexadentate bimetallic complex having structure 33 may be purified using methods known to those skilled in the art, for example recrystallization. In other embodiments, the recovered hexadentate bimetallic complex having structure 33 may be used without further purification. In some embodiments, the metal salt may comprise iron, cobalt, or combinations thereof. In another embodiment, the metal salt comprises iron. In another embodiment, the metal salt comprises cobalt. Other applicable metal salts are described herein. Non-limiting examples of the molar ratios that may be used to form the first, second, and third mixtures include a di-acylpyridine to monoamine molar ratio of about 1:1 (alternatively, greater than about 1:1), a mono-acyliminepyridine compound to metal salt molar ratio of about 1:1, a mono-acyliminepyridine metal complex to diamine molar ratio of about 2:1, and a mono-acyliminepyridine to diamine to metal salt molar ratio about 2:1:2, either individually or in any combination thereof. Other applicable di-acylpyridine to monoamine, mono-acyliminepyridine compound to metal salt, mono-acyliminepyridine metal complex to diamine, mono-acyliminepyridine to diamine to metal salt molar ratios that may be used to form the first, second, and third mixtures are described herein.

In alternate embodiments of the second hexadentate bimetallic complex synthesis method wherein a bis-acyliminepyridine compound is recovered from the first mixture and a bis-acyliminepyridine metal complex is recovered from the second mixture, the method comprises: (a) contacting a di-acylpyridine and a diamine to form a first mixture; (b) recovering a bis-acyliminepyridine compound from the first mixture; (c) contacting the bis-acyliminepyridine compound with a metal salt to form a second mixture; (d) recovering a bis-acyliminepyridine metal complex from the second mixture; (e) contacting the bis-acyliminepyridine complex with a monoamine to form a third mixture; and (f) recovering the hexadentate bimetallic complex from the third mixture. In some embodiments, the recovered bis-acyliminepyridine compound may be purified using methods known to those skilled in the art, for example recrystallization. In other embodiments, the recovered bis-acyliminepyridine compound may be used without further purification. In some embodiments, the recovered bis-acyliminepyridine metal complex may be purified using methods known to those skilled in the art, for example recrystallization. In other embodiments, the recovered bis-acyliminepyridine metal complex may be used without further purification. In some embodiments, the recovered hexadentate bimetallic complex may be purified using methods known to those skilled in the art, for example recrystallization. In other embodiments, the recovered hexadentate bimetallic complex is used without further purification.

The di-acylpyridine, diamine, bis-acyliminepyridine compound, metal salt, bis-acyliminepyridine metal complex, monoamine, and hexadentate bimetallic complex may have the structures described herein. The applicable di-acylpyridine to diamine, bis-acyliminepyridine compound to metal salt, bis-acyliminepyridine metal complex to monoamine, and/or bis-acyliminepyridine compound to monoamine to metal salt molar ratios that may be used to form the first, second, and third mixtures are described herein. The reaction conditions, for example temperature and time, utilized to form the bis-acyliminepyridine compound, bis-acyliminepyridine metal complex, and hexadentate bimetallic complex are described herein. The alternate second synthesis method may be applied to produce either specific hexadentate bimetallic complexes or a mixture of hexadentate bimetallic complexes by using mixtures of differing di-acylpyridines, monoamines, diamines, or metal salts within the synthesis method.

The alternate embodiments of the second hexadentate bimetallic complex synthesis method wherein a bis-acyliminepyridine compound is recovered from the first mixture and a bis-acyliminepyridine metal complex is recovered from the second mixture may be applied to the synthesis of hexadentate bimetallic complexes as described herein using the appropriate di-acylpyridine(s), monoamine(s), diamine(s), and metal salt(s) as described herein within the synthesis method. As a specific, non-limiting example of the alternate second hexadentate bimetallic complex synthesis method wherein a bis-acyliminepyridine compound is recovered from the first mixture and a bis-acyliminepyridine metal complex is recovered from the second mixture, the method for producing a hexadentate bimetallic complex comprises: (a) contacting a di-acylpyridine having structure 9 and a diamine having structure 7 to form a first mixture; (b) recovering a bis-acyliminepyridine compound having structure 17 from the first mixture; (c) contacting the bis-acyliminepyridine compound with a metal salt to form a second mixture; (d) recovering a bis-acyliminepyridine metal complex having structure 25 from the second mixture; (e) contacting the bis-acyliminepyridine metal complex with a monoamine having structure 3 to form a third mixture; and, (f) recovering the hexadentate bimetallic complex having structure 33 from the third mixture.

In some embodiments, the recovered bis-acyliminepyridine compound having structure 17 may be purified using methods known to those skilled in the art, for example recrystallization. In other embodiments, the recovered bis-acyliminepyridine compound having structure 17 may be used without further purification. In some embodiments, the recovered bis-acyliminepyridine metal complex having structure 25 may be purified using methods known to those skilled in the art, for example recrystallization. In other embodiments, the recovered bis-acyliminepyridine metal complex having structure 25 may be used without further purification. In some embodiments, the recovered hexadentate bimetallic complex having structure 33 may be purified using methods known to those skilled in the art, for example recrystallization. In other embodiments, the recovered hexadentate bimetallic complex having structure 33 may be used without further purification. In an embodiment, the metal salt may comprise iron, cobalt, or combinations thereof. In another embodiment, the metal salt comprises iron. In an embodiment, the metal salt comprises cobalt.

Non-limiting examples of the molar ratios that may be used to form the first, second, a n d third mixtures include a di-acylpyridine to diamine molar ratio of about 2:1 (or, alternatively, greater than about 2:1), a bis-acyliminepyridine compound to metal salt molar ratio of about 1:2, a bis-acyliminepyridine compound to monoamine molar ratio of about 1:2, a bis-acyliminepyridine metal complex to monoamine molar ratio of about 1:2, a bis-acyliminepyridine to monoamine to metal salt molar ratio of about 1:2:2, either individually or in any combination thereof. Other applicable molar ratios of di-acylpyridine to diamine, bis-acyliminepyridine compound to metal salt, bis-acyliminepyridine compound to monoamine, bis-acyliminepyridine metal complex to monoamine, and bis-acyliminepyridine compound to monoamine to metal salt that may be used to from the first, second, and third mixtures are described herein.

In general, the third synthesis method for producing a hexadentate bimetallic complex comprises: (a) contacting a di-acylpyridine and a first amine to form a first mixture; (b) recovering an acyliminepyridine compound from the first mixture; (c) contacting the acyliminepyridine compound with a metal salt to form an acyliminepyridine metal complex in a second mixture; (d) contacting a second amine with the second mixture to form a third mixture; and, (e) recovering the hexadentate bimetallic complex from the third mixture.

In some embodiments, the recovered acyliminepyridine compound may be purified using methods known to those skilled in the art, for example recrystallization. In some embodiments, the recovered hexadentate bimetallic complex may be purified using methods known to those skilled in the art, for example recrystallization. The third hexadentate bimetallic complex synthesis method may be practiced by recovering a mono-acyliminepyridine compound from the first mixture. Alternatively, the third hexadentate bimetallic complex synthesis method may be practiced by recovering a bis-acyliminepyridine compound from the first mixture.

In embodiments of the third hexadentate bimetallic complex synthesis method wherein a mono-acyliminepyridine compound is recovered from the first mixture, the method for producing a hexadentate bimetallic complex comprises: (a) contacting a di-acylpyridine and a monoamine to form a first mixture; (b) recovering a mono-acyliminepyridine compound from the first mixture; (c) contacting the mono-acyliminepyridine compound with a metal salt to form a mono-acyliminepyridine metal complex in a second mixture; (d) contacting a diamine with the second mixture to form a third mixture; and, (e) recovering the hexadentate bimetallic complex from the third mixture. In some embodiments, the recovered mono-acyliminepyridine compound may be purified using methods known to those skilled in the art, for example recrystallization. In other embodiments, the recovered mono-acyliminepyridine compound may be used without further purification. In some embodiments, the recovered hexadentate bimetallic complex may be purified using methods known to those skilled in the art, for example recrystallization. In other embodiments, the recovered hexadentate bimetallic complex may be used without further purification. The di-acylpyridine, monoamine, mono-acyliminepyridine compound, metal salt, mono-acyliminepyridine metal complex, diamine, and hexadentate bimetallic complex may have the structures as described herein.

The applicable molar ratios of di-acylpyridine to monoamine, mono-acyliminepyridine compound to metal salt, mono-acyliminepyridine compound to diamine, and mono-acyliminepyridine compound to diamine to metal salt that may be used to form the first, second, and third mixtures are described herein. The reaction conditions, for example temperature and time, utilized to form the mono-acyliminepyridine compound, the mono-acyliminepyridine metal complex, and the hexadentate bimetallic complex are described herein. The third synthesis method may be applied to produce either specific hexadentate bimetallic complexes or a mixture of hexadentate bimetallic complexes by using mixtures of di-acylpyridines, monoamines, diamines, or metal salts within the synthesis method.

Embodiments of the third hexadentate bimetallic complex synthesis method wherein a mono-acyliminepyridine compound is recovered from the first mixture may be applied to the synthesis of hexadentate bimetallic complexes as described herein using suitable di-acylpyridine(s), monoamine(s), diamine(s), and metal salt(s) as described herein within the synthesis method. As a specific, non-limiting example of the third synthesis method wherein a mono-acyliminepyridine compound is recovered from the first mixture, the method comprises: (a) contacting a di-acylpyridine having structure 9 and a monoamine having structure 3 to form a first mixture; (b) recovering a mono-acyliminepyridine compound having structure 13 from the first mixture; (c) contacting the mono-acyliminepyridine compound with a metal salt to form a mono-acyliminepyridine metal complex having structure 21 in a second mixture; (d) contacting a diamine having structure 7 with the second mixture to form a third mixture; and recovering the hexadentate bimetallic complex having structure 33 from the third mixture. In some embodiments, the recovered mono-acyliminepyridine compound having structure 13 may be purified using methods known to those skilled in the art, for example recrystallization. In other embodiments, the recovered mono-acyliminepyridine compound having structure 13 may be used without further purification. In some embodiments, the recovered hexadentate bimetallic complex having structure 33 may be purified using methods known to those skilled in the art, for example recrystallization. In other embodiments, the recovered hexadentate bimetallic complex having structure 33 may be used without further purification. In some embodiments, the metal salt may comprise iron, cobalt, or combinations thereof. In another embodiment, the metal salt comprises iron. In another embodiment, the metal salt comprises cobalt. Other applicable metal salts are described herein.

Non-limiting examples of the molar ratios that may be used to form the first, second, and third mixtures include a di-acylpyridine to monoamine molar ratio of about 1:1 (or alternatively, greater than about 1:1), a mono-acyliminepyridine compound to metal salt molar ratio of about 1:1, a mono-acyliminepyridine compound to diamine molar ratio of about 2:1, a mono-acyliminepyridine compound to diamine to metal salt molar ratio of about 2:1:2, either individually or in any combination thereof. Other applicable di-acylpyridine to monoamine, mono-acyliminepyridine compound to metal salt, mono-acyliminepyridine compound to diamine, and mono-acyliminepyridine compound to diamine to metal salt molar ratios that may be used to form the first, second, and third mixtures are described herein.

In alternate embodiments of the third hexadentate bimetallic complex synthesis method wherein a bis-acyliminepyridine compound is recovered from the first mixture, the method for producing a hexadentate bimetallic complex comprises: (a) contacting a di-acylpyridine and a diamine to form a first mixture; (b) recovering a bis-acyliminepyridine compound from the first mixture; (c) contacting the bis-acyliminepyridine compound with a metal salt to form a bis-acyliminepyridine metal complex in a second mixture; (d) contacting a monoamine with the second mixture to form a third mixture; and, (e) recovering the hexadentate bimetallic complex from the third mixture. In some embodiments, the recovered bis-acyliminepyridine compound may be purified using methods known to those skilled in the art, for example recrystallization. In other embodiments, the recovered bis-acyliminepyridine compound may be used without further purification. In some embodiments, the recovered hexadentate bimetallic complex may be purified using methods known to those skilled in the art, for example recrystallization. In other embodiments, the recovered hexadentate bimetallic complex may be used without further purification. The di-acylpyridine, monoamine, bis-acyliminepyridine compound, metal salt, bis-acyliminepyridine metal complex, diamine, and hexadentate bimetallic complex may have structures as described herein.

Suitable molar ratios of di-acylpyridine to diamine, bis-acyliminepyridine compound to metal salt, bis-acyliminepyridine compound to monoamine, and bis-acyliminepyridine compound to monoamine to metal salt that may be used to form the first, second, and third mixtures are described herein. Reaction conditions, for example temperature and time, utilized to form the bis-acyliminepyridine compound, the bis-acyliminepyridine metal complex and the hexadentate bimetallic complex are described herein. The alternate third synthesis method may be applied to produce either specific hexadentate bimetallic complexes or a mixture of hexadentate bimetallic complexes by using mixtures of di-acylpyridines, monoamines, diamines, or metal salts within the synthesis method.

The alternate embodiments of the third hexadentate bimetallic complex synthesis method wherein a bis-acyliminepyridine compound is recovered from the first mixture may be applied to the synthesis of hexadentate bimetallic compounds having structures as described herein using appropriate di-acylpyridine(s), monoamine(s), diamine(s), and metal salt(s) as described herein within the synthesis method. As a specific, non-limiting example of the alternate third hexadentate bimetallic complex synthesis method wherein a bis-acyliminepyridine compound is recovered from the first mixture, the method for producing a hexadentate bimetallic complex comprises: (a) contacting a di-acylpyridine having structure 9 and a diamine having structure 7 to form a first mixture; (b) recovering a bis-acyliminepyridine compound having structure 17 from the first mixture; (c) contacting the bis-acyliminepyridine compound with a metal salt to form a bis-acyliminepyridine metal complex having structure 25 in a second mixture; (d) contacting a monoamine having structure 3 with the second mixture to form a third mixture; and, (e) recovering the hexadentate bimetallic complex having structure 33 from the third mixture. In some embodiments, the recovered bis-acyliminepyridine compound having structure 17 may be purified using methods known to those skilled in the art, for example recrystallization. In other embodiments, the recovered bis-acyliminepyridine compound having structure 17 may be used without further purification. In some embodiments, the recovered hexadentate bimetallic complex having structure 33 may be purified using methods known to those skilled in the art, for example recrystallization. In other embodiments, the recovered hexadentate bimetallic complex having structure 33 may be used without further purification. In an embodiment, the metal salt may comprise iron, cobalt, or combinations thereof. In another embodiment, the metal salt comprises iron. In another embodiment, the metal salt comprises cobalt. Other applicable metal salts are described herein.

Non-limiting examples of the molar ratios that may be used to form the first, second, and third mixtures include a di-acylpyridine to diamine molar ratio of about 2:1 (or alternatively, greater than about 2:1), a bis-acyliminepyridine compound to metal salt molar ratio of about 1:2, a bis-acyliminepyridine compound to monoamine molar ratio of about 1:2, and a bis-acyliminepyridine compound to monoamine to metal salt molar ratio of about 1:2:2, either individually or in any combination thereof. Other applicable di-acylpyridine to diamine, bis-acyliminepyridine compound to metal salt, bis-acyliminepyridine compound to monoamine, and bis-acyliminepyridine compound to monoamine to metal salt molar ratios are described herein.

In general, the fourth synthesis method for producing a hexadentate bimetallic complex comprises: (a) contacting a di-acylpyridine and a first amine to form an acyliminepyridine compound in a first mixture; (b) contacting a metal salt with the first mixture to form a second mixture; (c) recovering an acyliminepyridine metal complex from the second mixture; (d) contacting the acyliminepyridine metal complex with a second amine to form a third mixture; and (e) recovering the hexadentate bimetallic complex from the third mixture. In some embodiments, the recovered acyliminepyridine metal complex may be purified using methods known to those skilled in the art, for example recrystallization. In some embodiments, the recovered hexadentate bimetallic complex may be purified using methods known to those skilled in the art, for example recrystallization. The fourth hexadentate bimetallic complex synthesis method may be practiced by recovering a mono-acyliminepyridine metal complex from the second mixture. Alternatively, the fourth synthesis hexadentate bimetallic complex synthesis method may be practiced by recovering a bis-acyliminepyridine metal complex from the second mixture.

In embodiments of the fourth hexadentate bimetallic complex synthesis method wherein a mono-acyliminepyridine metal complex is recovered from the second mixture, the method for producing a hexadentate bimetallic complex comprises: (a) contacting a di-acylpyridine and a monoamine to form a mono-acyliminepyridine compound in a first mixture; (b) contacting a metal salt with the first mixture to form a second mixture; (c) recovering a mono-acyliminepyridine metal complex from the second mixture; (d) contacting the mono-acyliminepyridine complex with a diamine to form a third mixture; and (e) recovering the hexadentate bimetallic complex from the second mixture. In some embodiments, the recovered mono-acyliminepyridine metal complex may be purified using methods known to those skilled in the art, for example recrystallization. In other embodiments, the recovered mono-acyliminepyridine metal complex may be used without further purification. In some embodiments, the recovered hexadentate bimetallic complex may be purified using methods known to those skilled in the art, for example recrystallization. In other embodiments, the recovered hexadentate bimetallic complex may be used without further purification. The di-acylpyridine, monoamine, mono-acyliminepyridine compound, metal salt, mono-acyliminepyridine metal complex, diamine, and hexadentate bimetallic complex may have structures as described herein.

The applicable molar ratios of di-acylpyridine to monoamine, monoamine to metal salt, mono-acyliminepyridine metal complex to diamine, and mono-amine to diamine to metal salt that may be used to form the first, second, and third mixtures are described herein. The reaction conditions, for example temperature and time, utilized to form the mono-acyliminepyridine compound, mono-acyliminepyridine metal complex, and hexadentate bimetallic complex are described herein. The fourth synthesis method may be applied to produce either specific hexadentate bimetallic complexes or a mixture of hexadentate bimetallic complexes by using mixtures of di-acylpyridines, monoamines, diamines, or metal salts.

The embodiments of the fourth hexadentate bimetallic complex synthesis method wherein a mono-acyliminepyridine metal complex is recovered from the second mixture may be applied to the synthesis of hexadentate bimetallic compounds having structures as described herein using appropriate di-acylpyridine(s), monoamine(s), diamine(s), and metal salt(s) as described herein within the synthesis method. As a specific, non-limiting example of the fourth hexadentate bimetallic complex synthesis method wherein a mono-acyliminepyridine metal complex is recovered from the second mixture, the method comprises: (a) contacting a di-acylpyridine having structure 9 and a monoamine having structure 3 to form a mono-acyliminepyridine compound having structure 13 in a first mixture; (b) contacting a metal salt with the first mixture to form a second mixture; (c) recovering the mono-acyliminepyridine metal complex having structure 21; (d) contacting the acyliminepyridine metal complex with a diamine having structure 7 to form a third mixture; and, (e) recovering the hexadentate bimetallic complex having structure 33 from the second mixture. In some embodiments, the recovered mono-acyliminepyridine metal complex having structure 21 may be purified using methods known to those skilled in the art, for example recrystallization. In other embodiments, the recovered mono-acyliminepyridine metal complex having structure 21 may be used without further purification. In some embodiments, the recovered hexadentate bimetallic complex having structure 33 may be purified using methods known to those skilled in the art, for example recrystallization. In other embodiments, the recovered hexadentate bimetallic complex having structure 33 may be used without further purification. In some embodiments, the metal salt may comprise iron, cobalt, or combinations thereof. In another embodiment, the metal salt comprises iron. Other applicable metal salts are described herein.

Non-limiting examples of the molar ratios that may be used to form the first, second, and third mixtures include a di-acylpyridine to monoamine molar ratio of about 1:1 (or alternatively, greater than, a mono-amine to metal salt molar ratio of about 1:1, a mono-acyliminepyridine metal complex to diamine molar ratio of about 2:1, and a mono-amine to diamine to metal salt may molar ratio of about 2:1:2, either individually or in any combination thereof. Other applicable di-acylpyridine to monoamine, mono-amine to metal salt, mono-acyliminepyridine metal complex to diamine, and mono-amine to diamine to metal salt molar ratios that may be used to form the first, second, and third mixtures are described herein.

In alternate embodiments of the fourth hexadentate bimetallic complex synthesis method wherein a bis-acyliminepyridine metal complex is recovered from the second mixture, the method for producing a hexadentate bimetallic complex comprises: (a) contacting a di-acylpyridine and a diamine to form a bis-acyliminepyridine compound in a first mixture; (b) contacting a metal salt with the first mixture to form a second mixture; (c) recovering the bis-acyliminepyridine metal complex; (d) contacting the bis-acyliminepyridine metal complex with a monoamine to form a third mixture; and, (e) recovering the hexadentate bimetallic complex from the third mixture. In some embodiments, the recovered bis-acyliminepyridine metal complex may be purified using methods known to those skilled in the art, for example recrystallization. In other embodiments, the recovered bis-acyliminepyridine metal complex may be used without further purification. In some embodiments, the recovered hexadentate bimetallic complex may be purified using methods known to those skilled in the art, for example recrystallization. In other embodiments, the recovered hexadentate bimetallic complex may be used without further purification. The di-acylpyridine, diamine, bis-acyliminepyridine compound, metal salt, mono-acyliminepyridine metal complex, monoamine, and hexadentate bimetallic complex may have structures as described herein.

The applicable molar ratios of di-acylpyridine to diamine, diamine to metal salt, bis-acyliminepyridine metal complex to monoamine, diamine to monoamine to metal salt that may be used to form the first, second, and third mixtures are described herein. The reaction conditions, for example temperature and time, utilized to form the mono-acyliminepyridine compound, mono-acyliminepyridine metal complex, and hexadentate bimetallic complex are described herein. The alternate fourth synthesis method may be applied to produce either specific hexadentate bimetallic complexes or a mixture of hexadentate bimetallic complexes by using mixtures of di-acylpyridines, monoamines, diamines, or metal salts within the synthesis method.

The alternate embodiments of the fourth hexadentate bimetallic complex synthesis method wherein a bis-acyliminepyridine metal complex is recovered from the second mixture may be applied to the synthesis of hexadentate bimetallic compounds as described herein using appropriate di-acylpyridine(s), monoamine(s), diamine(s), and metal salt(s) as described herein within the synthesis method. As a specific, non-limiting example of the alternate fourth hexadentate bimetallic complex synthesis method wherein a bis-acyliminepyridine metal complex is recovered from the second mixture, the method for producing a hexadentate bimetallic complex comprises: (a) contacting a di-acylpyridine having structure 9 and a diamine having structure 7 to form a bis-acyliminepyridine compound having structure 17 in a first mixture; (b) contacting a metal salt with the first mixture to form a second mixture; (c) recovering a bis-acyliminepyridine metal complex having structure 25 from the second mixture; (d) contacting the bis-acyliminepyridine metal complex with a monoamine having structure 3 to form a third mixture; and, (e) recovering the hexadentate bimetallic complex having structure 33 from the second mixture. In some embodiments, the recovered bis-acyliminepyridine metal complex having structure 25 may be purified using methods known to those skilled in the art, for example recrystallization. In other embodiments, the recovered bis-acyliminepyridine metal complex having structure 25 may be used without further purification. In some embodiments, the recovered hexadentate bimetallic complex having structure 33 may be purified using methods known to those skilled in the art, for example recrystallization. In other embodiments, the recovered hexadentate bimetallic complex having structure 33 may be used without further purification. In an embodiment, the metal salt may comprise iron, cobalt, or combinations thereof. In another embodiment, the metal salt comprises iron. In an embodiment, the metal salt comprises cobalt.

Non-limiting examples of the molar ratios that may be used to form the first, second, and third mixtures include a di-acylpyridine to diamine molar ratio of about 2:1 (or alternatively, greater than about 2:1), a diamine to metal salt molar ratio of about 1:2, a bis-acyliminepyridine metal complex to monoamine molar ratio of about 1:2, and a diamine to monoamine to metal salt molar ratio of about 1:2:2, either individually or in any combination thereof. Other applicable di-acylpyridine to diamine, diamine to metal salt, bis-acyliminepyridine metal complex to monoamine, and diamine to monoamine to metal salt molar ratios that may be used to form the first, second, and third mixtures are described herein.

Unless specified otherwise, the terms contacted, combined, and 'in the presence of' refer to any addition sequence, order, or concentration for contacting or combining two or more components or reactants. Combining or contacting of components, e.g., the various compounds having structures set forth in Tables 1 through 5, according to the various methods described herein may occur in one or more contact zones under suitable reaction conditions such as temperature, pressure, contact time, flow rates, etc. to produce the desired compound. The contact zone may be disposed in a vessel, e.g. a storage tank, tote, container, mixing vessel, reactor, etc.; a length of pipe, e.g. a tee, inlet, injection port, or header for combining component feed lines into a common line; or any other suitable apparatus for bringing the components into contact. The methods may be carried out in a batch or continuous process as is suitable for a given embodiment, with physical parameters of the contact zone being specified accordingly. The reaction for forming at least one imine bond of the hexadentate bimetallic complex in the presence of a metal salt or metal complex may be carried out over a wide range of temperatures, from about −20° C. to 200° C.; alternatively, from about 25° C. to 125° C.; or alternatively, from about 40° C. to 100° C. The time needed to form at least one imine bond of the hexadentate bimetallic complex in the presence of a metal salt or metal complex, at the temperature described herein, may be from 30 minutes to 48 hours; alternatively from 1 hour to 36 hours; alternatively from 2 hours to 24 hours. The temperatures and times described herein are generally applicable to all methods of forming at least one imine bond of the hexadentate bimetallic complex in the presence of a metal salt or metal complex described herein.

In embodiments utilizing a vessel for contacting the components, the components may be optionally mixed by a mixer disposed in the vessel and the formed mixture may then be removed for subsequent processing. In embodiments utilizing a tee or other means for combining lines such as a header, an optional in-line mixer may be placed in the commingled line to ensure that adequate contacting of the combined components takes place, and the mixture is thus formed as it passes through the commingled feed line.

Where a method recites contact or combination of components, such may be carried out by contacting or combining all or a portion of such components in various embodiments. None, some, or all of the contacting steps may be carried out in the presence of a solvent, which may be introduced to a contact zone via inclusion with one or more components or may be introduced separately to a contact zone, for example in a solvent line or as an initial charge to a contact zone.

In various embodiments of the methods described herein, a hexadentate bimetallic complex, for example the hexadentate bimetallic complex having structure 27, 28, 29, 30, 31, 33, 34, or mixtures thereof, is produced at an overall yield of about equal to or greater than 55 weight percent based on the weight of the limiting reagent; alternatively, the yield is about equal to or greater than about 60 weight percent; alternatively, 65 weight percent; alternatively, 70 weight percent; alternatively, 75 weight percent; or alternatively, 80 weight percent. In some embodiments, the limiting reagent for determination of the overall yield is the di-acylpyridine compound. In other embodiments, the limiting agent for determination of the overall yield is the amine (monoamine or diamine). In other embodiments, the limiting agent for determination of the overall yield is the metal salt.

In other embodiments, the step wherein the imine bond of the hexadentate bimetallic complex is formed in the presence of a metal salt or metal complex proceeds at a yield of about equal to or greater than 60 weight percent based on the weight of the limiting reagent; alternatively, the yield is about equal to or greater than about 70 weight percent; alternatively, 80 weight percent; alternatively, 90 weight percent; or alternatively, 95 weight percent. The determination of the yield of the step wherein in the imine bond of the hexadentate bimetallic complex is formed in the presence of a metal salt or metal complex may be based upon the limiting reagent of the specific method utilized. In embodiments, the limiting agent for determination of the yield of the step wherein the imine bond of the hexadentate bimetallic complex is formed in the presence of a metal salt or metal complex is the acyliminepyridine metal complex (mono-acyliminepyridine metal complex or bis-acyliminepyridine metal complex); alternatively, the acyliminepyridine compound (mono-acyliminepyridine compound or bis-acyliminepyridine compound); alternatively, the amine (monoamine or diamine); or alternatively, the metal salt.

Hexadentate bimetallic complexes may be employed to polymerize or oligomerize olefins. The polymerization or oligomerization may be carried out by contacting the hexadentate bimetallic complex with one or more monomers. In other embodiments, the polymerization or oligomerization may be carried out by activating the hexadentate bimetallic complex in the presence of a suitable co-catalyst and/or solvent, and contacting the activated complex with one or more monomers. The polymerization or oligomerization may be carried out under suitable reaction conditions to polymerize or oligomerize the monomer. In an embodiment, the monomer is an olefin having 2 to 20 carbon atoms. In an embodiment the monomer is an olefin having 2 to 3 carbon atoms. In yet another embodiment the monomer is ethylene. The polymerization or oligomerization is performed under conditions suitable for polymerizing or oligomerizing monomer. In an embodiment, such a polymerization results in the production of polyethylene. In some embodiments, ethylene is polymerized to alpha-olefin oligomers having from about 4 to about 30 carbon atoms. In other embodiments, ethylene is polymerized to produce a reactor effluent that comprises greater than about 50 weight percent alpha-olefins. In yet another embodiment, the oligomerization produces a reactor effluent including greater than about 50 weight percent oligomers having from about 4 to about 30 carbon atoms. In some embodiments the oligomers comprise alpha olefins. In an embodiment, the catalyst produces linear α-olefins with a K value of less than about 0.7. In other embodiments, the oligomerization process produces 1-hexene having at least about 98.9 percent purity. In additional embodiments, the ethylene oligomerization process produces less than about 20 weight percent solids. The catalyst yield may be verified by quantifying the amount of solids produced in the oligomerization reaction and comparing this amount to the predicted amount.

In some embodiments, the hexadentate bimetallic complexes are activated with a co-catalyst and utilized to oligomerize ethylene. In some embodiments, the ethylene oligomerization process produces a content of oligomers having greater than 18 carbon atoms no higher than 20 weight percent above the content of oligomers having greater than 18 carbon atoms predicted by a Schulz-Flory constant K. In other embodiments, the ethylene oligomerization process produces a purity of oligomers having 14 carbon atoms equal to or greater than about 94 weight percent 1-tetradecene. In yet further embodiments, the ethylene oligomerization process produces a content of oligomers having greater than 18 carbon atoms no higher than 20 weight percent above the content of oligomers having greater than 18 carbon atoms predicted by a Schulz-Flory constant K, and a purity of oligomers having 14 carbon atoms equal to or greater than about 94 weight percent 1-tetradecene. In another embodiment, the ethylene oligomerization process produces a content of oligomers comprising: a Schulz-Flory K value less than about 0.7; less than about 20 weight percent compounds having greater than or equal to 20 carbon atoms; and 1-hexene having at least about 98.9 weight percent purity. In yet another embodiment, the ethylene oligomerization process produces an alpha olefin product comprising: a Schulz-Flory K value of less than about 0.7; less than about 20 weight percent solids; and 1-hexene having at least about 98.9 weight percent purity.

The hexadentate bimetallic complexes provided herein may be further employed in preparing a polymerization or oligomerization catalyst system. Preparing the polymerization or oligomerization catalyst system may involve generating a metal alkyl or metal hydride species, and contacting the catalyst system including the hexadentate bimetallic complex and the metal alkyl or metal hydride species with one or more monomers under suitable reaction conditions to polymerize the monomer. In other embodiments, the hexadentate bimetallic complex is activated by an aluminum alkyl, Lewis acid, aluminoxane, or combination thereof. In some embodiments, the hexadentate bimetallic complex produces an oligomerization catalyst system that is substantially free of polymer-forming active sites. In other embodiments, the hexadentate bimetallic complex produces an ethylene oligomerization catalyst system that is substantially free of polymer-forming active sites.

In some embodiments the metal alkyl comprises an alkyl aluminum compound. In further embodiments, the alkylaluminum compound comprises a trialkylaluminum compound, an aluminoxane, or combination thereof. In yet further embodiments, the alkylaluminum compound comprises trialkylaluminum, methyl-aluminoxane (MAO), MMAO, or combinations thereof.

In embodiments of the method for preparing a polymerization catalyst, olefins may or may not be present during generation of a metal alkyl or metal hydride species. The metal hydride or metal alkyl species may be generated by a Lewis acid or a combination of a Lewis acid and alkylating agent. An example of a Lewis acid is $(C_6H_5)_3B$. An example of a metal hydride is $NaBH_4$. Alternatively, the metal hydride or metal alkyl species may be generated by an alkyl aluminum compound such as, for example, triethylaluminum (TEA). In another embodiment, the metal hydride or metal alkyl species is generated by an alkyl aluminoxane such as a methyl-aluminoxane (MAO). The metal hydride or metal alkyl species may alternatively be generated by a combination of Lewis acids, alkyl aluminums, or alkyl aluminoxanes.

EXAMPLES

Example 1

25.2 g (155 mmol) of 2,6-diacetylpyridine were dissolved in ethanol in an open beaker at ambient temperature. 21.7 ml (155 mmol) of 2,4,6-trimethylaniline was then added to the beaker, followed by the addition of several drops of acetic acid. After one day, yellow crystals of the compound of structure 2 began to form, and were collected and washed with cold ethanol. Additional crops were collected without crystallization over several days and combined, for a total yield of 40.06 g (93%). The product was identified as the compound having structure E1, which is an embodiment of structure 2, by $^1H$ NMR. $^1H$ NMR (CDCl$_3$) δ8.58 (d, 1H, H$_{py}$), δ8.12 (d, 1H, H$_{py}$) δ7.90 (t, 1H, H$_{py}$) δ6.90 (s, 2H, H$_{mes}$), δ2.80 (s, 3H, acylne CH$_3$), δ2.30 (s, 3H, imine CH$_3$), δ2.23 (s, 3H, p-CH$_3$), δ2.00 (s, 6H, o-CH$_3$).

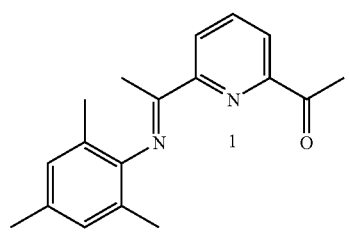

Example 2

10.0 g (61 mmol) of 2,6-diacetylpyridine and 6.24 g (25 mmol) of 4,4'-methylenebis(2,6-dimethylaniline) were dissolved in ethanol in an open beaker at ambient temperature. The beaker was covered with a watch glass overnight, after which time a very small amount of suspended cloudy precipitate had begun to form. The beaker was then left uncovered for four days, after which time a light yellow crystalline solid was collected and washed with ethanol. Successive crops were collected in the same manner, combined, and identified as the compound having structure E2, an embodiment of structure 18, by $^1H$ NMR. The total yield was 12.18 g (91%). $^1H$ NMR (CDCl$_3$) δ8.58 (d, 2H, H$_{py}$) δ8.14 (d, 2H, H$_{py}$) δ7.94 (t, 2H, H$_{py}$) δ6.96 (s, 4H, H$_{aryl}$), δ3.88 (s, 2H, CH$_2$), δ2.80 (s, 6H, ketone CH$_3$), δ2.26 (s, 6H, imine CH$_3$), δ2.03 (s, 12H, aryl CH$_3$).

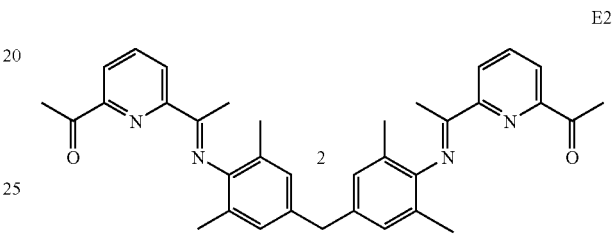

Example 3

1.0 g (3.57 mmol) of the compound having structure E1 and 0.34 g (1.42 mmol) of 4,4'-ethylenedi-m-toluidine were dissolved in 25 ml of anhydrous toluene under inert conditions. 10 mg of p-toluenesulfonic acid were added, and the reaction was heated at reflux for 5 hours. The reaction was allowed to cool, and was filtered to remove a small amount of dark residue. The toluene was removed in vacuo, and ethanol was added. The insoluble yellow solid was isolated by filtration and washed with ethanol. Additional crops were collected from the filtrate for a total yield of 426 mg (39% yield), which was identified as the compound structure E3 by $^1H$ NMR (chemical shifts are listed in Example 4).

Example 4

1.75 g (6.25 mmol) of the compound having structure E1 and 0.60 g (2.5 mmol) of 4,4'-ethylenedi-m-toluidine were dissolved in 25 ml of anhydrous toluene under inert conditions. 1.0 g of 4A molecular sieves and 0.2 g of silica/alumina catalyst support were then added, and the reaction was heated at 35° C. for 20 hours. The reaction was then filtered, the remaining solids were washed with toluene, and the filtrates were combined. The toluene was removed in vacuo, and the remaining solid was washed thoroughly with hot methanol to remove the unreacted starting materials. 1.03 g (54% yield) of yellow product was isolated and identified as the compound having structure E3 by $^1H$ NMR. $^1H$ NMR (CDCl$_3$) δ8.44 (d, 2H, H$_{py}$) δ8.36 (d, 2H, H$_{py}$), δ7.88 (t, 2H, H$_{py}$) δ7.15 (d, 2H, aryl H$_{linker}$), δ6.89 (s, 4H, H$_{mes}$), δ6.68 (s, 2H, aryl H$_{linker}$), δ6.63 (d, 2H, aryl H$_{linker}$), δ2.91 (s, 4H, CH$_2$), δ2.43 (s, 6H, CH$_3$), δ2.32 (s, 6H, CH$_3$), δ2.30 (s, 6H, CH$_3$), δ2.25 (s, 6H, CH$_3$), 2.01 (2, 12H, mes. CH$_3$).

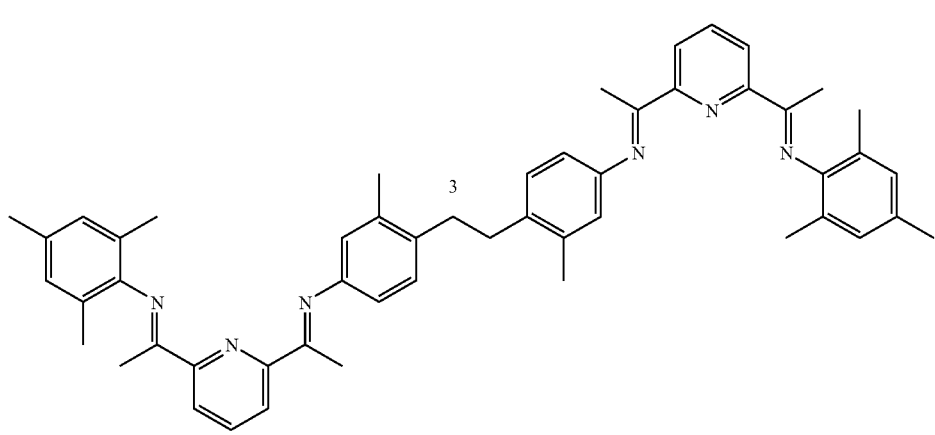

E3

Example 5

4.24 g (15.1 mmol) of the compound having structure E1 and 1.42 g (7.2 mmol) of 4,4'-methylenedianiline were dissolved in 50 ml of anhydrous toluene under inert conditions. 4A molecular sieves and 3 drops of concentrated sulfuric acid were then added, and the reaction was allowed to sit overnight. After sitting overnight, 4 more drops of sulfuric acid were added, along with more molecular sieves. The reaction was heated to reflux for 3 hours, after which time the reaction was allowed to cool and the toluene was removed in vacuo. Ethanol was added, and the reaction was placed in a freezer at 0° C. overnight. A yellow precipitate was isolated, washed with ethanol, and then recrystallized from a cyclohexane/ethanol mixture. The product (0.36 g, 6.6% yield) was identified as having structure E4 by $^1$H NMR (chemical shifts are listed in Example 6).

Example 6

1.75 g (6.25 mmol) of the compound having structure E1, 496 mg (2.5 mmol) of 4,4'-methylenedianiline, 25 ml of anhydrous toluene, 1.0 g of 4A molecular sieves, and 0.2 g of silica/alumina catalyst support were added to a flask under inert conditions. Stirring was begun, and the reaction was heated at 35° C. for 20 hours. The solids were then removed by filtration, the remaining solids were washed with toluene, the filtrates were combined, and the toluene was removed in vacuo. The remaining yellow residue was washed with methanol. The remaining solid was identified by $^1$H NMR as mostly the compound having structure E1, but a second crop collected from the filtrate was isolated and identified as the compound having structure E4 (228 mg, 13% yield) by $^1$H NMR. $^1$H NMR (CDCl$_3$) δ8.42 (d, 2H, H$_{py}$) δ8.34 (d, 2H, H$_{py}$) δ7.85 (t, 2H, H$_{py}$) δ7.21 (d, 4H, aryl H$_{linker}$), δ6.89 (s, 4H, H$_{mes}$), δ6.78 (d, 4H, aryl H$_{linker}$), δ4.00 (s, 2H, CH$_2$), δ2.42 (s, 6H, CH$_3$), δ2.30 (s, 6H, CH$_3$), δ2.23 (s, 6H, CH$_3$), 2.01 (2, 12H, mes. CH$_3$).

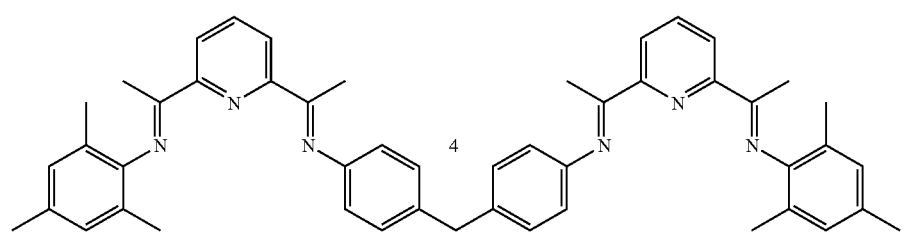

E4

Example 7

3.00 g (5.50 mmol) of the compound having structure E2, 2.63 ml (16.5 mmol) of 4-t-butylaniline, and 10 mg of p-toluenesulfonic acid were dissolved in 50 ml of anhydrous toluene under inert conditions. The reaction flask was fitted with a reflux condenser and heated at reflux for one hour, then at 90° C. overnight. The reaction was allowed to cool to 25° C., then filtered to remove a small amount of dark residue. The solvent was removed in vacuo to give an oil, and ethanol was added. A yellow precipitate (1.04 g) was collected by filtration and could not be conclusively identified by $^1$H NMR.

Example 8

1.36 g (2.5 mmol) of the compound having structure E2, 0.95 ml (6 mmol) of 4-t-butylaniline, 20 ml of anhydrous toluene, 1.0 g of 4A molecular sieves, and 0.2 g of silica/alumina catalyst support were added to a flask under inert conditions. Stirring was begun, and the reaction was heated at 35° C. for 20 hours. The solids were then removed by filtration, the remaining solids were washed with toluene, the filtrates were combined, and the toluene was removed in vacuo. The remaining sticky yellow residue was washed by stirring it methanol at 65° C. until a fine suspended powder formed. The solid was isolated and identified as the compound having structure E5 (665 mg, 33% yield) by $^1$H NMR. $^1$H NMR (CDCl$_3$) δ8.42 (d, 2H, H$_{py}$) δ8.35 (d, 2H, H$_{py}$) δ7.85 (t, 2H, H$_{py}$) δ7.39 (d, 4H, aryl H$_{tBu\ ring}$), δ6.92 (s, 4H, H$_{aryl}$), δ6.79 (d, 4H, aryl H$_{tBu\ ring}$), δ3.86 (s, 2H, CH$_2$), δ2.82 (s, 6H, ketone CH$_3$), δ2.25 (s, 6H, imine CH$_3$), δ2.03 (s, 12H, aryl CH$_3$), δ1.33 (s, 18H, t-Bu).

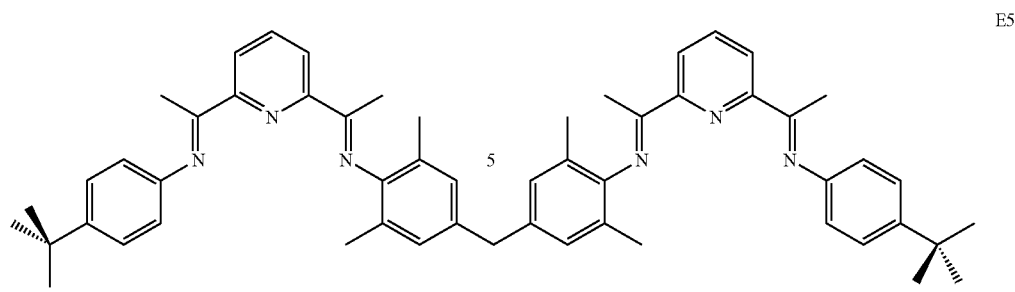

E5

Example 9

1.000 g (1.31 mmol) of the compound having structure E3 and 0.521 g of FeCl$_2$.4H$_2$O (2.62 mmol) were added to a flask in a substantially oxygen- and moisture-free environment. A stirring bar was added, followed by the addition of 25 ml of anhydrous THF. The reaction was stirred for 16 h, followed by precipitation of the product with pentane, filtration, and washing with ether and pentane. 1.33 g of blue powder was isolated (96% yield based on proposed structure E6 with two molecules of H$_2$O). The blue power was submitted for elemental analysis (Atlantic Microlabs, Norcross, Ga.), and the following values were determined: Analytical Calculated for C$_{52}$H$_{60}$N$_6$Fe$_2$Cl$_4$O$_2$ having structure E6: C, 59.22; H, 5.73; N, 7.97; O, 3.03. Found: C, 57.76; H, 5.50; N, 7.51; O, 3.68. Note that the empirical formula allows for two equivalents of H$_2$O. Example 26 demonstrates a second method for preparing the compound having structure E6. Example 33 demonstrates a third method for producing the compound having structure E6.

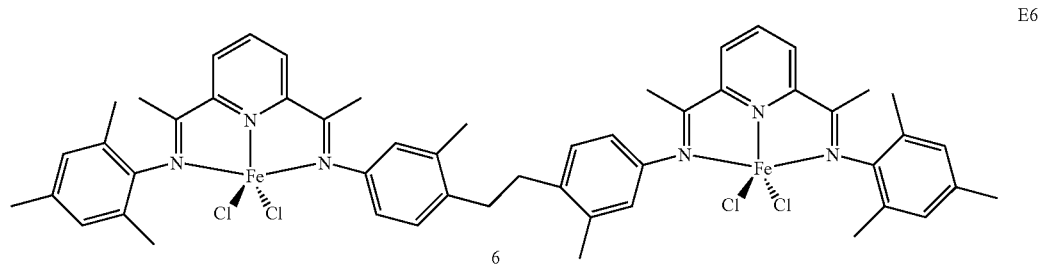

E6

Example 10

1.000 g (1.24 mmol) of the compound having structure E5 and 0.494 mg (2.48 mmol) of $FeCl_2.4H_2O$ were reacted together in the manner described in Example 9. 1.35 g (99% yield based on proposed structure E7 with two molecules of $H_2O$) of blue powder was isolated. Analytical Calculated for $C_{55}H_{65}N_6Fe_2Cl_4O_2$ having structure E7: C, 60.29; H, 5.98; N, 7.67; O, 2.92. Found: C, 59.47; H, 5.92; N, 7.17; O, 3.69. Example 11 demonstrates a second method for preparing the compound having structure E7.

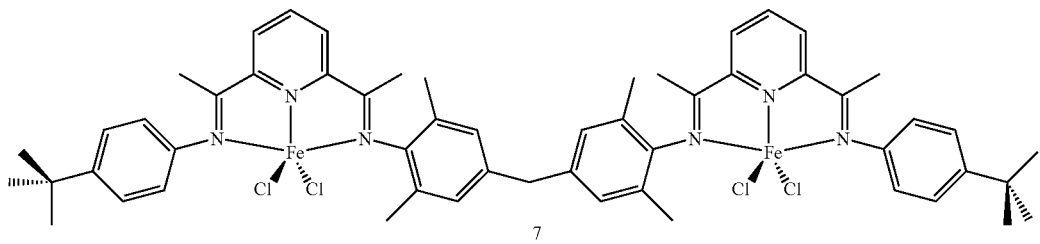

E7

Examples 11-15

The following procedure was used to prepare compounds having structures E7-11. Table 2 contains analytical data for the compounds prepared. General Procedure: 500 mg (0.92 mmol) of the compound having structure E2, 366 mg (1.84 mmol) of $FeCl_2.4H_2O$, 15 ml of anhydrous n-butanol, and 2.76 mmol of the appropriate aniline were added to a small vial with a stir bar in a substantially oxygen- and moisture-free environment. The vial was sealed, stirring was begun, and the reaction was heated to 80° C. for 18 h. The reaction was allowed to cool to ambient temperature, and the iron complex was precipitated by the addition of pentane. The reaction was filtered, and the isolated solid was washed with pentane. Mass spectrometry analyses were performed at the University of Michigan on a Waters Autospec magnetic sector mass spectrometer, using 0.05 mg/ml solutions of the compounds in methanol. The elemental analyses allowed for two equivalents of $H_2O$ per molecule of complex.

TABLE 2

| Ex. | Aniline | Compound Formed | Yield (g, %) | Calc'd Elemental Analysis % | Found Elemental Analysis % | Mass Spec. (ES+) m/z |
|---|---|---|---|---|---|---|
| 11 | 4-isopropylaniline | 7 E7 | 0.84 g, 83% yield | C: 60.24 H: 6.07 N: 7.66 | 61.38 5.82 7.84 | 897 [M − FeCl₃]+ |
| 12 | 4-C₁₄H₂₉-aniline | 8 E8 | 0.78 g, 63% yield | C: 65.41 H: 7.76 N: 6.10 | 66.42 7.55 6.24 | 1178 [M − FeCl₃]+ |
| 13 | 3,5-dimethoxyaniline | 9 E9 | 0.92 g, 91% yield | C: 55.46 H: 5.29 N: 7.61 | 56.10 5.40 7.53 | 905 [M − FeCl₃]+ |

TABLE 2-continued

| Ex. | Aniline | Compound Formed | Yield (g, %) | Calc'd Elemental Analysis % | Found Elemental Analysis % | Mass Spec. (ES+) m/z |
|---|---|---|---|---|---|---|
| 14 | 3,5-dimethylaniline | 10 E10 | 0.87 g, 92% yield | C: 58.87 H: 5.62 H: 8.08 | 59.06 5.55 8.09 | 841 [M−FeCl₃]+ |
| 15 | 4-trifluoromethylaniline | 11 E11 | 0.81 g, 78% yield | F: 10.17 | 8.96 | 1085 [M−FeCl₃]+ |

Examples 16-22

The following procedure was used to test the compounds having structures E7-11, prepared in examples 11-15, for the oligomerization of ethylene. Table 3 contains the results of these oligomerization reactions. General Procedure: The bimetallic complex (prepared as a standard solution in methylene chloride, or as a homogeneous mixture in biphenyl) was placed in an NMR tube in a substantially oxygen- and moisture-free environment. If the biphenyl mixture was used, about 0.5 ml of methylene chloride was added to the tube. The NMR tube was then sealed and affixed (using copper wire) to the internal stirring mechanism of a 500 ml stainless steel autoclave, such that the beginning of stirring would break the NMR tube and release the contents into the reactor. The reactor was then evacuated and charged with 100 ml of anhydrous n-heptane which contained the aluminum co-catalyst (TEA=triethylaluminum, or MMAO=MMAO 3A made by Akzo) for the given reaction. The reactor was then pressurized with 30 bars (450 psig) of ethylene, and stirring was begun to initiate the reaction. The reactions were run for 30 min, during which time the ethylene pressure was held constant and the reaction temperature was controlled by internal cooling coils. Each reaction was begun at about 30° C.; the temperatures reported in Table 3 represent the maximum temperature achieved during the course of the reaction. At the end of each reaction, the ethylene was slowly vented, and the products were analyzed by gas chromatography, using the solvent (n-heptane) as the internal standard. The Schulz-Flory constant K was used to estimate the total amount of product made. The high activity of the catalysts, the high purity of the products, the absence of polymeric byproducts, and the analytical data (mass spectrometry and elemental analyses) demonstrate that the desired bimetallic complexes are formed in high yield with acceptable purities.

TABLE 3

| Ex. | Cmpd | Amt. (mg) | TEA Al:Fe ratio (mol:mol) | MMAO Al:Fe ratio (mol:mol) | $T_{max}$ (° C.) | K (mol $C_{12}$/mol $C_{10}$) | Yield (g) | Prod. (g prod/g Fe complex) | % 1-hexene in $C_6$ products | % 1-octene in $C_8$ products | % 1-decene in $C_{10}$ products |
|---|---|---|---|---|---|---|---|---|---|---|---|
| 16 | E7 | 0.20 | 1200 | 300 | 65 | 0.687 | 40.0 | 200,000 | 99.0 | 98.3 | 98.0 |
| 17 | E8 | 0.15 | 1200 | 600 | 86 | 0.615 | 37.8 | 252,000 | 99.0 | 97.8 | 97.3 |
| 18 | E8 | 0.20 | 1200 | 600 | 89 | 0.631 | 56.6 | 283,000 | 99.1 | 98.3 | 97.6 |
| 18 | E9 | 0.20 | 1200 | 300 | 93 | 0.670 | 32.1 | 161,000 | 98.8 | 98.3 | 97.8 |
| 20 | E9 | 0.20 | 1200 | 600 | 86 | 0.695 | 44.0 | 220,000 | 99.0 | 98.6 | 98.1 |
| 21 | E10 | 0.20 | 1200 | 600 | 82 | 0.664 | 52.6 | 263,000 | 99.2 | 98.5 | 98.0 |
| 22 | E11 | 0.20 | 1200 | 600 | 81 | 0.700 | 52.2 | 261,000 | 99.4 | 99.0 | 98.7 |

% Polymer = % of total product yield with molecular weight greater than 2000.

% Solids = % of total product yield that is insoluble in n-heptane.

% Solids predicted = Total product yield predicted to be in the $C_{20}^+$ fraction.

Examples 23-27

The following procedure was used to prepare the compounds having structures E6, E12, E13, E14, and E15. Table 4 contains analytical data for the compounds prepared. General Procedure: 800 mg (2.86 mmol) of the compound having structure E1, 1.29 mmol of the appropriate diamine compound, 2.58 mmol of $FeCl_2 \cdot 4H_2O$, and 20 ml of anhydrous THF were added to a small vial with a stir bar in a substantially oxygen- and moisture-free environment. The vial was sealed, stirring was begun, and the reaction was heated to 60° C. for 18 h. The reaction was allowed to cool to ambient temperature, and the iron complex was precipitated by the addition of pentane. The reaction was filtered, and the isolated solid was washed with pentane. Elemental analyses were performed at Atlantic Microlabs. The calculated values assume two equivalents of $H_2O$ per mole of bimetallic complex.

TABLE 4

| Ex. | Diamine | Compound Formed | Yield (g, %) | Calc'd Elemental Analysis % | Found Elemental Analysis % |
|---|---|---|---|---|---|
| 23 | (4,4'-methylenedianiline structure) | 12 E12 | 1.21 g, 89% yield | C: 58.13 H: 5.38 N: 8.30 | 56.70 5.37 7.91 |
| 24 | (3,3'-methylenedianiline structure) | 13 E13 | 1.16 g, 88% yield | C: 58.13 H: 5.38 N: 8.30 | 57.50 5.06 8.11 |
| 25 | (4,4'-(hexafluoroisopropylidene)dianiline structure) | 14 E14 | 1.18 g, 79% yield | F: 9.93 | 8.74 |

TABLE 4-continued

| Ex. | Diamine | Compound Formed | Yield (g, %) | Calc'd Elemental Analysis % | Found Elemental Analysis % |
|---|---|---|---|---|---|
| 26 | (structure with H₂N and NH₂ groups on methylated biphenylethane) | 6 E6 | 1.33 g, 96% yield | C: 59.22 H: 5.73 N: 7.97 | 60.03 5.84 7.65 |
| 27 | (structure with H₂N and NH₂ groups on diphenyl ether) | 15 E15 | 1.29 g, 96% yield | C: 56.83 H: 5.17 N: 8.28 | 56.18 4.96 7.92 |

Examples 28-33

The same procedure used in examples 16-22 was used to test complexes having structures E6, E12, E13, E14, and E15 (prepared in examples 23-27) for the oligomerization of ethylene. Table 5 contains the results of these experiments.

TABLE 5

| Ex. | Cmpd | Amt. (mg) | TEA Al:Fe ratio (mol:mol) | MMAO Al:Fe ratio (mol:mol) | $T_{max}$ (°C.) | K (mol $C_{12}$/mol $C_{10}$) | Yield (g) | Prod. (g prod/g Fe complex) | % 1-hexene in $C_6$ products | % 1-octene in $C_8$ products | % 1-decene in $C_{10}$ products |
|---|---|---|---|---|---|---|---|---|---|---|---|
| 28 | E12 | 0.20 | 600 | 600 | 61 | 0.700 | 42.1 | 210,000 | 99.4 | 99.0 | 98.9 |
| 29 | E13 | 0.20 | 600 | 600 | 101 | 0.656 | 45.6 | 228,000 | 99.0 | 98.1 | 97.7 |
| 30 | E14 | 0.20 | 600 | 600 | 57 | 0.743 | 28.3 | 142,000 | 99.5 | n.d. | n.d. |
| 31 | E6 | 0.20 | 600 | 600 | 64 | 0.691 | 46.2 | 231,000 | 99.5 | 99.1 | 99.0 |
| 32 | E15 | 0.20 | 600 | 600 | 96 | 0.674 | 67.8 | 339,000 | 98.9 | 98.2 | 97.8 |
| 33 | E15 | 0.10 | 600 | 600 | 95 | 0.665 | 46.2 | 462,000 | 99.3 | 98.6 | 98.1 |

Example 34

5.03 g (18.0 mmol) of the compound having structure E1 and 3.40 g (17.1 mmol) of $FeCl_2 \cdot 4H_2O$, and 100 ml of anhydrous THF were added to a 200 ml flask with a stir bar in a substantially oxygen- and moisture-free environment. The reaction mixture was stirred for 2 days. Pentane was added to precipitate the complex, which was then isolated by filtration and washed with pentane (7.8 g). Anal. Calcd for $C_{18}H_{20}N_2OFeCl_2$ having structure E16: C, 53.10; H, 4.95; N, 6.88. Found: C, 49.32; H, 5.8; N, 5.63. These data are consistent with the presence of two equivalents of $H_2O$.

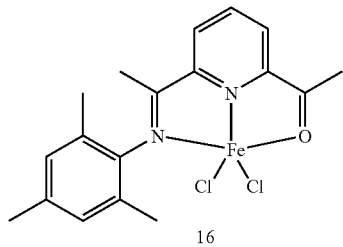

E16

Example 35

1.00 g (2.09 mmol, assuming 1 molecule of THF per molecule of the compound having structure E16) of the compound having structure E16, 0.95 mmol of the dianiline, 15 ml of anhydrous THF, and a stir bar were added together in a small vial in an environment substantially free of oxygen and moisture. The vial was sealed and heated, with stirring, for 16 h at 60° C. The reaction was allowed to cool to ambient temperature, and the vial contents were poured into 50 ml of pentane to precipitate the product. The product was isolated by filtration and further washed with pentane.

TABLE 6

| Ex. | Compound Formed | Yield (g, %) | Calc'd Elemental Analysis % | Found Elemental Analysis % |
|---|---|---|---|---|
| 35 | 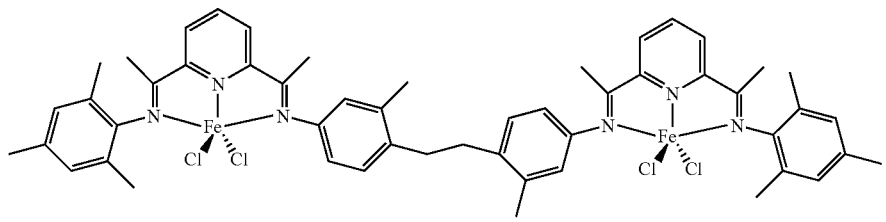<br>E6 | 1.05 g, 93% yield | C: 61.32<br>H: 5.54<br>N: 8.25 | 52.43<br>5.05<br>7.00 |

Example 36

The same procedure used in examples 16-22 was used to test complexes having structure E6 (prepared in example 35) for the oligomerization of ethylene. Table 7 contains the results of this experiment.

TABLE 7

| Ex. | Cmpd | Amt. (mg) | TEA Al:Fe ratio (mol:mol) | MMAO Al:Fe ratio (mol:mol) | $T_{max}$ (°C.) | K (mol $C_{12}$/mol $C_{10}$) | Yield (g) | Prod. (g prod/g Fe complex) | % 1-hexene in $C_6$ products | % 1-octene in $C_8$ products | % 1-decene in $C_{10}$ products |
|---|---|---|---|---|---|---|---|---|---|---|---|
| 36 | E7 | 0.20 | 1200 | 600 | 65 | 0.687 | 37.7 | 189,000 | 99.5 | 99.0 | 99.0 |

The particular embodiments disclosed herein are illustrative only, as the invention may be modified and practiced in different but equivalent manners apparent to those skilled in the art having the benefit of the teachings herein. For example, while the embodiments have been described in terms of a method for preparing hexadentate bimetallic complexes from acyliminepyridine compounds and/or acyliminepyridine metal complexes, the preparation methods described herein may be applied to other hexadentate bimetallic complexes using the general class of acylimine (mono-acylimine or bis-acylimine) compounds and/or acylimine (mono-acylimine or bis-acylimine) metal complexes such that at least one imine bond is formed in the presence of a metal salt or a metal complex. Additionally, the method described herein may be applied to the synthesis of tetradentate bimetallic complexes as described in WO 01/36379, which is incorporated by reference herein, utilizing the general class of acylimine (mono-acylimine or bis-acylimine) compounds and/or acylimine (mono-acylimine or bis-acylimine) metal complexes such that at least one imine bond is formed in the presence of a metal salt or a metal complex. Use of broader terms such as comprises, includes, having, etc. should be understood to provide support for narrower terms such as consisting of, consisting essentially of, comprised substantially of, etc. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for producing a hexadentate bimetallic complex, comprising:
    (a) contacting a mono-acyliminepyridine compound, a metal salt, and a diamine to form a mixture; and,
    (b) recovering the hexadentate bimetallic complex from the mixture,
wherein the bimetallic complex has one of the following structures:

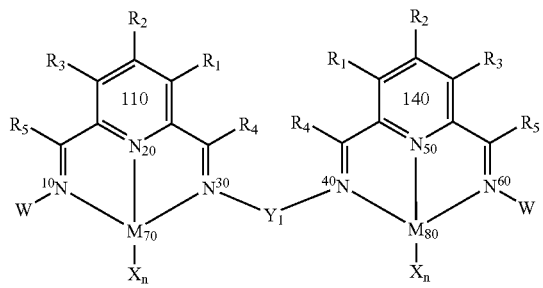

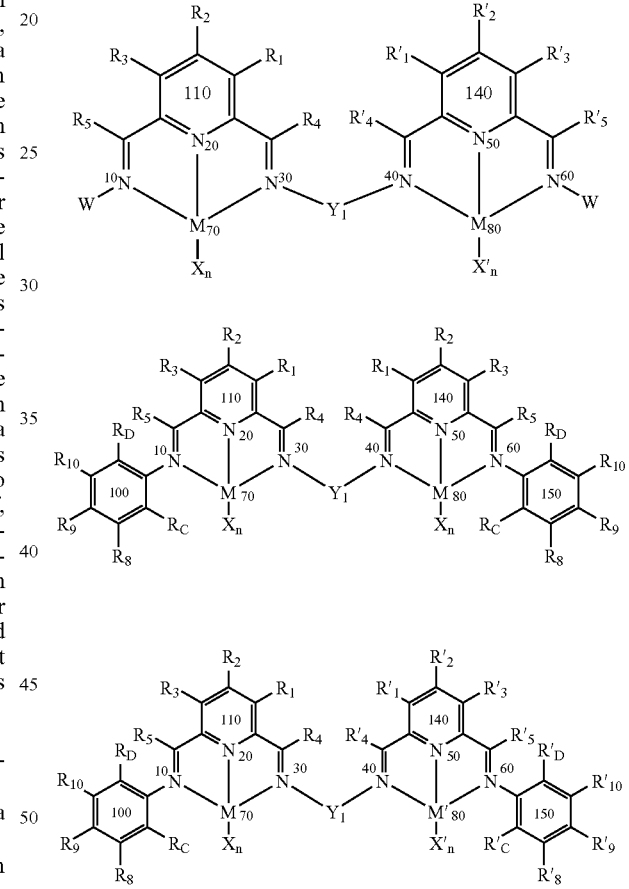

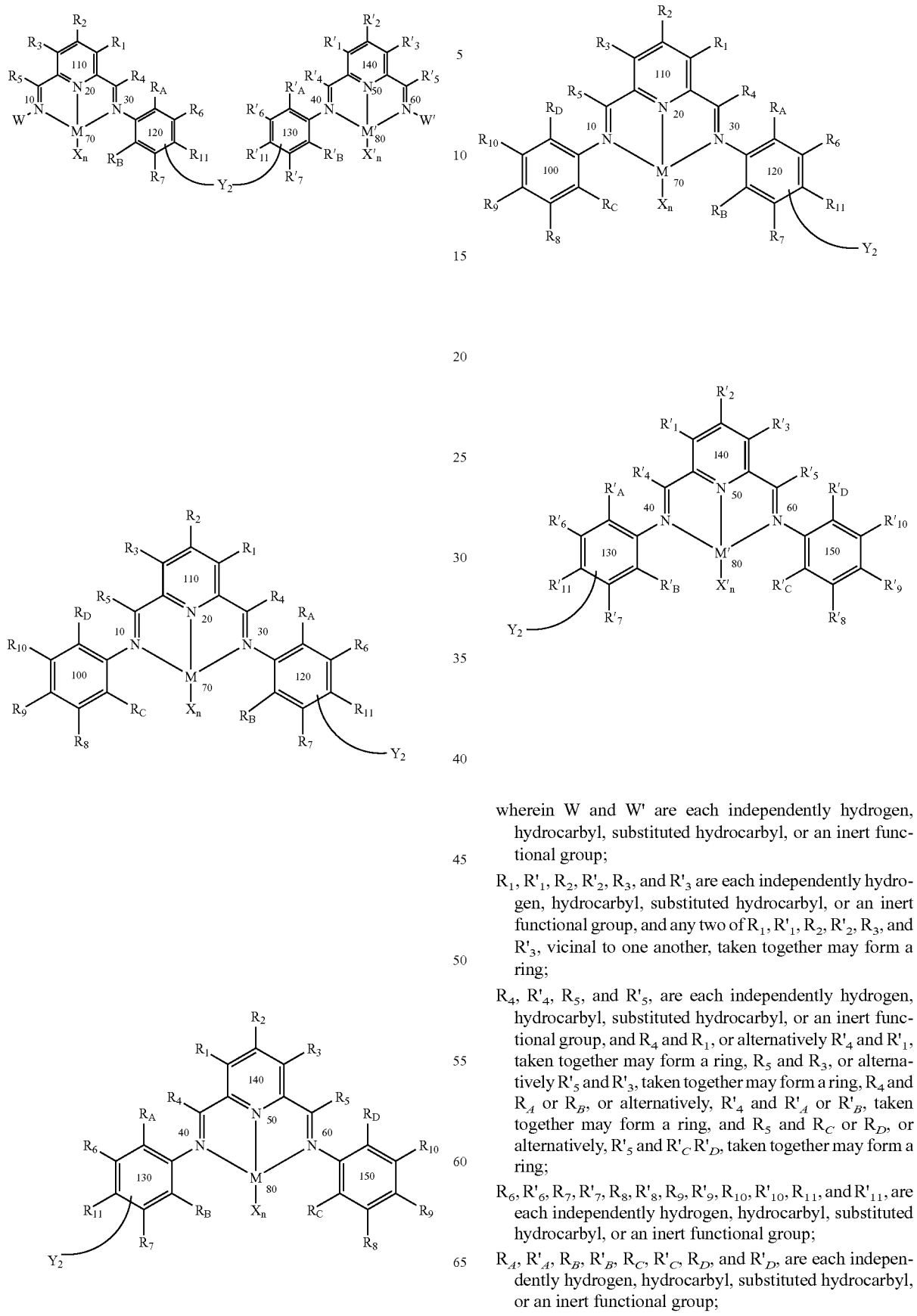

wherein W and W' are each independently hydrogen, hydrocarbyl, substituted hydrocarbyl, or an inert functional group;

$R_1$, $R'_1$, $R_2$, $R'_2$, $R_3$, and $R'_3$ are each independently hydrogen, hydrocarbyl, substituted hydrocarbyl, or an inert functional group, and any two of $R_1$, $R'_1$, $R_2$, $R'_2$, $R_3$, and $R'_3$, vicinal to one another, taken together may form a ring;

$R_4$, $R'_4$, $R_5$, and $R'_5$, are each independently hydrogen, hydrocarbyl, substituted hydrocarbyl, or an inert functional group, and $R_4$ and $R_1$, or alternatively $R'_4$ and $R'_1$, taken together may form a ring, $R_5$ and $R_3$, or alternatively $R'_5$ and $R'_3$, taken together may form a ring, $R_4$ and $R_A$ or $R_B$, or alternatively, $R'_4$ and $R'_A$ or $R'_B$, taken together may form a ring, and $R_5$ and $R_C$ or $R_D$, or alternatively, $R'_5$ and $R'_C$ $R'_D$, taken together may form a ring;

$R_6$, $R'_6$, $R_7$, $R'_7$, $R_8$, $R'_8$, $R_9$, $R'_9$, $R_{10}$, $R'_{10}$, $R_{11}$, and $R'_{11}$, are each independently hydrogen, hydrocarbyl, substituted hydrocarbyl, or an inert functional group;

$R_A$, $R'_A$, $R_B$, $R'_B$, $R_C$, $R'_C$, $R_D$, and $R'_D$, are each independently hydrogen, hydrocarbyl, substituted hydrocarbyl, or an inert functional group;

$Y_1$ and $Y_2$ represent a structural bridge between two halves of a ligand or complex, where $Y_1$ may be a bond between nitrogen group 30 and nitrogen group 40, a hydrocarbyl having from about 0 to about 30 carbon atoms, a substituted hydrocarbyl having from about 0 to about 30 carbon atoms, or an inert functional group and $Y_2$ may be a bond between aromatic rings 120 and 130, a hydrocarbyl having from about 0 to about 30 carbon atoms, substituted hydrocarbyl having from about 0 to about 30 carbon atoms, or an inert functional group;

M and M' may independently be any metal atom; and

X and X' may independently be any anion.

2. The method of claim 1, wherein the metal salt comprises, iron, cobalt, nickel, chromium, vanadium or mixtures thereof.

3. The method of claim 1, wherein a mono-acyliminepyridine compound to diamine molar ratio is about 2:1.

4. The method of claim 1, wherein a mono-acyliminepyridine compound to metal salt molar ratio is about 1:1.

5. The method of claim 1, wherein the hexadentate bimetallic complex has structure

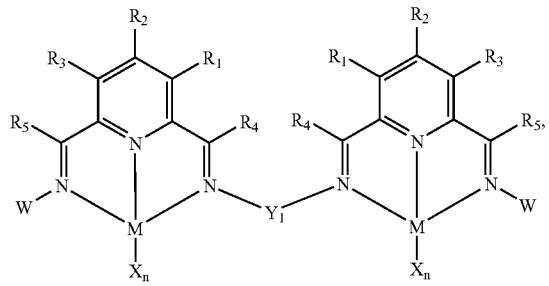

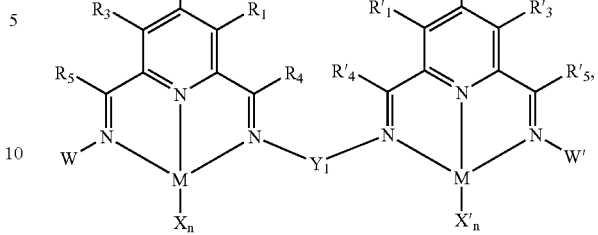

or mixtures thereof, the mono-acyliminepyridine compound has structure

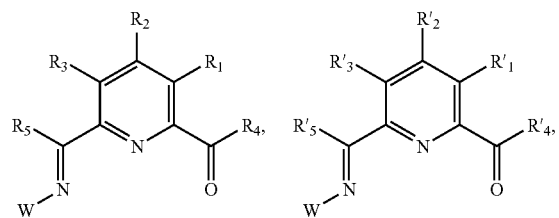

or mixtures thereof, the diamine has structure $H_2N$—$Y_1$—$NH_2$, a mono-acyliminepyridine compound to diamine molar ratio is about 2:1, and a mono-acyliminepyridine compound to metal salt molar ratio is about 1:1.

6. The method of claim 1, wherein the hexadentate bimetallic complex has structure

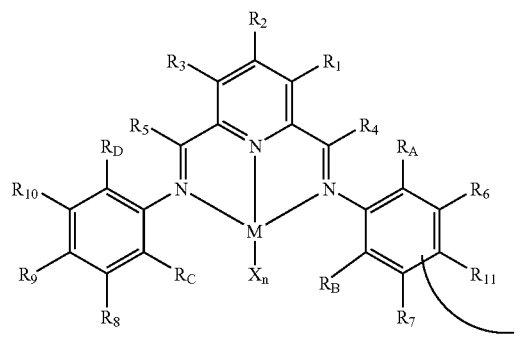 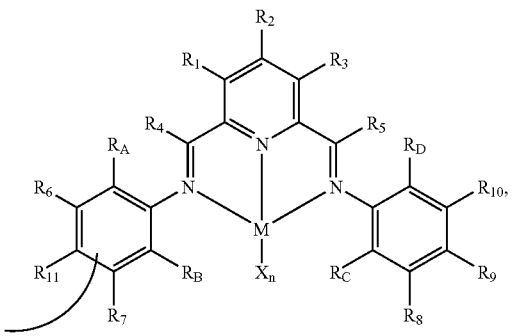

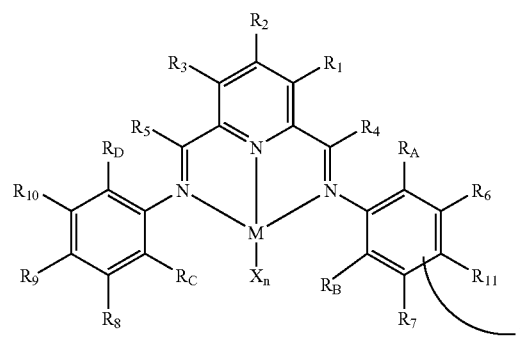 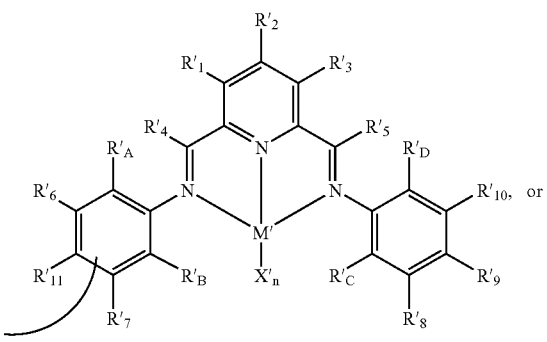, or mixtures thereof, the mono-acyliminepyridine compound has structure

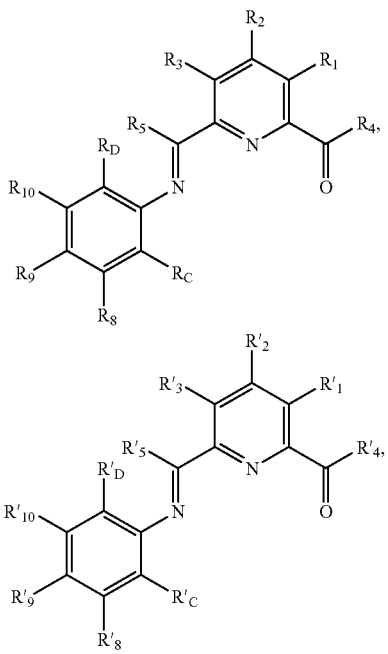

or mixtures thereof, the

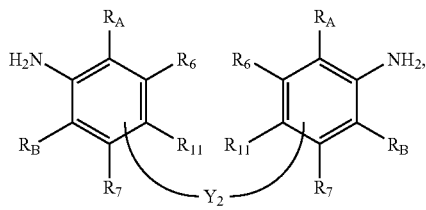

diamine has structure

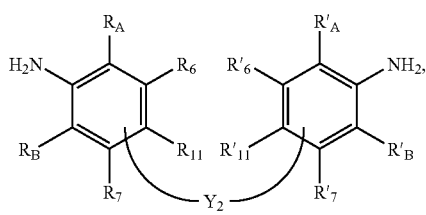

or mixtures thereof, a mono-acyliminepyridine compound to diamine molar ratio is about 2:1, and a mono-acyliminepyridine compound to metal salt molar ratio is about 1:1.

7. The method of claim 1, wherein the mono-acyliminepyridine compound is prepared by:
   (a) contacting a di-acylpyridine with a monoamine to form a first mixture; and,
   (b) recovering the mono-acyliminepyridine compound from the first mixture.

8. The method of claim 7, wherein a di-acylpyridine to monoamine molar ratio is about 1:1.

9. A method for producing a hexadentate bimetallic complex, comprising:
   (a) contacting a bis-acyliminepyridine compound, a metal salt, and a monoamine to form a mixture; and,
   (b) recovering the hexadentate bimetallic complex from the mixture, wherein the bimetallic complex has one of the following structures:

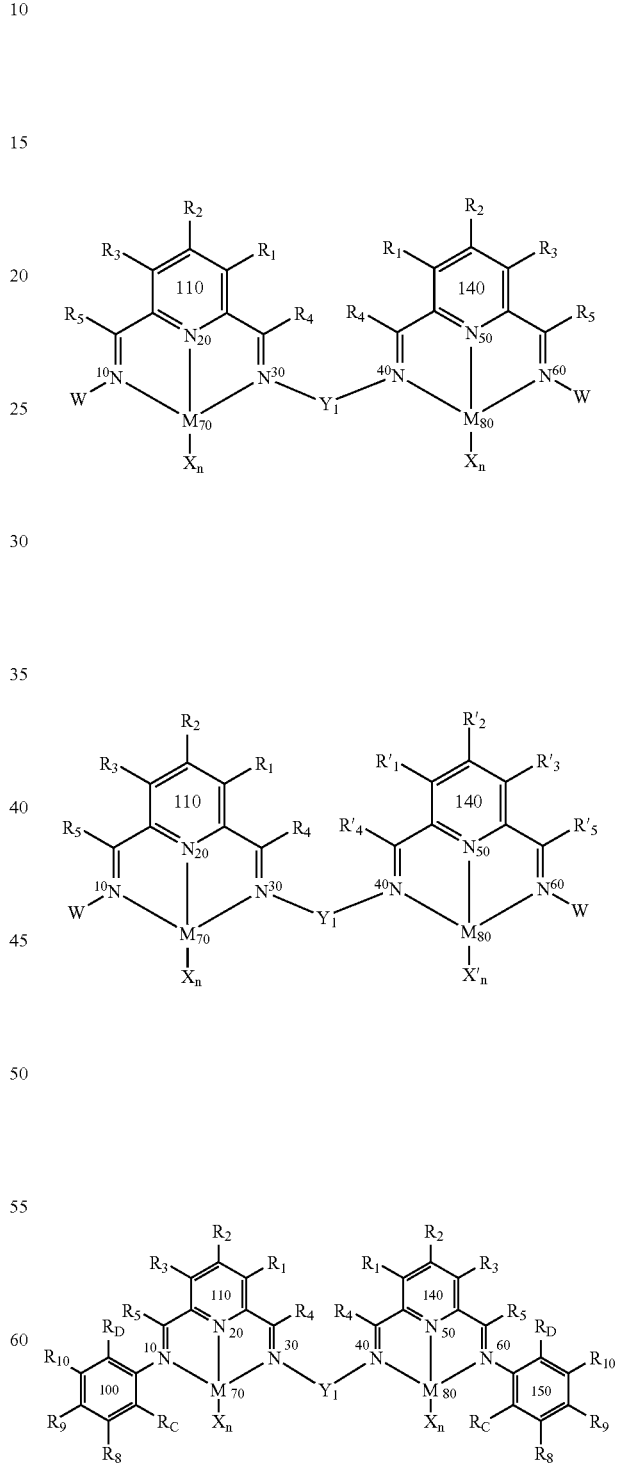

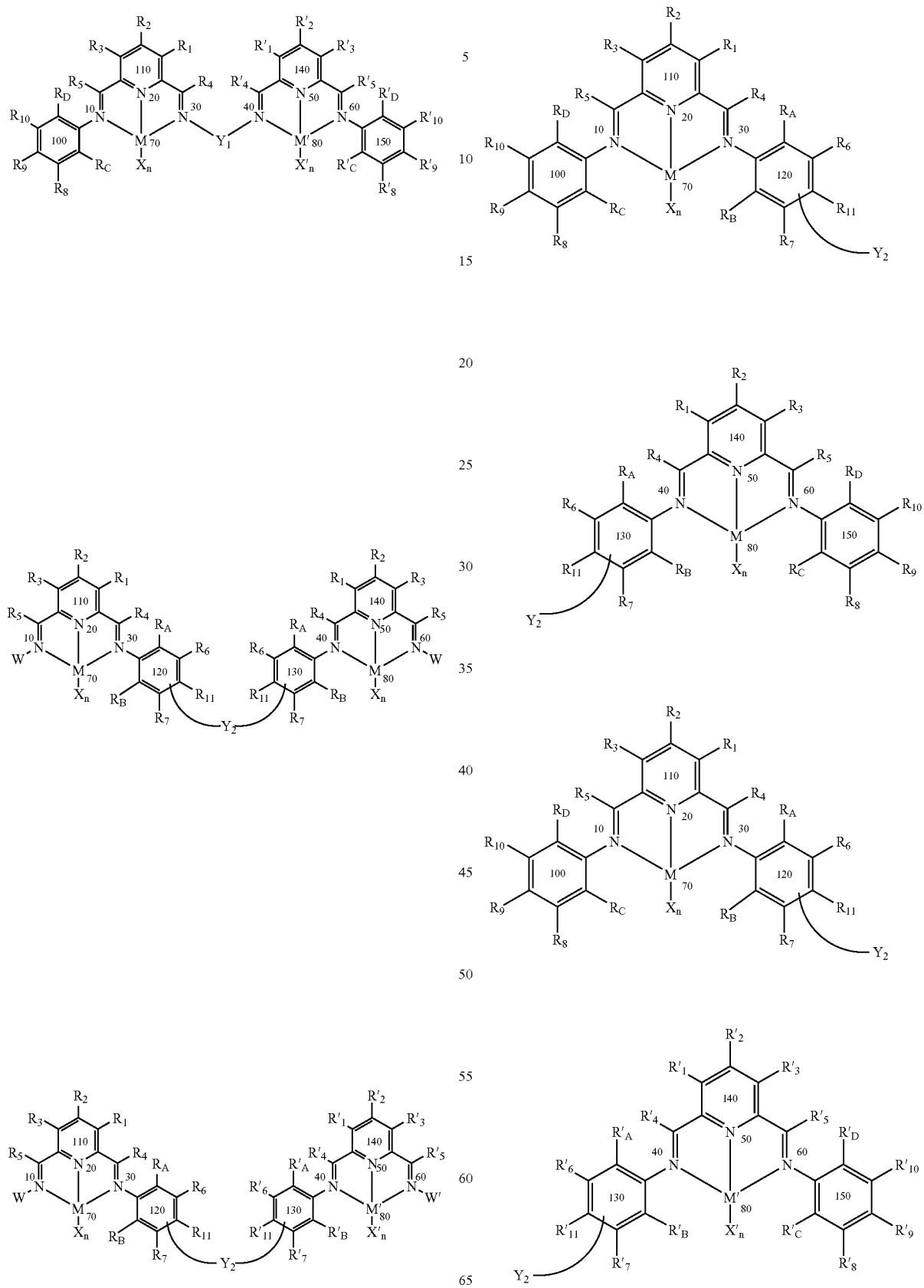

wherein W and W' are each independently hydrogen, hydrocarbyl, substituted hydrocarbyl, or an inert functional group;

$R_1$, $R'_1$, $R_2$, $R'_2$, $R_3$, and $R'_3$ are each independently hydrogen, hydrocarbyl, substituted hydrocarbyl, or an inert functional group, and any two of $R_1$, $R'_1$, $R_2$, $R'_2$, $R_3$, and $R'_3$, vicinal to one another, taken together may form a ring;

$R_4$, $R'_4$, $R_5$, and $R'_5$, are each independently hydrogen, hydrocarbyl, substituted hydrocarbyl, or an inert functional group, and $R_4$ and $R_1$, or alternatively $R'_4$ and $R'_1$, taken together may form a ring, $R_5$ and $R_3$, or alternatively $R'_5$ and $R'_3$, taken together may form a ring $R_4$ and $R_A$ $R_B$, or alternatively, $R'_4$ and $R'_A$ $R'_B$, taken together may form a ring, and $R_5$ and $R_C$ or $R_D$, or alternatively, $R'_5$ and $R'_C$ $R'_D$, taken together may form a ring;

$R_6$, $R'_6$, $R_7$, $R'_7$, $R_8$, $R'_8$, $R_9$, $R'_9$, $R_{10}$, $R'_{10}$, $R_{11}$, and $R'_{11}$, are each independently hydrogen, hydrocarbyl, substituted hydrocarbyl, or an inert functional group;

$R_A$, $R'_A$, $R_B$, $R'_B$, $R_C$, $R'_C$, $R_D$, and $R'_D$, are each independently hydrogen, hydrocarbyl, substituted hydrocarbyl, or an inert functional group;

$Y_1$ $Y_2$ represent a structural bridge between two halves of a ligand or complex, where $Y_1$ may be a bond between nitrogen group 30 and nitrogen group 40, a hydrocarbyl having from about 0 to about 30 carbon atoms, a substituted hydrocarbyl having from about 0 to about 30 carbon atoms, or an inert functional group and $Y_2$ may be a bond between aromatic rings 120 and 130, a hydrocarbyl having from about 0 to about 30 carbon atoms, substituted hydrocarbyl having from about 0 to about 30 carbon atoms, or an inert functional group;

M and M' may independently be any metal atom; and

X and X' may independently be any anion.

10. The method of claim 9, wherein a bis-acyliminepyridine compound to monoamine molar ratio is about 1:2.

11. The method of claim 9, wherein a bis-acyliminepyridine compound to metal salt molar ratio is about 1:2.

12. The method of claim 9, wherein the hexadentate bimetallic complex has structure

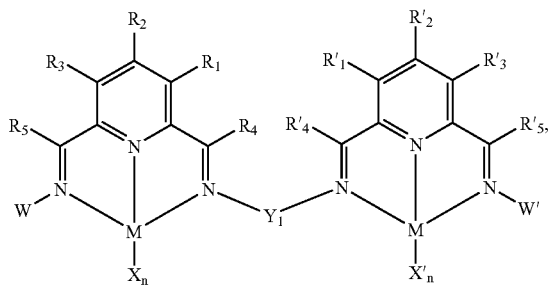

or mixtures thereof, the bis-acyliminepyridine compound has structure

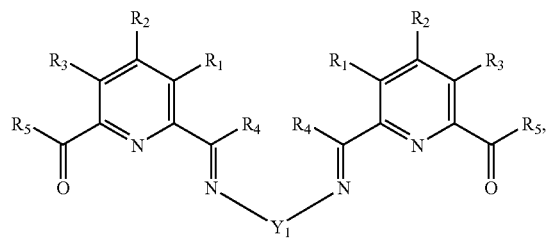

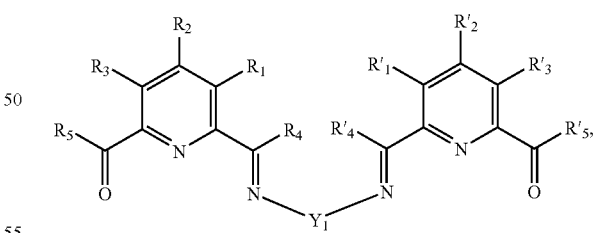

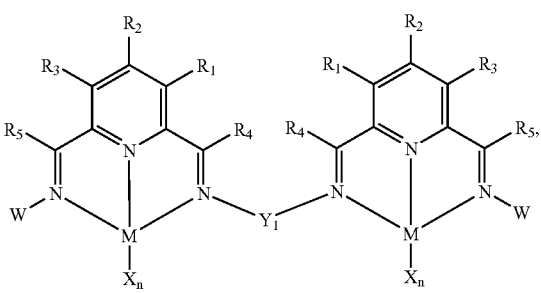

or mixtures thereof, the monoamine has structure 1, 2, or mixtures thereof, a bis-acyliminepyridine compound to monoamine molar ratio is about 1:2, and a bis-acyliminepyridine compound to metal salt molar ratio is about 1:2.

13. The method of claim 9, wherein the hexadentate bimetallic complex has structure
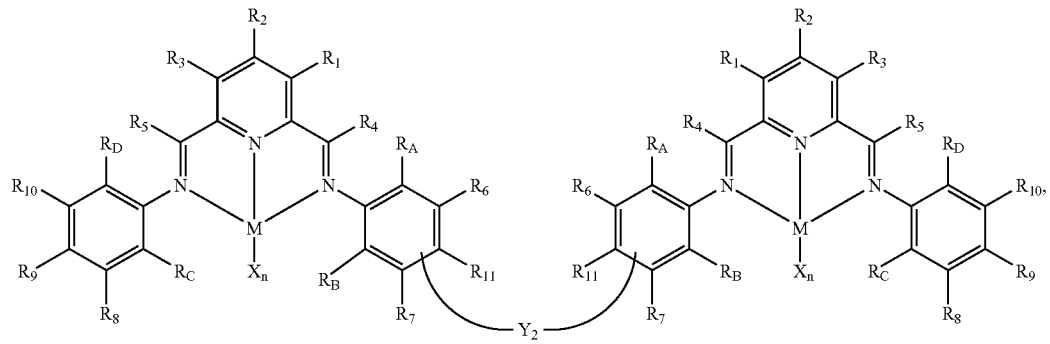
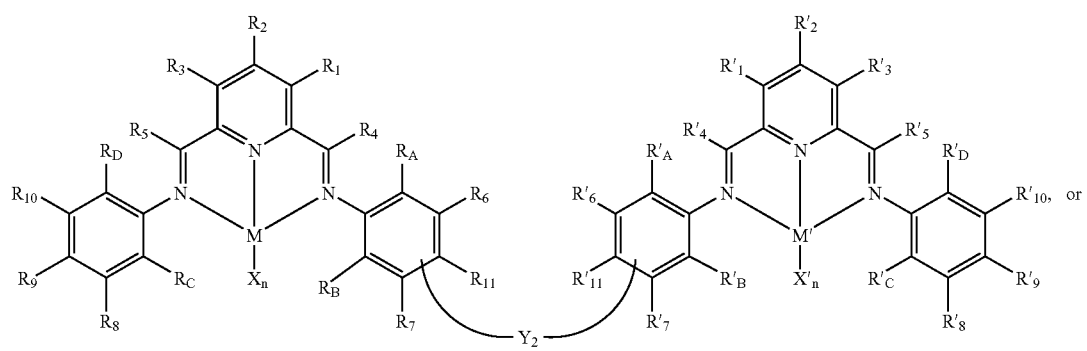
mixtures thereof, the bis-acyliminepyridine compound has structure
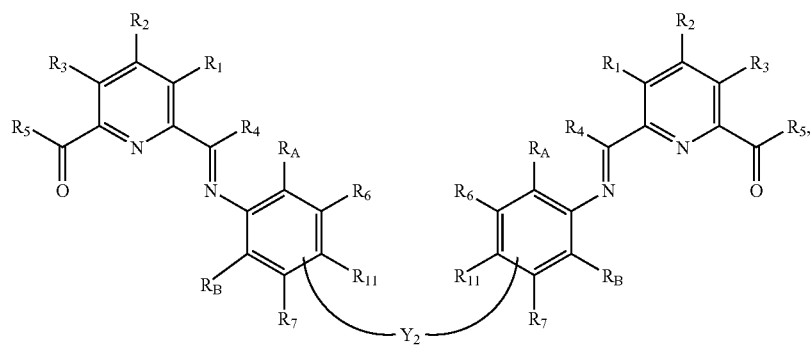

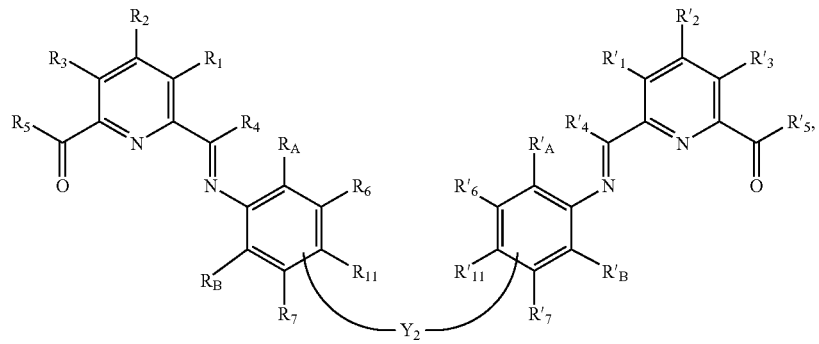

or mixtures thereof, the monoamine has structure

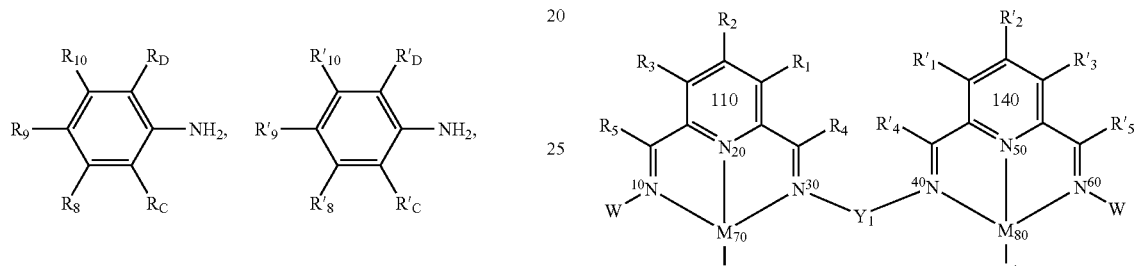

or mixtures thereof, a bis-acyliminepyridine compound to monoamine molar ratio is about 1:2, and a bis-acyliminepyridine compound to metal salt molar ratio is about 1:2.

14. The method of claim 9, wherein the bis-acyliminepyridine compound is prepared by:
   (a) contacting a di-acylpyridine with a diamine to form a first mixture; and,
   (b) recovering the bis-acyliminepyridine compound from the first mixture.

15. The method of claim 14, wherein a di-acylpyridine to diamine molar ratio is about 2:1.

16. A method for producing a hexadentate bimetallic complex, comprising:
   (a) contacting an acyliminepyridine metal complex and a first amine to form a mixture; and,
   (b) recovering the hexadentate bimetallic complex from the mixtures, wherein the bimetallic complex has one of the following structures:

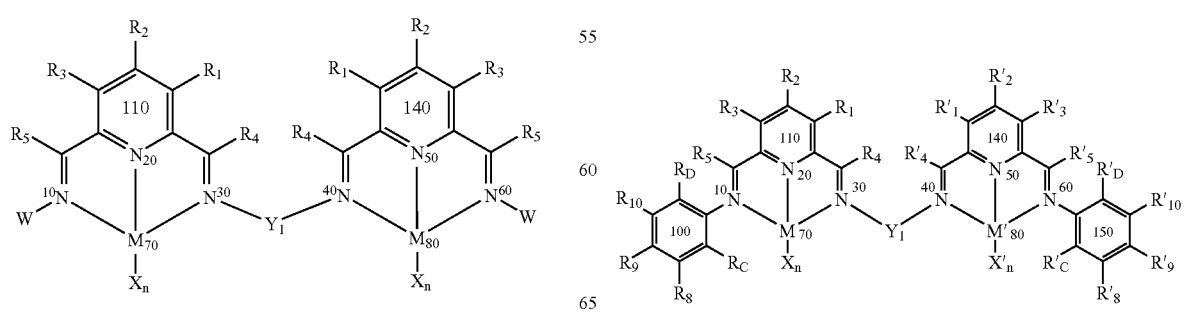

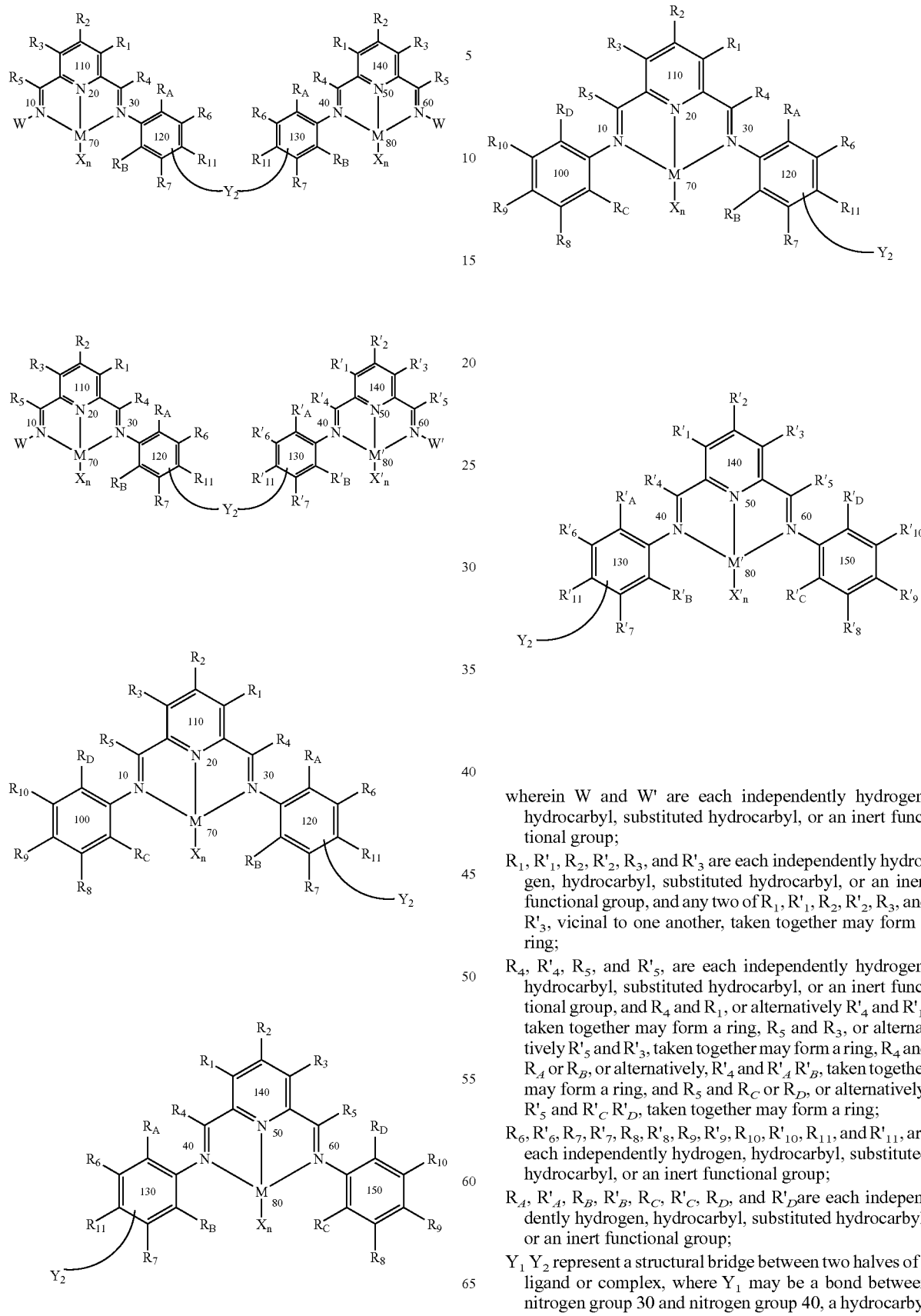

wherein W and W' are each independently hydrogen, hydrocarbyl, substituted hydrocarbyl, or an inert functional group;

$R_1$, $R'_1$, $R_2$, $R'_2$, $R_3$, and $R'_3$ are each independently hydrogen, hydrocarbyl, substituted hydrocarbyl, or an inert functional group, and any two of $R_1$, $R'_1$, $R_2$, $R'_2$, $R_3$, and $R'_3$, vicinal to one another, taken together may form a ring;

$R_4$, $R'_4$, $R_5$, and $R'_5$, are each independently hydrogen, hydrocarbyl, substituted hydrocarbyl, or an inert functional group, and $R_4$ and $R_1$, or alternatively $R'_4$ and $R'_1$, taken together may form a ring, $R_5$ and $R_3$, or alternatively $R'_5$ and $R'_3$, taken together may form a ring, $R_4$ and $R_A$ or $R_B$, or alternatively, $R'_4$ and $R'_A$ $R'_B$, taken together may form a ring, and $R_5$ and $R_C$ or $R_D$, or alternatively, $R'_5$ and $R'_C$ $R'_D$, taken together may form a ring;

$R_6$, $R'_6$, $R_7$, $R'_7$, $R_8$, $R'_8$, $R_9$, $R'_9$, $R_{10}$, $R'_{10}$, $R_{11}$, and $R'_{11}$, are each independently hydrogen, hydrocarbyl, substituted hydrocarbyl, or an inert functional group;

$R_A$, $R'_A$, $R_B$, $R'_B$, $R_C$, $R'_C$, $R_D$, and $R'_D$ are each independently hydrogen, hydrocarbyl, substituted hydrocarbyl, or an inert functional group;

$Y_1$ $Y_2$ represent a structural bridge between two halves of a ligand or complex, where $Y_1$ may be a bond between nitrogen group 30 and nitrogen group 40, a hydrocarbyl having from about 0 to about 30 carbon atoms, a substi tuted hydrocarbyl having from about 0 to about 30 carbon atoms, or an inert functional group and Y$_2$ may be a bond between aromatic rings 120 and 130, a hydrocarbyl having from about 0 to about 30 carbon atoms, substituted hydrocarbyl having from about 0 to about 30 carbon atoms, or an inert functional group;

M and M' may independently be any metal atom; and

X and X' may independently be any anion.

17. The method of claim 16, wherein the acyliminepyridine metal complex is prepared by:

(a) contacting a di-acylpyridine with an amine to form a first mixture;

(b) recovering an acyliminepyridine compound from the first mixture;

(c) contacting the acyliminepyridine compound with a metal salt to form a second mixture; and, (d) recovering the acyliminepyridine metal complex from the second mixture.

18. The method of claim 17, wherein the metal salt comprises, iron, cobalt, nickel, chromium, vanadium or mixtures thereof.

19. The method of claim 16, wherein the acyliminepyridine metal complex is a mono-acyliminepyridine metal complex and the amine is a diamine.

20. The method of claim 19, wherein a mono-acyliminepyridine metal complex to diamine molar ratio is about 2:1.

21. The method of claim 19, wherein the hexadentate bimetallic complex

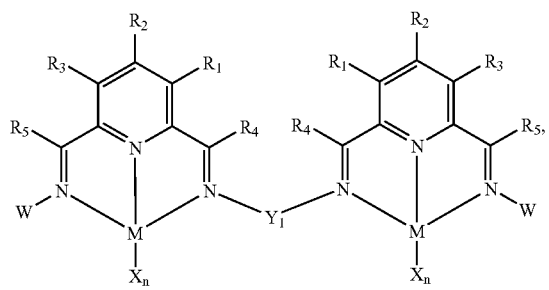

has structure

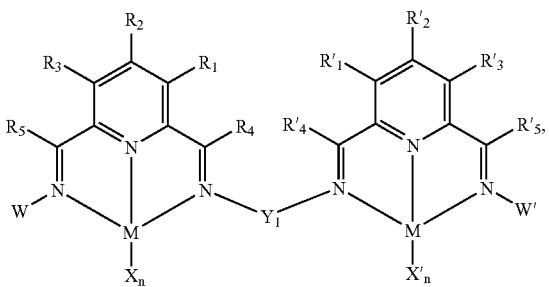

or mixtures thereof, the mono-acyliminepyridine metal complex has structure

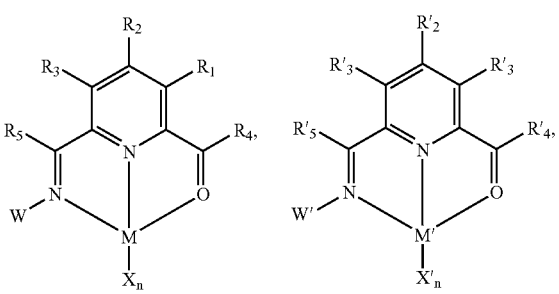

or mixtures thereof, the diamine has structure H$_2$N—Y$_1$—NH$_2$, a mono-acyliminepyridine metal complex to diamine molar ratio is about 2:1.

22. The method of claim 19, wherein the hexadentate bimetallic complex has structure

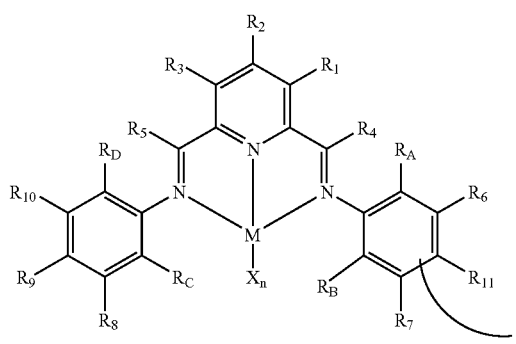

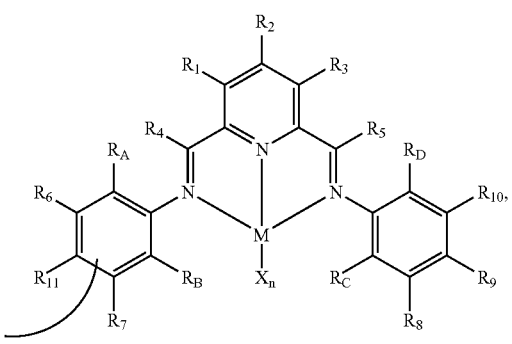

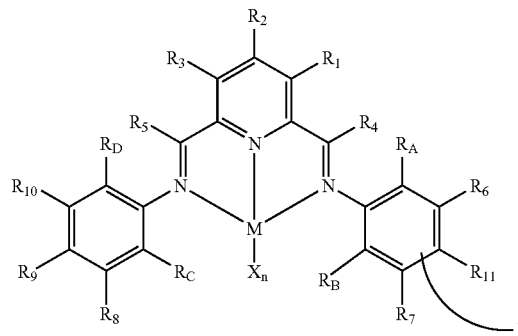

mixtures thereof, the mono-acylimine pyridine metal complex has structure

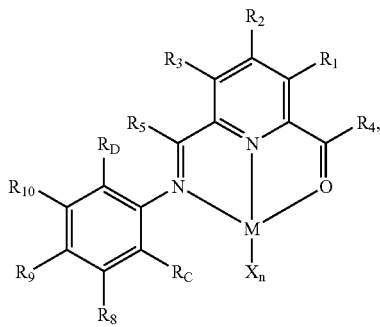

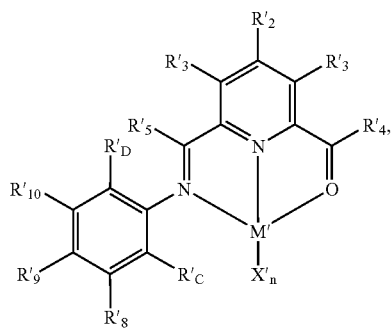

or mixtures thereof, the

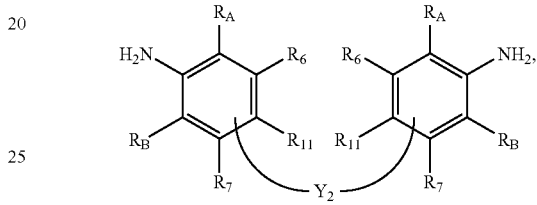

diamine has structure

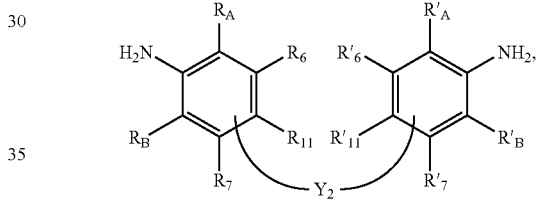

or mixtures thereof, and a mono-acyliminepyridine metal complex to diamine molar ratio is about 2:1.

23. The method of claim 19, wherein the mono-acyliminepyridine metal complex is prepared by:
(a) contacting a di-acylpyridine with a monoamine to form a first mixture;
(b) recovering a mono-acyliminepyridine compound from the first mixture;
(c) contacting the mono-acyliminepyridine compound with a metal salt to form a second mixture; and,
(d) recovering the mono-acyliminepyridine metal complex from the second mixture.

24. The method of claim 23, wherein a di-acylpyridine to monoamine molar ratio is about 1:1.

25. The method of claim 23, wherein a mono-acyliminepyridine compound to metal salt molar ratio is about 1:1.

\* \* \* \* \*